US006472518B1

(12) United States Patent
Ribot et al.

(10) Patent No.: US 6,472,518 B1
(45) Date of Patent: Oct. 29, 2002

(54) **INVASION ASSOCIATED GENES FROM *NEISSERIA MENINGITIDIS* SEROGROUP B**

(75) Inventors: Efrain M. Ribot, Atlanta; David S. Stephens, Stone Mountain, both of GA (US); Nigel Raymond, Wellington (NZ); Frederick D. Quinn, Avondale Estates, GA (US)

(73) Assignee: Centers for Disease Control and Prevention, as represented by the Secretary, Department of Health and Human Services, Atlanta, GA (US)

( * ) Notice: Subject to any disclaimer, the term of this patent is extended or adjusted under 35 U.S.C. 154(b) by 0 days.

(21) Appl. No.: 09/284,926

(22) PCT Filed: Oct. 24, 1997

(86) PCT No.: PCT/US97/19424

§ 371 (c)(1),
(2), (4) Date: Aug. 17, 1999

(87) PCT Pub. No.: WO98/17805

PCT Pub. Date: Apr. 30, 1998

Related U.S. Application Data

(60) Provisional application No. 60/030,432, filed on Oct. 24, 1996.

(51) Int. Cl.$^7$ ............................................. C07H 21/04
(52) U.S. Cl. ................ 536/23.7; 536/24.32; 536/24.33; 536/24.1; 424/250.1; 435/243; 435/252.3; 435/320.1; 435/69.1; 435/69.3
(58) Field of Search ........................... 536/23.7, 24.32, 536/24.1, 24.33; 435/69.1, 69.3, 320.1, 243, 252.3; 424/250.1

(56) References Cited

FOREIGN PATENT DOCUMENTS

| DE | 19534579 A1 | 3/1997 |
|---|---|---|
| WO | WO 94/08013 | 4/1994 |

OTHER PUBLICATIONS

Aho, et al., "Characterization of the opa (class 5) Gene Family of *Neisseria Meningitidis*," *Mol. Microbiol.*, vol. 5, pp. 1429–1437 (1991).

Beall, et al., "Cloning and Characterization of *Bacillus subtilis* Homologs of *Escherichia coli* Cell Division Genes ftsZ and ftsA," *J. Bacteriol.*, vol. 170, pp. 4855–4864 (1988).

Birkness, et al., "A Tissue Culture Bilayer Model to Study the Passage of *Neisseria meningitidis*," *Infect. Immun.*, vol. 63, pp. 402–409 (1995).

Buddingh G.J., "Meningococcus Infection of the Chick Embryo," *Science*, vol. 86, No. 2218, pp. 20–21 (1937).

Cook, et al., "Early Stages in Development of the *Escherichia coli* Cell–Division Site," *Mol. Microbiol.*, vol. 14, pp. 485–495 (1994).

Corton, et al., "Analysis of Cell Division Gene ftsZ (sulB) from Gram–Negative and Gram–Positive Bacteria," *J. Bacteriol.*, vol. 169, pp. 1–7 (1987).

Daines, et al., Phenotypic Analysis of Invasion–Deficient Insertion Mutants of *Neisseria gonorrhoeae*, University of Rochester, N.Y. (Abstract).

de Boer, et al., "The Essential Bacterial Cell–division Protein FtsZ is a GTPase," *Nature*, vol. 359, pp. 254–256 (1992).

Mannino, et al., "Liposome Mediated Gene Transfer," *BioTechniques*, vol. 6, No. 7, pp. 682–690 (1988).

Holbein, "Differences in Virulence for Mice between Disease and Carrier Strains of *Neisseria meningitidis*," *Can. J. Microbiol.*, vol. 27, pp. 738–741 (1981).

Kathariou, et al., "Transposition of Tn916 to Different Sites in the Chromosome of *Neisseria meningitidis*: a Genetic Tool for *Meningococcal mutagenesis*," *Mol. Microbiol.*, vol. 4, No. 5, pp. 729–735 (1990).

Kwoh, et al., "Transcription–based Amplification System and Detection of Amplified Human Immunodeficiciency Virus Type 1 with a bead–based Sandwich Hybridization Format," *Proc. Natl. Acad. Sci. USA*, vol. 86, pp. 1173–1177 (1989).

Yu, et al., "Intracellular Immunization of Human Fetal Cord Blood Stem/Progenitor Cells with a Ribozyme Against Human Immunodeficiency Virus Type 1," *Proc. Natl. Acad. Sci. USA*, vol. 92, pp. 699–703 (1995).

Lutkenhaus, et al., "Organization of Genes in the ftsA–envA Region of the *Escherichia coli* Genetic Map and Identification of a New fts Locus (ftsZ)," *J. Bacteriol.*, vol. 142, pp. 615–620 (1980).

Margolin, et al., "Isolation of an ftsZ Homolog from the Archaebacterium *Halobacterium salinarium*: Implications for the Evolution of FtsZ and Tubulin," *J. of Bacteriol.*, vol. 178, No. 5, pp. 1320–1327 (1996).

McCormick, et al., "Growth and Viability of *Streptomyces coelicolor* Mutant for the Cell Division Gene ftsZ," *Mol. Microbiol.*, vol. 14, pp. 243–254 (1994).

Miller, "Experimental Meningococcal Infection in Mice," *Science*, vol. 78, pp. 340–341 (1933).

Moore, et al., "Cerebrospinal Meningitis Epidemics," *Scientific American*, pp. 38–45 (1994).

(List continued on next page.)

*Primary Examiner*—Jennifer E. Graser
(74) *Attorney, Agent, or Firm*—Needle & Roseberg, P.C.

(57) ABSTRACT

Genes isolated from *Neisseria memingitidis*, as well as isolated nucleic acids, probes, expression cassettes, polypeptides, antibodies, immunogenic compositions, antisense nucleic acids, amplification mixtures, and new invasion deficient swains of *Neisseria meningitidis* are provided Methods of detecting *Neisseria meningitidis* and *Neisseria meningitidis* nucleic acids, and methods of inhibiting the invasion of mammalian cells by *Neisseria meningitidis* are also provided.

7 Claims, 27 Drawing Sheets

OTHER PUBLICATIONS

Mulligan, "The Basic Science of Gene Therapy," *Science*, pp. 926–932 (1993).

Mukherjee, et al., "*Escherichia coli* Cell Division Protein FtsZ is a Guanine Nucleotide Binding Protein," *Proc. Natl. Acad. Sci. USA*, vol. 90, pp. 1053–1057 (1993).

Nassif, et al., "Interaction of Pathogenic Neisseriae with Nonphagocytic Cells," *Clinical Microbiology Reviews*, vol. 8, No. 3, pp. 376–388 (1995).

Pine, et al., "Evaluation of the Chick Embryo for the Determination of Relative Virulence of *Neisseria meningitidis*, " *FEMS Microbiology Letters*, vol. 130, pp. 37–44 (1995).

Poolman, "Development of a Meningococcal Vaccine," *Infectious Agents and Disease*, vol. 4, pp. 13–28 (1995).

Ribot, et al., "Molecular Characterization of a *Neisseria meningitidis* Adhesion and Invasion–Deficient Mutant," 34$^{th}$ Interscience Conference on Antimicrobial Agents and Chemotherapy, Orlando, Florida (Oct. 4–7, 1994) (Abstract).

Ribot, et al., "Cellular Analysis of an Invasion–Deficient *Neisseria meningitidis* Serogroup B, Strain NMB, Tn916 Transposon Mutant," EMBL Databank Accession No. U43329, (Jan. 13, 1996).

Ricard, et al., "Process of Cellular Division in *Escherichia coli*: Physiological Study on Thermosensitive Mutants Defective in Cell Division," *J. Bacteriol.*, vol. 116, pp. 314–322 (1973).

Romero, et al., "Current Status of Meningococcal Group B Vaccine Candidates: Capsular or Noncapsular?," *Clinical Microbiology Reviews*, vol. 7, pp. 559–575 (1994).

Salit, I.E., "Experimental Meningococcal Infection in Neonatal Animals: Models for Mucosal Invasiveness," *Can. J. Microbiol.*, vol. 30, pp. 1022–1029 (1984).

Saukkonen, et al., "Comparative Evaluation of Potential Components for Group B Meningococcal Vaccine by Passive Protection in the Infant Rat and In Vitro Bactericidal Assay," *Vaccine*, vol. 7, pp. 325–328 (1989).

Stephens, et al., "Pathogenic Events During Infection of the Human Nasopharynx with *Neisseria meningitidis* and *Haemophilus influenzae*, " *Rev. Infect. Dis.*, vol. 13, pp. 22–33 (1991).

Stephens, et al., "Insertion of Tn916 in *Neisseria meningitidis* Resulting in Loss of Group B Capsular Polysaccharide," *Infect. Immun.*, vol. 59, pp. 4097–4102 (1991).

Swartley, et al., "Deletions of Tn916–like Transposons are implicated in tetM–mediated Resistance in Pathogenic Nesseria," *Mol. Microbiol.*, vol. 10, pp. 299–310 (1993).

Fisher, et al., "Ten–Year Results of a Randomized Clinical Trial Comparing Radical Mastectomy and Total Mastectomy with or without Radiation," The Journal of NIH Research, vol. 3, pp. 81–89 (1991).

Van der Ley, et al., "Construction of a Multivalent Meningococcal Vaccine Strain based on the Class 1 Outer Membrane Protein," *Infect. Immun.*, vol. 60, pp. 3156–3161 (1992).

Van der Ley, et al., "Use of Transformation to Construct Antigenic Hybrids of the Class 1 Outer Membrane Protein in *Neisseria meningitidis*," *Infect. Immun.*, vol. 61, pp. 4217–4224 (1993).

Virji, et al., "Opc– and pilus–dependent Interactions of Meningococci with Human Endothelial Cells: Molecular Mechanisms and Modulation by Surface Polysaccharides," *Mol. Microbiol.*, vol. 18, No. 4, pp. 741–754 (1995).

TGCAGGCATGCAAGCTGGAAGGAAACTTGCCGCAGCCAGGAAAACGGTGC

AGTGCAAGAGAGGGAAGGGGGCGGCGGTTTGTTGGCAAGATTGAAACGGT

GGATTGAAAACAGCTTCTGAACAGGTGGATTGCCGTTTGACAGGTGAGAA

GTATTTTGCCAGCAGCAAGATACTTCTTATATAATGAATAATAATTTATT

RBS              ORF1
TAAACCGTCCTCTGAATGGGGCGAGCAGGAGTTTTTGAATGGAATTTGTT

TACGACGTGGCAGAATCCGGCAGTCCGACCTGCGGTGATTAAAGTAATCC

GGCTTGGGCGGCCGGCGGTTGGCAATGCAATCAATAACATGGTTGCCAAC

AATGTGCGCGGTGTGGAGTTTATCAGTGCCAATAACGGATGCGCAGTCTC

TGGCAAAAAACCATGCGGCGAAGAGAATCCAGTTGGTTACGAATCTGACA

CGCGGTTTGGGCGCGGCGNAATTCCCGATATCGGCCGTGCCGGAGCCCAG

GAAGACGGGAAGCCATTGAGAAGAAGCATTCGCGGTGCGAATTTGCTGTT

TATCACGACCGGTATGGGCGGCGGTACCGGTACCGGTTCCGCGCCGTTGT

TGCTGAGATTGCAAGTCTTGGGCATCTGACCGTTGCCGTGGTTACCCGAC

CGTTCGCATTTGAAGGGTAATGCCGCGTCCAGGTCGCACAGCCAGGTTGG

ACAGTTGAAGAACACGTCGATTCGCTGATTATCATCCCGAACGACAAACT

GATGACTGCATGGGTGAAGACGTAACGATGCGCGACGCTTCCGTGCCGCC

GACAATGTTTGCGCGATGCGGTCGAGGCATTCCGGAAGTGGTAACTTGCC

GAGCGAAATCATCCAACCTCGACTTTTGCCGACGTGAAAACCGTGATGAG

CAACCGCGGTATCGCTATGATGGGTTCGGGTTATGCCCAAGGTATCCGAC

CGTGCGCGTATGGCGACCGACCAGGCCATTTCCAGTCCGCTGCTGGACGA

TGTAACCTTGGACGGAGCGCGCGGTGTGCTGGTCAATATTACGACTGCTC

CGGGTTGCTTGAAAATGTCCGAGTTGTCCGAAGTCATGAAAATCGTCAAC

CAAAGCGCGCATCCCGATTTGGAATGCAAATTCGGTGCTGCTGAAGACGA

GACCATGAGCGAAGATGCCATCCGGATTACCATTATCGCTACCGGTCTGA

FIG.4A

AAGAAAAAGGCGCGGTCGATTTTGTTCCGGCAAGGGAGGTAGAAGCGGTT

GCCCCGTCCAAACAGGAGCAAAGCCACAATGTCGAAGGTATGATCCGCAC

CAATCGCGGTATCCGCACGATGAACCTTACCGCTGCGGATTTCGACAATC

AGTCCGT

END OF ORF1

ACTTGACGACTTTGAAATCCCTGCGATTTTGCGTCGTCAACACAATTCAG

ACAAATAATGTGCTGTTTGCCCGTAAACCTGCTGCCTCCCGAATCGGTTT

GTCCGGTTTGGGAGGTATGTTTTTCAAGATGTTGCAATTTCGTACGGTTT

GCGGTCGGCGGATTCAGATTTTTCCACTTGATACAGACTTTCAGATATGG

ACACTTCAAAACAAACACTGTTGGACGGGATTTTTAAGCTGAAGGCAAAC

GGTACGACGGTGCGTACCGAGTTGATGGCGGGTTTGACAACTTTTTTGAC

GATGTGCTACATCGTTAATCGTCAACCCTCTGATTTTGGGCGAGACCGGC

ATGGATATGGGGGCGGTATTCGTCGCTACCTGTATCGCGTCTGCCAATCG

GCTGTTTTGTTATGGGTTTTGTCGGCAACTATCCGATTGCACTCGCACCG

GGGATGGGGCTGAATGCCTATTTCACCTTTGCCGTCGTTAAGGGTATGGG

CTGCCTTGGCAGGTTGCGTTGGGTGCGGTGTTCATCTCCGGTCTGATTTT

CATCCTGTTCAGCTTTTTTAAAGTCAGGGAAATGCTGTCAACGCACTGCC

*ORF2        **ORF2
TATGGGTTTGAAAATGTCGATTGCTGCCGGTATCGGTTTGTTTTTGGCAC

TGATTTCCCTGAAAGGCGCAGGCCATTATCGTTGCCAATCCGGCAACCTT

GGTCGGTTTGGGCGATATTCATCAGCCGTCCGCGTTGTTGGCACTGTTCG

GTTTTGCTATGGTGGTCGTATTGGGACATTTCCGCGTTCAAGGCGCAACA

TCATCACCATCTTGACCATTACCGTCATTGCCAGCCTGATGGGTTTGAAT

GAATTTCACGGCATCATCGGCGAAGTACCGAGCATTGCGCCGACTTTTAT

GCAGATGGATTTTGAAGGCCTGTTTACCGTCAGCTGGTCAGTGATTTTCG

FIG.4B

```
TCTTCTTCTTGGTCGATCTATTTGACAGTACCGGAACGCTGGTCGGCATA
TCCCACCGTGCCGGGCTGCTGGTGGACGGTAAGCTGCCCCGCCTGAAACG
CGCACTGCTTGCAGACTCTACCGCCATTATGGCAGGTGCGGCTTTGGGTA
CTTCTTCCACCACGCCTTATGTGGAAAGCGCGGCGGGCGTATCGGCAGGC
GGACGGACCGGCCTGACGGCGGTTACCGTCGGCGTATTGATGCTCGCCTG
CCTGATGTTTTCACCTTTGGCGAAAAGTGTTCCCGCTTTTGGCACCGCGC
CCGCCCTGCTTTATGTCGGCACGCAGATGCTCCGCAGTGCGAGGGATATT
GATTGGGACGATATGACGGAAGCCGCACCCGCATTCCTGACCATTGTCTT
CATGCCGTTTACCTATTCGATTGCAGACGGCATCGCCTTCGGCTTCATCA
GCTATGCCGTGGTTAAACTTTTATGCCGCCGCACCAAAGACGTTCCGCCT
ATGGAATGGGTTGTTGCCGT
     END RF ORF2
ATTGTGGGCACTGAAATTCTGGTATTTGGGCTGATTGATTCGATATTAAA
AATGCCGTCTGAAAGGTTTTCAGACGGCATTTTGTTTGCCGATATATTAA
TTTTTATTAAATTATATAAAAATCAAATACATAATAAAATACATCGGATT
GCTTAAAAATAATACATTGTTTTTTATGTATAAAATATTTTATAAGTTTT
CAGGATTTGGATTATTGAAAATTTTTCTTGATTTCCTGACAATTTTATTG
AAACAAATAATTCAAAATTAATCTAGTTTAATCATAGAATTAAAATAAAA
TATTAAAATTATGTAATGAGTCTCCTTAAAAATGTTTGACATTTTCAGTC
TTGTGTTTTAGATTATCGAAAAATAAAACTACATAACACTACAAAGGAAT
ATTACTATGAAACCAATTCAGATGTTTTCCCCTTTTCTGAATAATCCCCT
TGTTTTCTTCTTGTCTGCGGTTTTGCCGCATAATTCCGAACGGTCTGCTG
TTTTTCTTTGATTCGTTTTAAATATCAATAAGATAATTTTTCCCATATAT
         RBS    ORF3
TTTTAATGATTGGATTGGGATGCCCGACGCGTCGGATGGCTGTGTTTTGC
```

FIG.4C

CGTCCGAATGTGATGGAAGCCTGTCCATACTGAAAAAAAGTCTATAAAGG

AGAAATATGATGAGTCAACACTCTGCCGGAGCACGTTTCCGCCAAGCCGT

GAAAGAATCGAATCCGCTTGCCGTCGCCGGTTGCGTCAATGCTTATTTTG

CACGATTGGCCACCCAAAGCGGTTTCAAAGCCATCTATCTGTCTGGCGGC

GGCGTGGCAGCCTGTTCTTGCGGTATCCCTGATTTGGGCATTACCACAAT

GGAAGATGTGCTGATCGACGCACGACGCATTACGGACAACGTGGATACGC

CTCTGCTGGTGGACATCGATGTGGGTTGGGGCGGTGCATTCAATATTGCC

CGTACCATTCGCAACTTTGAACGCGCCGG

END OF ORF3

TGTTGCAGCGGTTCACATCGAAGATCAGGTAGCGCAAAAACGCTGCGGTC

ACCGTCCGAACAAAGCCATTGTTATCTAAAGATGAAATGGTCGACCGTAT

CAAAGCTGCCGTAGATGCGCGCGTTGATGAGAACTTCGTGATTATGGCGC

GTACCGATGCGCTGGCGGTAGAAGGTTTGGATGCCGCTATCGAACGCGCC

CAAGCTTGTGTCGAAAGCCGGTGCGGACATGATTTTCCCTGAAGCCATGA

CCGATTTGAACATGTACCGCCAATTTGCAGATGCGGTGAAAGTGCGTGTT

GGCGAACATTACCGAGTTTGGTTCCACTCCGCTTTATACCCAAAGCGAGC

TGGCTGAAAACGGCGTGTCGCTGGTGCTGTATCCGCTGTCATCGTTCCGT

GCAGCAAGCAAAGCCGCTCTGAATGTTTACGAAGCGATTATGCGCGATGG

CACTCAGGCGGCGGTGGTGGACAGTATGCAAACCCGTGCCGAGCTGTACG

AGCATCTGAACTATCATGCCTTCGAGCAAAAACTGGATAAATTGTTTCAA

AAATGATTTACCGCTTTCAGACGGTCTTTCAACAAATCCGCATCGGTCGT

CTGAAAACCCGAAACCCATAAAAACACAAAGGAGAAATACCATGACTGAA

ACTACTCAAACCCCGACCTTCAAACCTAAGAAATCCGTTGCGCTTTCAGG

CGTTGCGGCCGGTAATACCGCTTTGTGTACCGTTGGCCGCACCCGGCAAC

GATTTGGAGCTATCGCGGTTACGACATCTTGGATTTGGGCACAAAAATGC

FIG.4D

```
GTTTGAAGAAGTAGCCCACCTGCTGATTCACGGTCATCTGCCCAACAAAT

TCGACGTGGAAGCTTATAAAAGGAAGCTCAAATCCATGCGCGGCCTGCCT

ATCCGTGTATTAAAGTTTTGGGAAAGCCTGCCTGCACATACCCATCCGGA

TGGACGGTAATGGCGTACCGGCGGTATCCATGCTGGGCTGCGTTCATCCC

GAACGTGAAAGCCATCCCGGAAAGTGAAGCGCGCGACATCGCCGACAAAC

TGATTGCAGCCTCGGAGCCTCCTGCTGTACTGGTATCAATATCGCACAAC

GGCAAACGCATTGAGTTGAAGCGACGAGAGACATCGGCGGTCATTTCCTG

CAACTGTTBCACGGCAACGCCCAAGCGATCACACATCAAAGCCATGCACG

TTTCACTGATTCTGTATGCGAACACGAGTTCAACGTTCTACCTTTACCGT

TTGCCGTTCTTCTGGTCGGTTCTAGCCCTGTAAAAAGAGAAGGTTGTTAG

CTGGCGAAGGTTTGCAGCCGTTACAGTTTCCCGCGTTATAGCGGCCAAGA

AACGAGTTTGGCGCACGGTGAGAATTACCTGTTGCAACGCCCCAGCCTTT

ACCATATGTGGGCCTACTGGCTTNGGCTAGTGCTAAGAAACGCGGCTATG

CTAGCGCCTACATGCCGAGTGACGAGCGTNACGCCATCGCAAAACTTATA

CGCATTTCGGGAAGCCAANCGCTGGCGGCACAAAGCCTGGATAGTTGTGC

GGCTAACGNGGCCATTACGACCTCATGTATAGTCCTCTGACATGGCGCTA

NTTGCGCCC
```

FIG.4E

```
          RBS              START
           10               19              28              37              46              55
5' AGC AGG AGT TTT TGA ATG GAA TTT GTT TAC GAC GTG GCA GAA TCG GCA GTC AGC
   --- --- --- --- --- --- --- --- --- --- --- --- --- --- --- --- --- ---
    S   R   S   F   •   M   E   F   V   Y   D   V   A   E   S   A   V   S 64              73              82              91             100             109
   CCT GCG GTG ATT AAA GTA ATC GGC TTG GGC GGC GGC GGT TGC AAT GCA TCC AAT
   --- --- --- --- --- --- --- --- --- --- --- --- --- --- --- --- --- ---
    P   A   V   I   K   V   I   G   L   G   G   G   G   C   N   A   S   N 118             127             136             145             154             163
   AAC ATG GTT GCC AAC AAT GTG CGC GGT GTG GAG TTT ATC AGT GCC AAT ACG GAT
   --- --- --- --- --- --- --- --- --- --- --- --- --- --- --- --- --- ---
    N   M   V   A   N   N   V   R   G   V   E   F   I   S   A   N   T   D 172             181             190             199             208             217
   GCG CAG TCT CTG GCA AAA AAC CAT GCG GCG AAG AGA ATC CAG TTG GGT ACG AAT
   --- --- --- --- --- --- --- --- --- --- --- --- --- --- --- --- --- ---
    A   Q   S   L   A   K   N   H   A   A   K   R   I   Q   L   G   T   N 226             235             244             253             262             271
   CTG ACA CGC GGT TTG GGC GCG GGC GCG AAT CCC GAT ATC GGC CGT GCG GCA GCC
   --- --- --- --- --- --- --- --- --- --- --- --- --- --- --- --- --- ---
    L   T   R   G   L   G   A   G   A   N   P   D   I   G   R   A   A   A 280             289             298             307             316             325
   CAG GAA GAC CGG GAA GCC ATT GAA GAA GCC ATT CGC GGT GCG AAT ATG CTG TTT
   --- --- --- --- --- --- --- --- --- --- --- --- --- --- --- --- --- ---
    Q   E   D   R   E   A   I   E   E   A   I   R   G   A   N   M   L   F 334             343             352             361             370             379
   ATC ACG ACC GGT ATG GGC GGC GGT ACC GGT ACC GGT TCC GCG CCG GTT GTT GCT
   --- --- --- --- --- --- --- --- --- --- --- --- --- --- --- --- --- ---
    I   T   T   G   M   G   G   G   T   G   T   G   S   A   P   V   V   A 388             397             406             415             424             433
   GAG ATT GCC AAG TCT TTG GGC ATT CTG ACC GTT GCC GTG GTT ACC CGA CCG TTC
   --- --- --- --- --- --- --- --- --- --- --- --- --- --- --- --- --- ---
    E   I   A   K   S   L   G   I   L   T   V   A   V   V   T   R   P   F 442             451             460             469             478             482
   GCA TAT GAA GGT AAG CGC GTC CAT GTC GCA CAG GCA GGG TTG GAA CAG TTG AAA
   --- --- --- --- --- --- --- --- --- --- --- --- --- --- --- --- --- ---
    A   Y   E   G   K   R   V   H   V   A   Q   A   G   L   E   Q   L   K 496             505             514             523             532             541
   GAA CAC GTC GAT TCG CTG ATT ATC ATC CCG AAC GAC AAA CTG ATG ACT GCA TTG
   --- --- --- --- --- --- --- --- --- --- --- --- --- --- --- --- --- ---
    E   H   V   D   S   L   I   I   I   P   N   D   K   L   M   T   A   L 550             559             568             577             586             595
   GGT GAA GAC GTA ACG ATG CGC GAA GCC TTC CGT GCC GCC GAC AAT GTA TTG CGC
   --- --- --- --- --- --- --- --- --- --- --- --- --- --- --- --- --- ---
    G   E   D   V   T   M   R   E   A   F   R   A   A   D   N   V   L   R 604             613             622             631             640             649
   GAT CGC GTC GCA GGC ATT TCC GAA GTG GTA ACT TGC CCG AGC GAA ATC ATC AAC
   --- --- --- --- --- --- --- --- --- --- --- --- --- --- --- --- --- ---
    D   A   V   A   G   I   S   E   V   V   T   C   P   S   E   I   I   N
```

FIG.5A

```
     658            667            676            685            694            703
CTC GAC TTT GCC GAC GTG AAA ACC GTG ATG AGC AAC CGC GGT ATC GCT ATG ATG
--- --- --- --- --- --- --- --- --- --- --- --- --- --- --- --- --- ---
 L   D   F   A   D   V   K   T   V   M   S   N   R   G   I   A   M   M 712            721            730            739            748            757
GGT TCG GGT TAT GCC CAA GGT ATC GAC CGT GCG CGT ATG GCG ACC GAC CAG GCC
--- --- --- --- --- --- --- --- --- --- --- --- --- --- --- --- --- ---
 G   S   G   Y   A   Q   G   I   D   R   A   R   M   A   T   D   Q   A 766            775            784            793            802            811
ATT TCC AGT CCG CTG CTG GAC GAT GTA ACC TTG GAC GGA GCG CGC GGT GTG CTG
--- --- --- --- --- --- --- --- --- --- --- --- --- --- --- --- --- ---
 I   S   S   P   L   L   D   D   V   T   L   D   G   A   R   G   V   L 820            829            838            847            856            865
GTC AAT ATT ACG ACT GCT CCG GGT TGC TTG AAA ATG TCC GAG TTG TCC GAA GTC
--- --- --- --- --- --- --- --- --- --- --- --- --- --- --- --- --- ---
 V   N   I   T   T   A   P   G   C   L   K   M   S   E   L   S   E   V 874            883            892            901            910            919
ATG AAA ATC GTC AAC CAA AGC GCG CAT CCC GAT TTG GAA TGC AAA TTC GGT GCT
--- --- --- --- --- --- --- --- --- --- --- --- --- --- --- --- --- ---
 M   K   I   V   N   Q   S   A   H   P   D   L   E   C   K   F   G   A 928            937            946            955            964            973
GCT GAA GAC GAG ACC ATG AGC GAA GAT GCC ATC CGG ATT ACC ATT ATC GCT ACC
--- --- --- --- --- --- --- --- --- --- --- --- --- --- --- --- --- ---
 A   E   D   E   T   M   S   E   D   A   I   R   I   T   I   I   A   T 982            991           1000           1009           1018           1027
GGT CTG AAA GAA AAA GGC GCG GTC GAT TTT GTT CCG GCA AGG GAG GTA GAA GCG
--- --- --- --- --- --- --- --- --- --- --- --- --- --- --- --- --- ---
 G   L   K   E   K   G   A   V   D   F   V   P   A   R   E   V   E   A 1036           1045           1054           1063           1072           1081
GTT GCC CCG TCC AAA CAG GAG CAA AGC CAC AAT GTC GAA GGT AGA TCC GCA CCA
--- --- --- --- --- --- --- --- --- --- --- --- --- --- --- --- --- ---
 V   A   P   S   K   Q   E   Q   S   H   N   V   E   G   R   S   A   P 1090           1099           1108           1117           1126           1135
ATC GCG GTA TCC GCA CGA TGA ACC TTA CCG CTG CGG ATT TCG ACA ATC AGT CCG
--- --- --- --- --- --- --- --- --- --- --- --- --- --- --- --- --- ---
 I   A   V   S   A   R   •   T   L   P   L   R   I   S   T   I   S   P 1144           1153           1162           1171           1180
TAC TTG ACG ACT TGA AAT CCC TGC GAT TTT GCG TCG TCA ACA CAA TTC AG    3'
--- --- --- --- --- --- --- --- --- --- --- --- --- --- --- --- ---
 Y   L   T   T   •   N   P   C   D   F   A   S   S   T   Q   F
```

FIG.5B

```
                11              20              29              38  *           47          **  56
5' TTT TAA AGT CAG GGA AAT GCT GTC AAC GCA CTG CCT ATG GGT TTG AAA ATG TCG
    F   •   S   Q   G   N   A   V   N   A   L   P   M   G   L   K   M   S 65              74              83              92             101             110
   ATT GCT GCC GGT ATC GGT TTG TTT TTG GCA CTG ATT TCC CTG AAA GGC GCA GGC
    I   A   A   G   I   G   L   F   L   A   L   I   S   L   K   G   A   G 119             128             137             146             155             164
   CAT TAT CGT TGC CAA TCC GGC AAC CTT GGT CGG TTT GGG CGA TAT TCA TCA GCC
    H   Y   R   C   Q   S   G   N   L   G   R   F   G   R   Y   S   S   A 173             182             191             200             209             218
   GTC CGC GTT GTT GGC ACT GTT CGG TTT TGC TAT GGT GGT CGT ATT GGG ACA TTT
    V   R   V   V   G   T   V   R   F   C   Y   G   G   R   I   G   T   F 227             236             245             254             263             272
   CCG CGT TCA AGG CGC AAC ATC ATC ACC ATC TTG ACC ATT ACC GTC ATT GCC AGC
    P   R   S   R   R   N   I   I   T   I   L   T   I   T   V   I   A   S 281             290             299             308             317             326
   CTG ATG GGT TTG AAT GAA TTT CAC GGC ATC ATC GGC GAA GTA CCG AGC ATT GCG
    L   M   G   L   N   E   F   H   G   I   I   G   E   V   P   S   I   A 335             344             353             362             371             380
   CCG ACT TTT ATG CAG ATG GAT TTT GAA GGC CTG TTT ACC GTC AGC TGG TCA GTG
    P   T   F   M   Q   M   D   F   E   G   L   F   T   V   S   W   S   V 389             398             407             416             425             434
   ATT TTC GTC TTC TTC TTG GTC GAT CTA TTT GAC AGT ACC GGA ACG CTG GTC GGC
    I   F   V   F   F   L   V   D   L   F   D   S   T   G   T   L   V   G 443             452             461             470             479             488
   ATA TCC CAC CGT GCC GGG CTG CTG GTG GAC GGT AAG CTG CCC CGC CTG AAA CGC
    I   S   H   R   A   G   L   L   V   D   G   K   L   P   R   L   K   R 497             506             515             524             533             542
   GCA CTG CTT GCA GAC TCT ACC GCC ATT ATG GCA GGT GCG GCT TTG GGT ACT TCT
    A   L   L   A   D   S   T   A   I   M   A   G   A   A   L   G   T   S
```

\* POSSIBLE START
\*\* POSSIBLE START

FIG.6A

```
            551             560             569             578             587             596
TCC ACC ACG CCT TAT GTG GAA AGC GCG GCG GGC GTA TCG GCA GGC GGA CGG ACC
--- --- --- --- --- --- --- --- --- --- --- --- --- --- --- --- --- ---
 S   T   T   P   Y   V   E   S   A   A   G   V   S   A   G   G   R   T 605             614             623             632             641             650
GGC CTG ACG GCG GTT ACC GTC GGC GTA TTG ATG CTC GCC TGC CTG ATG TTT TCA
--- --- --- --- --- --- --- --- --- --- --- --- --- --- --- --- --- ---
 G   L   T   A   V   T   V   G   V   L   M   L   A   C   L   M   F   S 659             668             677             686             695             704
CCT TTG GCG AAA AGT GTT CCC GCT TTT GGC ACC GCG CCC GCC CTG CTT TAT TGC
--- --- --- --- --- --- --- --- --- --- --- --- --- --- --- --- --- ---
 P   L   A   K   S   V   P   A   F   G   T   A   P   A   L   L   Y   C 713             722             731             740             749             758
GGC ACG CAG ATG CTC CGC AGT GCG AGG GAT ATT GAT TGG GAC GAT ATG ACG GAA
--- --- --- --- --- --- --- --- --- --- --- --- --- --- --- --- --- ---
 G   T   Q   M   L   R   S   A   R   D   I   D   W   D   D   M   T   E 767             776             785             794             803             812
GCC GCA CCC GCA TTC CTG ACC ATT GTC TTC ATG CCG TTT ACC TAT TCG ATT GCA
--- --- --- --- --- --- --- --- --- --- --- --- --- --- --- --- --- ---
 A   A   P   A   F   L   T   I   V   F   M   P   F   T   Y   S   I   A 821             830             839             848             857             866
GAC GGC ATC GCC TTC GGC TTC ATC AGC TAT GCC GTG GTT AAA CTT TTA TGC CGC
--- --- --- --- --- --- --- --- --- --- --- --- --- --- --- --- --- ---
 D   G   I   A   F   G   F   I   S   Y   A   V   V   K   L   L   C   R 875             884             893             902             911             920
CGC ACC AAA GAC GTT CCG CCT ATG GAA TGG GTT GTT GCC GTA TTG TGG GCA CTG
--- --- --- --- --- --- --- --- --- --- --- --- --- --- --- --- --- ---
 R   T   K   D   V   P   P   M   E   W   V   V   A   V   L   W   A   L 929             938             947             956
AAA TTC TGG TAT TTG GGC TGA TTG ATT CGA TAT TAA AAA T      3'
--- --- --- --- --- --- --- --- --- --- --- --- ---   -
 K   F   W   Y   L   G   •   L   I   R   Y   •   K
```

FIG.6B

```
              RBS        START
               10         19              28              37              46              55
5'  AAT GAT  TGG ATT  GGG  ATG  CCC GAC GCG TCG GAT GGC TGT GTT TTG CCG TCC GAA
    --- ---  --- ---  ---  ---  --- --- --- --- --- --- --- --- --- --- --- ---
     N   D    W   I    G    M    P   D   A   S   D   G   C   V   L   P   S   E 64             73              82              91             100             109
    TGT GAT  GGA AGC CTG TCC ATA CTG AAA AAA AGT CTA TAN AGG AGA AAT ATG ATG
    --- ---  --- --- --- --- --- --- --- --- --- --- --- --- --- --- --- ---
     C   D    G   S   L   S   I   L   K   K   S   L   X   R   R   N   M   M 118             127             136             145             154             163
    AGT CAA  CAC TCT GCC GGA GCA CGT TTC CGC CAA GCC GTG AAA GAA TCG AAT CCG
    --- ---  --- --- --- --- --- --- --- --- --- --- --- --- --- --- --- ---
     S   Q    H   S   A   G   A   R   F   R   Q   A   V   K   E   S   N   P 172             181             190             199             208             217
    CTT GCC  GTC GCC GGT TGC GTC AAT GCT TAT TTT GCA CGA TTG GCC ACC CAA AGC
    --- ---  --- --- --- --- --- --- --- --- --- --- --- --- --- --- --- ---
     L   A    V   A   G   C   V   N   A   Y   F   A   R   L   A   T   Q   S 226             235             244             253             262             271
    GGT TTC  AAA GCC ATC TAT CTG TCT GGC GGC GGC GTG GCA GCC TGT TCT TGC GGT
    --- ---  --- --- --- --- --- --- --- --- --- --- --- --- --- --- --- ---
     G   F    K   A   I   Y   L   S   G   G   G   V   A   A   C   S   C   G 280             289             298             307             316             325
    ATC CCT  GAT TTG GGC ATT ACC ACA ATG GAA GAT GTG CTG ATC GAC GCA CGA CGC
    --- ---  --- --- --- --- --- --- --- --- --- --- --- --- --- --- --- ---
     I   P    D   L   G   I   T   T   M   E   D   V   L   I   D   A   R   R 335             343             352             361             370             379
    ATT ACG  GAC AAC GTG GAT NCG CCT CTG CTG GTG GAC ATC GAT GTG GGT TGG GGC
    --- ---  --- --- --- --- --- --- --- --- --- --- --- --- --- --- --- ---
     I   T    D   N   V   D   X   P   L   L   V   D   I   D   V   G   W   G 334             397             406             415             424             433
    GGT GCA  TTC AAT ATT GCC CGT ACC ATT CGC AAC TTT GAA CGC GCC GGT GTT GCA
    --- ---  --- --- --- --- --- --- --- --- --- --- --- --- --- --- --- ---
     G   A    F   N   I   A   R   T   I   R   N   F   E   R   A   G   V   A 442             451
    GCG GTT  CAC ATC GAA GAT CAG GTA
    --- ---  --- --- --- --- --- ---
     A   V    H   I   E   D   Q   V
```

FIG.7A

```
                  9               18              27              36              45              54
5' TAA TTT TTC CCA TAT ATT TTT AAT GAT TGG ATT GGG ATG CCC GAC GCG TCG GAT
    •   F   F   P   Y   I   F   N   D   W   I   G   M   P   D   A   S   D 63              72              81              90              99             108
   GGC TGT GTT TTG CCG TCC GAA TGT GAT GGA AGC CTG TCC ATA CTG AAA AAA AGT
    G   C   V   L   P   S   E   C   D   G   S   L   S   I   L   K   K   S 117             126             135             144             153             162
   CTA TAN AGG AGA AAT ATG ATG AGT CAA CAC TCT GCC GGA GCA CGT TTC CGC CAA
    L   X   R   R   N   M   M   S   Q   H   S   A   G   A   R   F   R   Q 171             180             189             198             207             216
   GCC GTG AAA GAA TCG AAT CCG CTT GCC GTC GCC GGT TGC GTC AAT GCT TAT TTT
    A   V   K   E   S   N   P   L   A   V   A   G   C   V   N   A   Y   E 225             234             243             252             261             270
   GCA CGA TTG GCC ACC CAA AGC GGT TTC AAA GCC ATC TAT CTG TCT GGC GGC GGC
    A   R   L   A   T   Q   S   G   F   K   A   I   Y   L   S   G   G   G 279             288             297             306             315             324
   GTG GCA GCC TGT TCT TGC GGT ATC CCT GAT TTG GGC ATT ACC ACA ATG GAA GAT
    V   A   A   C   S   C   G   I   P   D   L   G   I   T   T   M   E   D 333             342             351             360             369             378
   GTG CTG ATC GAC GCA CGA CGC ATT ACG GAC AAC GTG GAT ACG CCT CTG CTG GTG
    V   L   I   D   A   R   R   I   T   D   N   V   D   T   P   L   L   V 387             396             405             414             423             432
   GAC ATC GAT GTG GGT TGG GGC GGT GCA TTC AAT ATT GCC CGT ACC ATT CGC AAC
    D   I   D   V   G   W   G   G   A   F   N   I   A   R   T   I   R   N 441             450             459             468             477             486
   TTT GAA CGC GCC GGT GTT GCA GCG GTT CAC ATC GAA GAT CAG GTA GCG CAA AAA
    F   E   R   A   G   V   A   A   V   H   I   E   D   Q   V   A   Q   K 495             504             513             522             531             540
   CGC TGC GGT CAC CGT CCG AAC AAA GCC ATT GTT ATC TNA AGA TGN AAT GGT CGA
    R   C   G   H   R   P   N   K   A   I   V   I   X   R   X   N   G   R 549             558             567             576             585             594
   CCG TAT CAA AGC TGC CGT AGA TGC GCG CGT TGN TGN NAG AAC TTC GTG ATT ATG
    P   Y   Q   S   C   R   R   C   A   R   X   X   X   N   F   V   I   M 603             612             621             630             639             648
   GCG CGT ACC GAT GCG CTG GCG GTA GAA GGT TTG GAT GCC GCT ATC GAA CGC GCC
    A   R   T   D   A   L   A   V   E   G   L   D   A   A   I   E   R   A
```

FIG.7B

```
              657              666              675              684
CAA GCT TGT GTC GAA AGC CGG TGC GGA CAT GAT TTT CCC     3'
--- --- --- --- --- --- --- --- --- --- --- --- ---
 Q   A   C   V   E   S   R   C   G   H   D   F   P
```

FIG.7C

```
                    10         20         30         40         50
ORF3         1   T---------- ---------- ---------- ---------- ----------    50
ORF2.SEQ     1   T---------- ---------- ---------- ---------- ----------    50
ORF1         1   ---------- ---------- ---------- ---------- ----------     50
PATENT.SEQ   1   TGCAGGCATG CAAGCTGGAA GGAAACTTGC CGCAGCCAGG AAAACGGTGC      50

60         70         80         90        100
ORF3        51   ---------- ---------- ---------- ---------- ----------   100
ORF2.SEQ    51   ---------- ---------- ---------- ---------- ----------   100
ORF1        51   ---------- ---------- ---------- ---------- ----------   100
PATENT.SEQ  51   AGTGCAAGAG AGGGAAGGGG GCGGCGGTTT GTTGGCAAGA TTGAAACGGT    100

110        120        130        140        150
ORF3       101   ---------- ---------- ---------- ---------- ----------   150
ORF2.SEQ   101   ---------- ---------- ---------- ---------- ----------   150
ORF1       101   ---------- ---------- ---------- ---------- ----------   150
PATENT.SEQ 101   GGATTGAAAA CAGCTTCTGA ACAGGTGGAT TGCCGTTTGA CAGGTGAGAA    150

160        170        180        190        200
ORF3       151   ---------- ---------- ---------- ---------- ----------   200
ORF2.SEQ   151   ---------- ---------- ---------- ---------- ----------   200
ORF1       151   ---------- ---------- ---------- ---------- ----------   200
PATENT.SEQ 151   GTATTTTGCC AGCAGCAAGA TACTTCTTAT ATAATGAATA ATAATTTATT    200

210        220        230        240        250
ORF3       201   ---------- ---------- ---------- ---------- ----------   250
ORF2.SEQ   201   ---------- ---------- ---------- ---------- ----------   250
ORF1       201   ---------- ---------- --GAGCAGGA GTTTTTGAAT GGAATTTGTT    250
PATENT.SEQ 201   TAAACCGTCC TCTGAATGGG GCGAGCAGGA GTTTTTGAAT GGAATTTGTT    250

260        270        280        290        300
ORF3       251   ---------- ---------- ---------- ---------- ----------   300
ORF2.SEQ   251   ---------- ---------- ---------- ---------- ----------   300
ORF1       251   TACGACGTGG CAGAATCGGC AGTCAGCCCT GCGGTGATTA AAGTAATCGG    300
PATENT.SEQ 251   TACGACGTGG CAGAATCGGC AGTCAGCCCT GCGGTGATTA AAGTAATCGG    300

310        320        330        340        350
ORF3       301   ---------- ---------- ---------- ---------- ----------   350
ORF2.SEQ   301   ---------- ---------- ---------- ---------- ----------   350
ORF1       301   CTTGGGCGGC GGCGGTTGCA ATGCATCCAA TAACATGGTT GCCAACAATG    350
PATENT.SEQ 301   CTTGGGCGGC GGCGGTTGCA ATGCATCCAA TAACATGGTT GCCAACAATG    350

360        370        380        390        400
ORF3       351   ---------- ---------- ---------- ---------- ----------   400
ORF2.SEQ   351   ---------- ---------- ---------- ---------- ----------   400
ORF1       351   TGCGCGGTGT GGAGTTTATC AGTGCCAATA CGGATGCGCA GTCTCTGGCA    400
PATENT.SEQ 351   TGCGCGGTGT GGAGTTTATC AGTGCCAATA CGGATGCGCA GTCTCTGGCA    400

410        420        430        440        450
ORF3       401   ---------- ---------- ---------- ---------- ----------   450
ORF2.SEQ   401   ---------- ---------- ---------- ---------- ----------   450
ORF1       401   AAAAACCATG CGGCGAAGAG AATCCAGTTG GGTACGAATC TGACACGCGG    450
PATENT.SEQ 401   AAAAACCATG CGGCGAAGAG AATCCAGTTG GGTACGAATC TGACACGCGG    450
```

FIG.8A

```
                          460        470        480        490        500
ORF3        451   ---------- ---------- ---------- ---------- ----------   500
ORF2.SEQ    451   ---------- ---------- ---------- ---------- ----------   500
ORF1        451   TTTGGGCGCG GGCGCGAATC CCGATATCGG CCGTGCGGCA GCCCAGGAAG   500
PATENT.SEQ  451   TTTGGGCGCG GGCGCGAATC CCGATATCGG CCGTGCGGCA GCCCAGGAAG   500

510        520        530        540        550
ORF3        501   ---------- ---------- ---------- ---------- ----------   550
ORF2.SEQ    501   ---------- ---------- ---------- ---------- ----------   550
ORF1        501   ACCGGGAAGC CATTGAAGAA GCCATTCGCG GTGCGAATAT GCTGTTTATC   550
PATENT.SEQ  501   ACCGGGAAGC CATTGAAGAA GCCATTCGCG GTGCGAATAT GCTGTTTATC   550

560        570        580        590        600
ORF3        551   ---------- ---------- ---------- ---------- ----------   600
ORF2.SEQ    551   ---------- ---------- ---------- ---------- ----------   600
ORF1        551   ACGACCGGTA TGGGCGGCGG TACCGGTACC GGTTCCGCGC CGGTTGTTGC   600
PATENT.SEQ  551   ACGACCGGTA TGGGCGGCGG TACCGGTACC GGTTCCGCGC CGGTTGTTGC   600

610        620        630        640        650
ORF3        601   ---------- ---------- ---------- ---------- ----------   650
ORF2.SEQ    601   ---------- ---------- ---------- ---------- ----------   650
ORF1        601   TGAGATTGCC AAGTCTTTGG GCATTCTGAC CGTTGCCGTG GTTACCCGAC   650
PATENT.SEQ  601   TGAGATTGCC AAGTCTTTGG GCATTCTGAC CGTTGCCGTG GTTACCCGAC   650

660        670        680        690        700
ORF3        651   ---------- ---------- ---------- ---------- ----------   700
ORF2.SEQ    651   ---------- ---------- ---------- ---------- ----------   700
ORF1        651   CGTTCGCATA TGAAGGTAAG CGCGTCCATG TCGCACAGGC AGGGTTGGAA   700
PATENT.SEQ  651   CGTTCGCATA TGAAGGTAAG CGCGTCCATG TCGCACAGGC AGGGTTGGAA   700

710        720        730        740        750
ORF3        701   ---------- ---------- ---------- ---------- ----------   750
ORF2.SEQ    701   ---------- ---------- ---------- ---------- ----------   750
ORF1        701   CAGTTGAAAG AACACGTCGA TTCGCTGATT ATCATCCCGA ACGACAAACT   750
PATENT.SEQ  701   CAGTTGAAAG AACACGTCGA TTCGCTGATT ATCATCCCGA ACGACAAACT   750

760        770        780        790        800
ORF3        751   ---------- ---------- ---------- ---------- ----------   800
ORF2.SEQ    751   ---------- ---------- ---------- ---------- ----------   800
ORF1        751   GATGACTGCA TTGGGTGAAG ACGTAACGAT GCGCGAAGCC TTCCGTGCCG   800
PATENT.SEQ  751   GATGACTGCA TTGGGTGAAG ACGTAACGAT GCGCGAAGCC TTCCGTGCCG   800

810        820        830        840        850
ORF3        801   ---------- ---------- ---------- ---------- ----------   850
ORF2.SEQ    801   ---------- ---------- ---------- ---------- ----------   850
ORF1        801   CCGACAATGT ATTGCGCGAT GCGGTCGCAG GCATTTCCGA AGTGGTAACT   850
PATENT.SEQ  801   CCGACAATGT ATTGCGCGAT GCGGTCGCAG GCATTTCCGA AGTGGTAACT   850

860        870        880        890        900
ORF3        851   ---------- ---------- ---------- ---------- ----------   900
ORF2.SEQ    851   ---------- ---------- ---------- ---------- ----------   900
ORF1        851   TGCCCGAGCG AAATCATCAA CCTCGACTTT GCCGACGTGA AAACCGTGAT   900
PATENT.SEQ  851   TGCCCGAGCG AAATCATCAA CCTCGACTTT GCCGACGTGA AAACCGTGAT   900

910        920        930        940        950
ORF3        901   ---------- ---------- ---------- ---------- ----------   950
ORF2.SEQ    901   ---------- ---------- ---------- ---------- ----------   950
ORF1        901   GAGCAACCGC GGTATCGCTA TGATGGGTTC GGGTTATGCC CAAGGTATCG   950
PATENT.SEQ  901   GAGCAACCGC GGTATCGCTA TGATGGGTTC GGGTTATGCC CAAGGTATCG   950
```

FIG.8B

```
                         960        970        980        990       1000
ORF3       951  ---------- ---------- ---------- ---------- ----------  1000
ORF2.SEQ   951  ---------- ---------- ---------- ---------- ----------  1000
ORF1       951  ACCGTGCGCG TATGGCGACC GACCAGGCCA TTTCCAGTCC GCTGCTGGAC  1000
PATENT.SEQ 951  ACCGTGCGCG TATGGCGACC GACCAGGCCA TTTCCAGTCC GCTGCTGGAC  1000

1010       1020       1030       1040       1050
ORF3      1001  ---------- ---------- ---------- ---------- ----------  1050
ORF2.SEQ  1001  ---------- ---------- ---------- ---------- ----------  1050
ORF1      1001  GATGTAACCT TGGACGGAGC GCGCGGTGTG CTGGTCAATA TTACGACTGC  1050
PATENT.SEQ 1001 GATGTAACCT TGGACGGAGC GCGCGGTGTG CTGGTCAATA TTACGACTGC  1050

1060       1070       1080       1090       1100
ORF3      1051  ---------- ---------- ---------- ---------- ----------  1100
ORF2.SEQ  1051  ---------- ---------- ---------- ---------- ----------  1100
ORF1      1051  TCCGGGTTGC TTGAAAATGT CCGAGTTGTC CGAAGTCATG AAAATCGTCA  1100
PATENT.SEQ 1051 TCCGGGTTGC TTGAAAATGT CCGAGTTGTC CGAAGTCATG AAAATCGTCA  1100

1110       1120       1130       1140       1150
ORF3      1101  ---------- ---------- ---------- ---------- ----------  1150
ORF2.SEQ  1101  ---------- ---------- ---------- ---------- ----------  1150
ORF1      1101  ACCAAAGCGC GCATCCCGAT TTGGAATGCA AATTCGGTGC TGCTGAAGAC  1150
PATENT.SEQ 1101 ACCAAAGCGC GCATCCCGAT TTGGAATGCA AATTCGGTGC TGCTGAAGAC  1150

1160       1170       1180       1190       1200
ORF3      1151  ---------- ---------- ---------- ---------- ----------  1200
ORF2.SEQ  1151  ---------- ---------- ---------- ---------- ----------  1200
ORF1      1151  GAGACCATGA GCGAAGATGC CATCCGGATT ACCATTATCG CTACCGGTCT  1200
PATENT.SEQ 1151 GAGACCATGA GCGAAGATGC CATCCGGATT ACCATTATCG CTACCGGTCT  1200

1210       1220       1230       1240       1250
ORF3      1201  ---------- ---------- ---------- ---------- ----------  1250
ORF2.SEQ  1201  ---------- ---------- ---------- ---------- ----------  1250
ORF1      1201  GAAAGAAAAA GGCGCGGTCG ATTTTGTTCC GGCAAGGGAG GTAGAAGCGG  1250
PATENT.SEQ 1201 GAAAGAAAAA GGCGCGGTCG ATTTTGTTCC GGCAAGGGAG GTAGAAGCGG  1250

1260       1270       1280       1290       1300
ORF3      1251  ---------- ---------- ---------- ---------- ----------  1300
ORF2.SEQ  1251  ---------- ---------- ---------- ---------- ----------  1300
ORF1      1251  TTGCCCCGTC CAAACAGGAG CAAAGCCACA ATGTCGAAGG TAGATCCGCA  1300
PATENT.SEQ 1251 TTGCCCCGTC CAAACAGGAG CAAAGCCACA ATGTCGAAGG TAGATCCGCA  1300

1310       1320       1330       1340       1350
ORF3      1301  ---------- ---------- ---------- ---------- ----------  1350
ORF2.SEQ  1301  ---------- ---------- ---------- ---------- ----------  1350
ORF1      1301  CCAATCGCGG TATCCGCACG ATGAACCTTA CCGCTGCGGA TTTCGACAAT  1350
PATENT.SEQ 1301 CCAATCGCGG TATCCGCACG ATGAACCTTA CCGCTGCGGA TTTCGACAAT  1350

1360       1370       1380       1390       1400
ORF3      1351  ---------- ---------- ---------- ---------- ----------  1400
ORF2.SEQ  1351  ---------- ---------- ---------- ---------- ----------  1400
ORF1      1351  CAGTCCGTAC TTGACGACTT GAAATCCCTG CGATTTTGCG TCGTCAACAC  1400
PATENT.SEQ 1351 CAGTCCGTAC TTGACGACTT GAAATCCCTG CGATTTTGCG TCGTCAACAC  1400
```

FIG.8C

```
                        1410       1420       1430       1440       1450
ORF3        1401  .......... .......... .......... .......... ..........  1450
ORF2.SEQ    1401  .......... .......... .......... .......... ..........  1450
ORF1        1401  AATTCAG--- .......... .......... .......... ..........  1450
PATENT.SEQ  1401  AATTCAGACA ATAATGTGC TGTTTGCCCG TAAACCTGCT GCCTCCCGAA  1450

1460       1470       1480       1490       1500
ORF3        1451  .......... .......... .......... .......... ..........  1500
ORF2.SEQ    1451  .......... .......... .......... .......... ..........  1500
ORF1        1451  .......... .......... .......... .......... ..........  1500
PATENT.SEQ  1451  TCGGTTTGTC CGGTTTGGGA GGTATGTTTT TCAAGATGTT GCAATTTCGT  1500

1510       1520       1530       1540       1550
ORF3        1501  .......... .......... .......... .......... ..........  1550
ORF2.SEQ    1501  .......... .......... .......... .......... ..........  1550
ORF1        1501  .......... .......... .......... .......... ..........  1550
PATENT.SEQ  1501  ACGGTTTGCG GTCGGCGGAT TCAGATTTTT CCACTTGATA CAGACTTTCA  1550

1560       1570       1580       1590       1600
ORF3        1551  .......... .......... .......... .......... ..........  1600
ORF2.SEQ    1551  .......... .......... .......... .......... ..........  1600
ORF1        1551  .......... .......... .......... .......... ..........  1600
PATENT.SEQ  1551  GATATGGACA CTTCAAAACA AACACTGTTG GACGGGATTT TTAAGCTGAA  1600

1610       1620       1630       1640       1650
ORF3        1601  .......... .......... .......... .......... ..........  1650
ORF2.SEQ    1601  .......... .......... .......... .......... ..........  1650
ORF1        1601  .......... .......... .......... .......... ..........  1650
PATENT.SEQ  1601  GGCAAACGGT ACGACGGTGC GTACCGAGTT GATGGCGGGT TTGACAACTT  1650

1660       1670       1680       1690       1700
ORF3        1651  .......... .......... .......... .......... ..........  1700
ORF2.SEQ    1651  .......... .......... .......... .......... ..........  1700
ORF1        1651  .......... .......... .......... .......... ..........  1700
PATENT.SEQ  1651  TTTTGACGAT GTGCTACATC GTTAATCGTC AACCCTCTGA TTTTGGGCGA  1700

1710       1720       1730       1740       1750
ORF3        1701  .......... .......... .......... .......... ..........  1750
ORF2.SEQ    1701  .......... .......... .......... .......... ..........  1750
ORF1        1701  .......... .......... .......... .......... ..........  1750
PATENT.SEQ  1701  GACCGGCATG GATATGGGGG CGGTATTCGT CGCTACCTGT ATCGCGTCTG  1750

1760       1770       1780       1790       1800
ORF3        1751  .......... .......... .......... .......... ..........  1800
ORF2.SEQ    1751  .......... .......... .......... .......... ..........  1800
ORF1        1751  .......... .......... .......... .......... ..........  1800
PATENT.SEQ  1751  CCAATCGGCT GTTTTGTTAT GGGTTTTGTC GGCAACTATC CGATTGCACT  1800

1810       1820       1830       1840       1850
ORF3        1801  .......... .......... .......... .......... ..........  1850
ORF2.SEQ    1801  .......... .......... .......... .......... ..........  1850
ORF1        1801  .......... .......... .......... .......... ..........  1850
PATENT.SEQ  1801  CGCACCGGGG ATGGGGCTGA ATGCCTATTT CACCTTTGCC GTCGTTAAGG  1850

1860       1870       1880       1890       1900
ORF3        1851  .......... .......... .......... .......... ..........  1900
ORF2.SEQ    1851  .......... .......... .......... .......... ..........  1900
ORF1        1851  .......... .......... .......... .......... ..........  1900
PATENT.SEQ  1851  GTATGGGCTG CCTTGGCAGG TTGCGTTGGG TGCGGTGTTC ATCTCCGGTC  1900
```

FIG.8D

```
                       1910       1920       1930       1940       1950
ORF3         1901 ---------- ---------- ---------- ---------- ----------  1950
ORF2.SEQ     1901 ---------- ---------- -TTTTTAAAG TCAGGGAAAT GCTGTCAACG  1950
ORF1         1901 ---------- ---------- ---------- ---------- ----------  1950
PATENT.SEQ   1901 TGATTTTCAT CCTGTTCAGC TTTTTTAAAG TCAGGGAAAT GCTGTCAACG  1950

1960       1970       1980       1990       2000
ORF3         1951 ---------- ---------- ---------- ---------- ----------  2000
ORF2.SEQ     1951 CACTGCCTAT GGGTTTGAAA ATGTCGATTG CTGCCGGTAT CGGTTTGTTT  2000
ORF1         1951 ---------- ---------- ---------- ---------- ----------  2000
PATENT.SEQ   1951 CACTGCCTAT GGGTTTGAAA ATGTCGATTG CTGCCGGTAT CGGTTTGTTT  2000

2010       2020       2030       2040       2050
ORF3         2001 ---------- ---------- ---------- ---------- ----------  2050
ORF2.SEQ     2001 TTGGCACTGA TTTCCCTGAA AGGCGCAGGC CATTATCGTT GCCAATCCGG  2050
ORF1         2001 ---------- ---------- ---------- ---------- ----------  2050
PATENT.SEQ   2001 TTGGCACTGA TTTCCCTGAA AGGCGCAGGC CATTATCGTT GCCAATCCGG  2050

2060       2070       2080       2090       2100
ORF3         2051 ---------- ---------- ---------- ---------- ----------  2100
ORF2.SEQ     2051 CAACCTTGGT CGGTTTGGGC GATATTCATC AGCCGTCCGC GTTGTTGGCA  2100
ORF1         2051 ---------- ---------- ---------- ---------- ----------  2100
PATENT.SEQ   2051 CAACCTTGGT CGGTTTGGGC GATATTCATC AGCCGTCCGC GTTGTTGGCA  2100

2110       2120       2130       2140       2150
ORF3         2101 ---------- ---------- ---------- ---------- ----------  2150
ORF2.SEQ     2101 CTGTTCGGTT TTGCTATGGT GGTCGTATTG GGACATTTCC GCGTTCAAGG  2150
ORF1         2101 ---------- ---------- ---------- ---------- ----------  2150
PATENT.SEQ   2101 CTGTTCGGTT TTGCTATGGT GGTCGTATTG GGACATTTCC GCGTTCAAGG  2150

2160       2170       2180       2190       2200
ORF3         2151 ---------- ---------- ---------- ---------- ----------  2200
ORF2.SEQ     2151 CGCAACATCA TCACCATCTT GACCATTACC GTCATTGCCA GCCTGATGGG  2200
ORF1         2151 ---------- ---------- ---------- ---------- ----------  2200
PATENT.SEQ   2151 CGCAACATCA TCACCATCTT GACCATTACC GTCATTGCCA GCCTGATGGG  2200

2210       2220       2230       2240       2250
ORF3         2201 ---------- ---------- ---------- ---------- ----------  2250
ORF2.SEQ     2201 TTTGAATGAA TTTCACGGCA TCATCGGCGA AGTACCGAGC ATTGCGCCGA  2250
ORF1         2201 ---------- ---------- ---------- ---------- ----------  2250
PATENT.SEQ   2201 TTTGAATGAA TTTCACGGCA TCATCGGCGA AGTACCGAGC ATTGCGCCGA  2250

2260       2270       2280       2290       2300
ORF3         2251 ---------- ---------- ---------- ---------- ----------  2300
ORF2.SEQ     2251 CTTTTATGCA GATGGATTTT GAAGGCCTGT TTACCGTCAG CTGGTCAGTG  2300
ORF1         2251 ---------- ---------- ---------- ---------- ----------  2300
PATENT.SEQ   2251 CTTTTATGCA GATGGATTTT GAAGGCCTGT TTACCGTCAG CTGGTCAGTG  2300

2310       2320       2330       2340       2350
ORF3         2301 ---------- ---------- ---------- ---------- ----------  2350
ORF2.SEQ     2301 ATTTTCGTCT TCTTCTTGGT CGATCTATTT GACAGTACCG GAACGCTGGT  2350
ORF1         2301 ---------- ---------- ---------- ---------- ----------  2350
PATENT.SEQ   2301 ATTTTCGTCT TCTTCTTGGT CGATCTATTT GACAGTACCG GAACGCTGGT  2350
```

FIG.8E

```
                       2360       2370       2380       2390       2400
ORF3       2351   ---------- ---------- ---------- ---------- ----------  2400
ORF2.SEQ   2351   CGGCATATCC CACCGTGCCG GGCTGCTGGT GGACGGTAAG CTGCCCCGCC  2400
ORF1       2351   ---------- ---------- ---------- ---------- ----------  2400
PATENT.SEQ 2351   CGGCATATCC CACCGTGCCG GGCTGCTGGT GGACGGTAAG CTGCCCCGCC  2400

2410       2420       2430       2440       2450
ORF3       2401   ---------- ---------- ---------- ---------- ----------  2450
ORF2.SEQ   2401   TGAAACGCGC ACTGCTTGCA GACTCTACCG CCATTATGGC AGGTGCGGCT  2450
ORF1       2401   ---------- ---------- ---------- ---------- ----------  2450
PATENT.SEQ 2401   TGAAACGCGC ACTGCTTGCA GACTCTACCG CCATTATGGC AGGTGCGGCT  2450

2460       2470       2480       2490       2500
ORF3       2451   ---------- ---------- ---------- ---------- ----------  2500
ORF2.SEQ   2451   TTGGGTACTT CTTCCACCAC GCCTTATGTG GAAAGCGCGG CGGGCGTATC  2500
ORF1       2451   ---------- ---------- ---------- ---------- ----------  2500
PATENT.SEQ 2451   TTGGGTACTT CTTCCACCAC GCCTTATGTG GAAAGCGCGG CGGGCGTATC  2500

2510       2520       2530       2540       2550
ORF3       2501   ---------- ---------- ---------- ---------- ----------  2550
ORF2.SEQ   2501   GGCAGGCGGA CGGACCGGCC TGACGGCGGT TACCGTCGGC GTATTGATGC  2550
ORF1       2501   ---------- ---------- ---------- ---------- ----------  2550
PATENT.SEQ 2501   GGCAGGCGGA CGGACCGGCC TGACGGCGGT TACCGTCGGC GTATTGATGC  2550

2560       2570       2580       2590       2600
ORF3       2551   ---------- ---------- ---------- ---------- ----------  2600
ORF2.SEQ   2551   TCGCCTGCCT GATGTTTTCA CCTTTGGCGA AAAGTGTTCC CGCTTTTGGC  2600
ORF1       2551   ---------- ---------- ---------- ---------- ----------  2600
PATENT.SEQ 2551   TCGCCTGCCT GATGTTTTCA CCTTTGGCGA AAAGTGTTCC CGCTTTTGGC  2600

2610       2620       2630       2640       2650
ORF3       2601   ---------- ---------- ---------- ---------- ----------  2650
ORF2.SEQ   2601   ACCGCGCCCG CCCTGCTTTA TGTCGGCACG CAGATGCTCC GCAGTGCGAG  2650
ORF1       2601   ---------- ---------- ---------- ---------- ----------  2650
PATENT.SEQ 2601   ACCGCGCCCG CCCTGCTTTA TGTCGGCACG CAGATGCTCC GCAGTGCGAG  2650

2660       2670       2680       2690       2700
ORF3       2651   ---------- ---------- ---------- ---------- ----------  2700
ORF2.SEQ   2651   GGATATTGAT TGGGACGATA TGACGGAAGC CGCACCCGCA TTCCTGACCA  2700
ORF1       2651   ---------- ---------- ---------- ---------- ----------  2700
PATENT.SEQ 2651   GGATATTGAT TGGGACGATA TGACGGAAGC CGCACCCGCA TTCCTGACCA  2700

2710       2720       2730       2740       2750
ORF3       2701   ---------- ---------- ---------- ---------- ----------  2750
ORF2.SEQ   2701   TTGTCTTCAT GCCGTTTACC TATTCGATTG CAGACGGCAT CGCCTTCGGC  2750
ORF1       2701   ---------- ---------- ---------- ---------- ----------  2750
PATENT.SEQ 2701   TTGTCTTCAT GCCGTTTACC TATTCGATTG CAGACGGCAT CGCCTTCGGC  2750

2760       2770       2780       2790       2800
ORF3       2751   ---------- ---------- ---------- ---------- ----------  2800
ORF2.SEQ   2751   TTCATCAGCT ATGCCGTGGT TAAACTTTTA TGCCGCCGCA CCAAAGACGT  2800
ORF1       2751   ---------- ---------- ---------- ---------- ----------  2800
PATENT.SEQ 2751   TTCATCAGCT ATGCCGTGGT TAAACTTTTA TGCCGCCGCA CCAAAGACGT  2800

2810       2820       2830       2840       2850
ORF3       2801   ---------- ---------- ---------- ---------- ----------  2850
ORF2.SEQ   2801   TCCGCCTATG GAATGGGTTG TTGCCGTATT GTGGGCACTG AAATTCTGGT  2850
ORF1       2801   ---------- ---------- ---------- ---------- ----------  2850
PATENT.SEQ 2801   TCCGCCTATG GAATGGGTTG TTGCCGTATT GTGGGCACTG AAATTCTGGT  2850
```

FIG.8F

```
                          2860       2870       2880       2890       2900
ORF3         2851   .......... .......... .......... .......... ..........  2900
ORF2.SEQ     2851   ATTTGGGCTG ATTGATTCGA TATTAAAAAT .......... ..........  2900
ORF1         2851   .......... .......... .......... .......... ..........  2900
PATENT.SEQ   2851   ATTTGGGCTG ATTGATTCGA TATTAAAAAT GCCGTCTGAA AGGTTTTCAG  2900

2910       2920       2930       2940       2950
ORF3         2901   .......... .......... .......... .......... ..........  2950
ORF2.SEQ     2901   .......... .......... .......... .......... ..........  2950
ORF1         2901   .......... .......... .......... .......... ..........  2950
PATENT.SEQ   2901   ACGGCATTTT GTTTGCCGAT ATATTAATTT TTATTAAATT ATATAAAAAT  2950

2960       2970       2980       2990       3000
ORF3         2951   .......... .......... .......... .......... ..........  3000
ORF2.SEQ     2951   .......... .......... .......... .......... ..........  3000
ORF1         2951   .......... .......... .......... .......... ..........  3000
PATENT.SEQ   2951   CAAATACATA ATAAAATACA TCGGATTGCT TAAAAATAAT ACATTGTTTT  3000

3010       3020       3030       3040       3050
ORF3         3001   .......... .......... .......... .......... ..........  3050
ORF2.SEQ     3001   .......... .......... .......... .......... ..........  3050
ORF1         3001   .......... .......... .......... .......... ..........  3050
PATENT.SEQ   3001   TTATGTATAA AATATTTTAT AAGTTTTCAG GATTTGGATT ATTGAAAATT  3050

3060       3070       3080       3090       3100
ORF3         3051   .......... .......... .......... .......... ..........  3100
ORF2.SEQ     3051   .......... .......... .......... .......... ..........  3100
ORF1         3051   .......... .......... .......... .......... ..........  3100
PATENT.SEQ   3051   TTTCTTGATT TCCTGACAAT TTTATTGAAA CAAATAATTC AAAATTAATC  3100

3110       3120       3130       3140       3150
ORF3         3101   .......... .......... .......... .......... ..........  3150
ORF2.SEQ     3101   .......... .......... .......... .......... ..........  3150
ORF1         3101   .......... .......... .......... .......... ..........  3150
PATENT.SEQ   3101   TAGTTTAATC ATAGAATTAA AATAAAATAT TAAAATTATG TAATGAGTCT  3150

3160       3170       3180       3190       3200
ORF3         3151   .......... .......... .......... .......... ..........  3200
ORF2.SEQ     3151   .......... .......... .......... .......... ..........  3200
ORF1         3151   .......... .......... .......... .......... ..........  3200
PATENT.SEQ   3151   CCTTAAAAAT GTTTGACATT TTCAGTCTTG TGTTTTAGAT TATCGAAAAA  3200

3210       3220       3230       3240       3250
ORF3         3201   .......... .......... .......... .......... ..........  3250
ORF2.SEQ     3201   .......... .......... .......... .......... ..........  3250
ORF1         3201   .......... .......... .......... .......... ..........  3250
PATENT.SEQ   3201   TAAAACTACA TAACACTACA AAGGAATATT ACTATGAAAC CAATTCAGAT  3250

3260       3270       3280       3290       3300
ORF3         3251   .......... .......... .......... .......... ..........  3300
ORF2.SEQ     3251   .......... .......... .......... .......... ..........  3300
ORF1         3251   .......... .......... .......... .......... ..........  3300
PATENT.SEQ   3251   GTTTTCCCCT TTTCTGAATA ATCCCCTTGT TTTCTTCTTG TCTGCGGTTT  3300

3310       3320       3330       3340       3350
ORF3         3301   .......... .......... .......... .......... ..........  3350
ORF2.SEQ     3301   .......... .......... .......... .......... ..........  3350
ORF1         3301   .......... .......... .......... .......... ..........  3350
PATENT.SEQ   3301   TGCCGCATAA TTCCGAACGG TCTGCTGTTT TTCTTTGATT CGTTTTAAAT  3350
```

FIG.8G

```
                              3360       3370       3380       3390       3400
ORF3        3351   .......... .......... .......... -AATGATTGG ATTGGGATGC   3400
ORF2.SEQ    3351   .......... .......... .......... .......... ..........   3400
ORF1        3351   .......... .......... .......... .......... ..........   3400
PATENT.SEQ  3351   ATCAATAAGA TAATTTTTCC CATATATTTT TAATGATTGG ATTGGGATGC   3400

3410       3420       3430       3440       3450
ORF3        3401   CCGACGCGTC GGATGGCTGT GTTTTGCCGT CCGAATGTGA TGGAAGCCTG   3450
ORF2.SEQ    3401   .......... .......... .......... .......... ..........   3450
ORF1        3401   .......... .......... .......... .......... ..........   3450
PATENT.SEQ  3401   CCGACGCGTC GGATGGCTGT GTTTTGCCGT CCGAATGTGA TGGAAGCCTG   3450

3460       3470       3480       3490       3500
ORF3        3451   TCCATACTGA AAAAAAGTCT ATAAAGGAGA AATATGATGA GTCAACACTC   3500
ORF2.SEQ    3451   .......... .......... .......... .......... ..........   3500
ORF1        3451   .......... .......... .......... .......... ..........   3500
PATENT.SEQ  3451   TCCATACTGA AAAAAAGTCT ATAAAGGAGA AATATGATGA GTCAACACTC   3500

3510       3520       3530       3540       3550
ORF3        3501   TGCCGGAGCA CGTTTCCGCC AAGCCGTGAA AGAATCGAAT CCGCTTGCCG   3550
ORF2.SEQ    3501   .......... .......... .......... .......... ..........   3550
ORF1        3501   .......... .......... .......... .......... ..........   3550
PATENT.SEQ  3501   TGCCGGAGCA CGTTTCCGCC AAGCCGTGAA AGAATCGAAT CCGCTTGCCG   3550

3560       3570       3580       3590       3600
ORF3        3551   TCGCCGGTTG CGTCAATGCT TATTTTGCAC GATTGGCCAC CCAAAGCGGT   3600
ORF2.SEQ    3551   .......... .......... .......... .......... ..........   3600
ORF1        3551   .......... .......... .......... .......... ..........   3600
PATENT.SEQ  3551   TCGCCGGTTG CGTCAATGCT TATTTTGCAC GATTGGCCAC CCAAAGCGGT   3600

3610       3620       3630       3640       3650
ORF3        3601   TTCAAAGCCA TCTATCTGTC TGGCGGCGGC GTGGCAGCCT GTTCTTGCGG   3650
ORF2.SEQ    3601   .......... .......... .......... .......... ..........   3650
ORF1        3601   .......... .......... .......... .......... ..........   3650
PATENT.SEQ  3601   TTCAAAGCCA TCTATCTGTC TGGCGGCGGC GTGGCAGCCT GTTCTTGCGG   3650

3660       3670       3680       3690       3700
ORF3        3651   TATCCCTGAT TTGGGCATTA CCACAATGGA AGATGTGCTG ATCGACGCAC   3700
ORF2.SEQ    3651   .......... .......... .......... .......... ..........   3700
ORF1        3651   .......... .......... .......... .......... ..........   3700
PATENT.SEQ  3651   TATCCCTGAT TTGGGCATTA CCACAATGGA AGATGTGCTG ATCGACGCAC   3700

3710       3720       3730       3740       3750
ORF3        3701   GACGCATTAC GGACAACGTG GATNCGCCTC TGCTGGTGGA CATCGATGTG   3750
ORF2.SEQ    3701   .......... .......... .......... .......... ..........   3750
ORF1        3701   .......... .......... .......... .......... ..........   3750
PATENT.SEQ  3701   GACGCATTAC GGACAACGTG GATNCGCCTC TGCTGGTGGA CATCGATGTG   3750

3760       3770       3780       3790       3800
ORF3        3751   GGTTGGGGCG GTGCATTCAA TATTGCCCGT ACCATTCGCA ACTTTGAACG   3800
ORF2.SEQ    3751   .......... .......... .......... .......... ..........   3800
ORF1        3751   .......... .......... .......... .......... ..........   3800
PATENT.SEQ  3751   GGTTGGGGCG GTGCATTCAA TATTGCCCGT ACCATTCGCA ACTTTGAACG   3800

3810       3820       3830       3840       3850
ORF3        3801   CGCCGGTGTT GCAGCGGTTC ACATCGAAGA TCAGGTA--- ..........   3850
ORF2.SEQ    3801   .......... .......... .......... .......... ..........   3850
ORF1        3801   .......... .......... .......... .......... ..........   3850
PATENT.SEQ  3801   CGCCGGTGTT GCAGCGGTTC ACATCGAAGA TCAGGTAGCG CAAAAACGCT   3850
```

FIG.8H

```
               3860       3870       3880       3890       3900
ORF3       3851 ---------- ---------- ---------- ---------- ----------  3900
ORF2.SEQ   3851 ---------- ---------- ---------- ---------- ----------  3900
ORF1       3851 ---------- ---------- ---------- ---------- ----------  3900
PATENT.SEQ 3851 GCGGTCACCG TCCGAACAAA GCCATTGTTA TCTNAAGATG NAATGGTCGA  3900

3910       3920       3930       3940       3950
ORF3       3901 ---------- ---------- ---------- ---------- ----------  3950
ORF2.SEQ   3901 ---------- ---------- ---------- ---------- ----------  3950
ORF1       3901 ---------- ---------- ---------- ---------- ----------  3950
PATENT.SEQ 3901 CCGTATCAAA GCTGCCGTAG ATGCGCGCGT TGNTGNGAAC TTCGTGATTA  3950

3960       3970       3980       3990       4000
ORF3       3951 ---------- ---------- ---------- ---------- ----------  4000
ORF2.SEQ   3951 ---------- ---------- ---------- ---------- ----------  4000
ORF1       3951 ---------- ---------- ---------- ---------- ----------  4000
PATENT.SEQ 3951 TGGCGCGTAC CGATGCGCTG GCGGTAGAAG GTTTGGATGC CGCTATCGAA  4000

4010       4020       4030       4040       4050
ORF3       4001 ---------- ---------- ---------- ---------- ----------  4050
ORF2.SEQ   4001 ---------- ---------- ---------- ---------- ----------  4050
ORF1       4001 ---------- ---------- ---------- ---------- ----------  4050
PATENT.SEQ 4001 CGCGCCCAAG CTTGTGTCGA AAGCCGGTGC GGACATGATT TTCCCTGAAG  4050

4060       4070       4080       4090       4100
ORF3       4051 ---------- ---------- ---------- ---------- ----------  4100
ORF2.SEQ   4051 ---------- ---------- ---------- ---------- ----------  4100
ORF1       4051 ---------- ---------- ---------- ---------- ----------  4100
PATENT.SEQ 4051 CCATGACCGA TTTGAACATG TACCGCCAAT TTGCAGATGC GGTGAAAGTG  4100

4110       4120       4130       4140       4150
ORF3       4101 ---------- ---------- ---------- ---------- ----------  4150
ORF2.SEQ   4101 ---------- ---------- ---------- ---------- ----------  4150
ORF1       4101 ---------- ---------- ---------- ---------- ----------  4150
PATENT.SEQ 4101 CGTGTTGGCG AACATTACCG AGTTTGGTTC CACTCCGCTT TATACCCAAA  4150

4160       4170       4180       4190       4200
ORF3       4151 ---------- ---------- ---------- ---------- ----------  4200
ORF2.SEQ   4151 ---------- ---------- ---------- ---------- ----------  4200
ORF1       4151 ---------- ---------- ---------- ---------- ----------  4200
PATENT.SEQ 4151 GCGAGCTGGC TGAAAACGGC GTGTCGCTGG TGCTGTATCC GCTGTCATCG  4200

4210       4220       4230       4240       4250
ORF3       4201 ---------- ---------- ---------- ---------- ----------  4250
ORF2.SEQ   4201 ---------- ---------- ---------- ---------- ----------  4250
ORF1       4201 ---------- ---------- ---------- ---------- ----------  4250
PATENT.SEQ 4201 TTCCGTGCAG CAAGCAAAGC CGCTCTGAAT GTTTACGAAG CGATTATGCG  4250

4260       4270       4280       4290       4300
ORF3       4251 ---------- ---------- ---------- ---------- ----------  4300
ORF2.SEQ   4251 ---------- ---------- ---------- ---------- ----------  4300
ORF1       4251 ---------- ---------- ---------- ---------- ----------  4300
PATENT.SEQ 4251 CGATGGCACT CAGGCGGCGG TGGTGGACAG TATGCAAACC CGTGCCGAGC  4300
```

FIG. 8I

|            |      | 4310       | 4320       | 4330       | 4340       | 4350       |      |
|------------|------|------------|------------|------------|------------|------------|------|
| ORF3       | 4301 | ·········· | ·········· | ·········· | ·········· | ·········· | 4350 |
| ORF2.SEQ   | 4301 | ·········· | ·········· | ·········· | ·········· | ·········· | 4350 |
| ORF1       | 4301 | ·········· | ·········· | ·········· | ·········· | ·········· | 4350 |
| PATENT.SEQ | 4301 | TGTACGAGCA | TCTGAACTAT | CATGCCTTCG | AGCAAAAACT | GGATAAATTG | 4350 |

|            |      | 4360       | 4370       | 4380       | 4390       | 4400       |      |
|------------|------|------------|------------|------------|------------|------------|------|
| ORF3       | 4351 | ·········· | ·········· | ·········· | ·········· | ·········· | 4400 |
| ORF2.SEQ   | 4351 | ·········· | ·········· | ·········· | ·········· | ·········· | 4400 |
| ORF1       | 4351 | ·········· | ·········· | ·········· | ·········· | ·········· | 4400 |
| PATENT.SEQ | 4351 | TTTCAAAAAT | GATTTACCGC | TTTCAGACGG | TCTTTCAACA | AATCCGCATC | 4400 |

|            |      | 4410       | 4420       | 4430       | 4440       | 4450       |      |
|------------|------|------------|------------|------------|------------|------------|------|
| ORF3       | 4401 | ·········· | ·········· | ·········· | ·········· | ·········· | 4450 |
| ORF2.SEQ   | 4401 | ·········· | ·········· | ·········· | ·········· | ·········· | 4450 |
| ORF1       | 4401 | ·········· | ·········· | ·········· | ·········· | ·········· | 4450 |
| PATENT.SEQ | 4401 | GGTCGTCTGA | AAACCCGAAA | CCCATAAAAA | CACAAAGGAG | AAATACCATG | 4450 |

|            |      | 4460       | 4470       | 4480       | 4490       | 4500       |      |
|------------|------|------------|------------|------------|------------|------------|------|
| ORF3       | 4451 | ·········· | ·········· | ·········· | ·········· | ·········· | 4500 |
| ORF2.SEQ   | 4451 | ·········· | ·········· | ·········· | ·········· | ·········· | 4500 |
| ORF1       | 4451 | ·········· | ·········· | ·········· | ·········· | ·········· | 4500 |
| PATENT.SEQ | 4451 | ACTGAAACTA | CTCAAACCCC | GACCTTCAAA | CCTAAGAAAT | CCGTTGCGCT | 4500 |

|            |      | 4510       | 4520       | 4530       | 4540       | 4550       |      |
|------------|------|------------|------------|------------|------------|------------|------|
| ORF3       | 4501 | ·········· | ·········· | ·········· | ·········· | ·········· | 4550 |
| ORF2.SEQ   | 4501 | ·········· | ·········· | ·········· | ·········· | ·········· | 4550 |
| ORF1       | 4501 | ·········· | ·········· | ·········· | ·········· | ·········· | 4550 |
| PATENT.SEQ | 4501 | TTCAGGCGTT | GCGGCCGGTA | ATACCGCTTT | GTGTACCGTT | GGCCGCACCC | 4550 |

|            |      | 4560       | 4570       | 4580       | 4590       | 4600       |      |
|------------|------|------------|------------|------------|------------|------------|------|
| ORF3       | 4551 | ·········· | ·········· | ·········· | ·········· | ·········· | 4600 |
| ORF2.SEQ   | 4551 | ·········· | ·········· | ·········· | ·········· | ·········· | 4600 |
| ORF1       | 4551 | ·········· | ·········· | ·········· | ·········· | ·········· | 4600 |
| PATENT.SEQ | 4551 | GGCAACGATT | TGGAGCTATC | GCGGTTACGA | CATCTTGGAT | TTGGGCACAA | 4600 |

|            |      | 4610       | 4620       | 4630       | 4640       | 4650       |      |
|------------|------|------------|------------|------------|------------|------------|------|
| ORF3       | 4601 | ·········· | ·········· | ·········· | ·········· | ·········· | 4650 |
| ORF2.SEQ   | 4601 | ·········· | ·········· | ·········· | ·········· | ·········· | 4650 |
| ORF1       | 4601 | ·········· | ·········· | ·········· | ·········· | ·········· | 4650 |
| PATENT.SEQ | 4601 | AAATGCGTTT | GAAGAAGTAG | CCCACCTGCT | GATTCACGGT | CATCTGCCCA | 4650 |

|            |      | 4660       | 4670       | 4680       | 4690       | 4700       |      |
|------------|------|------------|------------|------------|------------|------------|------|
| ORF3       | 4651 | ·········· | ·········· | ·········· | ·········· | ·········· | 4700 |
| ORF2.SEQ   | 4651 | ·········· | ·········· | ·········· | ·········· | ·········· | 4700 |
| ORF1       | 4651 | ·········· | ·········· | ·········· | ·········· | ·········· | 4700 |
| PATENT.SEQ | 4651 | ACAAATTCGA | CGTGGAAGCT | TATAAAAGGA | AGCTCAAATC | CATGCGCGGC | 4700 |

|            |      | 4710       | 4720       | 4730       | 4740       | 4750       |      |
|------------|------|------------|------------|------------|------------|------------|------|
| ORF3       | 4701 | ·········· | ·········· | ·········· | ·········· | ·········· | 4750 |
| ORF2.SEQ   | 4701 | ·········· | ·········· | ·········· | ·········· | ·········· | 4750 |
| ORF1       | 4701 | ·········· | ·········· | ·········· | ·········· | ·········· | 4750 |
| PATENT.SEQ | 4701 | CTGCCTATCC | GTGTATTAAA | GTTTTGGGAA | AGCCTGCCTG | CACATACCCA | 4750 |

|            |      | 4760       | 4770       | 4780       | 4790       | 4800       |      |
|------------|------|------------|------------|------------|------------|------------|------|
| ORF3       | 4751 | ·········· | ·········· | ·········· | ·········· | ·········· | 4800 |
| ORF2.SEQ   | 4751 | ·········· | ·········· | ·········· | ·········· | ·········· | 4800 |
| ORF1       | 4751 | ·········· | ·········· | ·········· | ·········· | ·········· | 4800 |
| PATENT.SEQ | 4751 | TCCGGATGGA | CGGTAATGGC | GTACCGGCGG | TATCCATGCT | GGGCTGCGTT | 4800 |

FIG.8J

```
                    4810       4820       4830       4840       4850
ORF3        4801   ---------- ---------- ---------- ---------- ----------   4850
ORF2.SEQ    4801   ---------- ---------- ---------- ---------- ----------   4850
ORF1        4801   ---------- ---------- ---------- ---------- ----------   4850
PATENT.SEQ  4801   CATCCCGAAC GTGAAAGCCA TCCCGGAAAG TGAAGCGCGC GACATCGCCG   4850

4860       4870       4880       4890       4900
ORF3        4851   ---------- ---------- ---------- ---------- ----------   4900
ORF2.SEQ    4851   ---------- ---------- ---------- ---------- ----------   4900
ORF1        4851   ---------- ---------- ---------- ---------- ----------   4900
PATENT.SEQ  4851   ACAAACTGAT TGCAGCCTCG GAGCCTCCTG CTGTACTNGG TATCAATATC   4900

4910       4920       4930       4940       4950
ORF3        4901   ---------- ---------- ---------- ---------- ----------   4950
ORF2.SEQ    4901   ---------- ---------- ---------- ---------- ----------   4950
ORF1        4901   ---------- ---------- ---------- ---------- ----------   4950
PATENT.SEQ  4901   GCACAACGGC AAACGCATTG AGTTGAAGCG ACGAGAGACA TCGGCGGTCA   4950

4960       4970       4980       4990       5000
ORF3        4951   ---------- ---------- ---------- ---------- ----------   5000
ORF2.SEQ    4951   ---------- ---------- ---------- ---------- ----------   5000
ORF1        4951   ---------- ---------- ---------- ---------- ----------   5000
PATENT.SEQ  4951   TTTCCTGCAA CTGTTNCACG GCAACGCCCA AGCGATCACA CATCAAAGCC   5000

5010       5020       5030       5040       5050
ORF3        5001   ---------- ---------- ---------- ---------- ----------   5050
ORF2.SEQ    5001   ---------- ---------- ---------- ---------- ----------   5050
ORF1        5001   ---------- ---------- ---------- ---------- ----------   5050
PATENT.SEQ  5001   ATGCACGTTT CACTGATTCT GTATGCGAAC ACGAGTTCAA CGTTCTACCT   5050

5060       5070       5080       5090       5100
ORF3        5051   ---------- ---------- ---------- ---------- ----------   5100
ORF2.SEQ    5051   ---------- ---------- ---------- ---------- ----------   5100
ORF1        5051   ---------- ---------- ---------- ---------- ----------   5100
PATENT.SEQ  5051   TTACCGTTTG CCGTTCTTCT GGTCGGTTCT AGCCCTGTAA AAAGAGAAGG   5100

5110       5120       5130       5140       5150
ORF3        5101   ---------- ---------- ---------- ---------- ----------   5150
ORF2.SEQ    5101   ---------- ---------- ---------- ---------- ----------   5150
ORF1        5101   ---------- ---------- ---------- ---------- ----------   5150
PATENT.SEQ  5101   TTGTTAGCTG GCGAAGGTTT GCAGCCGTTA CAGTTTCCCG CGTTATAGCG   5150

5160       5170       5180       5190       5200
ORF3        5151   ---------- ---------- ---------- ---------- ----------   5200
ORF2.SEQ    5151   ---------- ---------- ---------- ---------- ----------   5200
ORF1        5151   ---------- ---------- ---------- ---------- ----------   5200
PATENT.SEQ  5151   GCCAAGAAAC GAGTTTGGCG CACGGTGAGA ATTACCTGTT GCAACGCCCC   5200

5210       5220       5230       5240       5250
ORF3        5201   ---------- ---------- ---------- ---------- ----------   5250
ORF2.SEQ    5201   ---------- ---------- ---------- ---------- ----------   5250
ORF1        5201   ---------- ---------- ---------- ---------- ----------   5250
PATENT.SEQ  5201   AGCCTTTACC ATATGTGGGC CTACTGGCTT NGGCTAGTGC TAAGAAACGC   5250
```

FIG.8K

```
                  5260       5270       5280       5290       5300
ORF3        5251  ---------- ---------- ---------- ---------- ----------  5300
ORF2.SEQ    5251  ---------- ---------- ---------- ---------- ----------  5300
ORF1        5251  ---------- ---------- ---------- ---------- ----------  5300
PATENT.SEQ  5251  GGCTATGCTA GCGCCTACAT GCCGAGTGAC GAGCGTNACG CCTACGCAAA  5300

5310       5320       5330       5340       5350
ORF3        5301  ---------- ---------- ---------- ---------- ----------  5350
ORF2.SEQ    5301  ---------- ---------- ---------- ---------- ----------  5350
ORF1        5301  ---------- ---------- ---------- ---------- ----------  5350
PATENT.SEQ  5301  ACTTATACGC ATTTCGGGAA GCCAANCGCT GGCGGCACAA AGCCTGGATA  5350

5360       5370       5380       5390       5400
ORF3        5351  ---------- ---------- ---------- ---------- ----------  5400
ORF2.SEQ    5351  ---------- ---------- ---------- ---------- ----------  5400
ORF1        5351  ---------- ---------- ---------- ---------- ----------  5400
PATENT.SEQ  5351  GTTGTGCGGC TAACGNGGCC ATTACGACCT CATGTATAGT CCTCTGACAT  5400

5410       5420       5430       5440       5450
ORF3        5401  ---------- ---------- ---------- ---------- ----------  5450
ORF2.SEQ    5401  ---------- ---------- ---------- ---------- ----------  5450
ORF1        5401  ---------- ---------- ---------- ---------- ----------  5450
PATENT.SEQ  5401  GGCGCTANTT GCGCCC---- ---------- ---------- ----------  5450
```

INVASION ASSOCIATED GENES FROM *NEISSERIA MENINGITIDIS* SEROGROUP B

This is a 35 U.S.C. § 371 national phase application of international application PCT/U.S.97/19424, filed Oct. 24, 1997, which claims priority, under 35 U.S.C. § 119(e), of provisional application U.S. application Ser. No. 60/030,432, filed Oct. 24, 1996, the entire contents; of which are incorporated herein by reference.

FIELD OF THE INVENTION

The invention relates to new genes isolated from *Neisseria meningitidis*. Isolated nucleic acids, probes, expression cassettes, polypeptides, antibodies, immunogenic compositions, antisense nucleic acids, amplification mixtures and new invasion deficient strains of *Neisseria meningitidis*. The invention also relates to methods of detecting Neisseria meningitidis and *Neisseria meningitidis* nucleic acids, and to methods of inhibiting the invasion of mammalian cells by *Neisseria meningitidis*.

BACKGROUND OF THE INVENTION

*Neisseria meningitidis*, a Gram-negative encapsulated diplococcus, is an obligate human pathogen and the causative agent of meningococcal meningitis, one of the most devastating forms of meningitis. These bacteria are isolated from humans worldwide and can cause sporadic and epidemic disease. Person-to-person transfer of *N. meningitidis* occurs mainly via the airborne route, and is particularly a problem in places where people are in close quarters, such as prisons, military camps, school class rooms, and day care centers. At any one time, between 2 and 10% of individuals in the population carry this organism asymptomatically (Greenfield, S., et al. (1971), *J. Infec. Dis.*, 123:67–73; Moore, P. S., et al. (November 1994), *Scientific American*, p38–45; Romero, J. D. et al. (1994), *Clinical Microbiology Review*, 7:559–575). With such a high carrier rate, the threat or potential for outbreaks or epidemics is always present. Although significant advances have been made in the area of the pathogenesis of the organism, there is much to be learned about the genetics and cell biology of the host-parasite interaction.

Understanding the mechanism(s) of attachment and invasion is one of the most important aspects in *N. meningitidis* disease. In order to cause disease, meningacocci must survive and colonize the mucosa of the nasopharynx, pass through these tissue into the bloodstream replicate to large numbers in the blood, cross the blood-brain barrier and multiply in the cerebrospinal fluid (CFS) where they cause inflammation of the meninges. Various models have been used in order to mimic the events that take place during infection in humans. Mouse models (Miller, C. P. (1933), *Science*, 78:340–341; Holbein, B. E. (1981), *Can. J. Microbiol.*, 27:738–741; Salit, I. E. (1984), *Can. J. Microbiol.*, 30:1022–1029), human nasopharyngeal organ culture (Stephens, D. S., et al. (1991), *Rev Infect Dis.*, 13:22–33), chick embryo (Buddingh, G. J. et al. (1987), *Science*, 86:20.21; Pine, L., et al., *Micrbiol. Lett.*, 130:37–44), and tissue culture monolayer and bilayer systems (Birkness, K. A., et al. (1995), *Infect. Immun.*, 63:402–409) represent some of the models commonly used to study virulence of *N. meningitidis*.

The organ culture system has been used successfully to assess the attachment and invasion properties of various *N. meningitidis* strains (Salit, I. E. (1984), *Can. J. Microbiol.*, 30:1022–1029).

Designated by serogroup, serological classification of *N. meningitidis* is based on the capsular polysaccharide composition of the particular strain. Among the meningococci there are at least thirteen different serogroups: A, B, C, 29-E, H, I, X, L, W135, X, Y and Z. Of these serogroups, A, B and C comprise over 90% of the strains isolated from patients afflicted with meningococcal meningitis (Poolman, J. T., et al. (1995), *Infectious Agents and Disease*, 4:13–28). The nature of the capsule in serogroups A and C has led to the development of useful vaccines against these serogroups. However, the serogroup B capsular polysaccharide does not induce protection in humans. Many laboratories around the world are concentrating their efforts on the study and characterization of epitopes from various membrane and other extracellular factors for use as vaccine candidates. Some of the most common non-capsule factors in such studies include a number of outer membrane proteins (OMP) such as class 1 (Por A, a cation Specific porin), class 2 or 3 (Pot B, an anion specific protein) and to a lesser extent class 4 and class 5 OMPs (Rmp, and Opc and Opa opacity associated proteins, respectively). While class 5 Opc and Opa OMPs have been shown to play roles in the invasion of epithelial cells (Virji, M., et al. (1992), *Mol. Microbiol.*, 6;2786–96) due to their antigenic and phase variability (Aho, E. L.; et al. (1991), *Mol. Microbiol.*, 5:1429–37), they are not considered to be good vaccine candidates.

Class 1 OMPs appear to be good candidates for vaccine studies since these proteins have been shown to induce protective immunity. Evaluation of various non-capsular antigens as potential vaccine candidates in in vitro bactericidal assays and an infant rat model revealed that class 1 OMP had the highest protective capacity compared to factors such as LPS and class 2/3 OMPs (Saukkonen, K., et al. (1989), *Vaccine*, 7:325–328). However, preliminary data from vaccine trial studies suggests that these factors do not elicit a complete immune response, especially in children (Romero. J. D. et al. (1994), *Clinical Microbiology Review*, 7:559–575; Poolman, J. T., et al. (1995), *Infectious Agents and Disease*, 4:13–28). The development of fusion or hybrid genes containing epitopes from class 1 OMP show great promise as vaccine candidates (Van der Ley, P., et al. (1992), *Infect. Immun.*, 60:3156–3161; Van der Ley, P., et al. (1993), *Infect. Immun.*, 61:4217–4224). However, these hybrids do not elicit protection in infants, and the immunity induced is type specific and very short-lived (Poolman, J. T., et al: (1995), *Infectious Agents and Disease*, 4:13–28). Far these and other reasons, it is or importance to identify alternative serogroup B vaccine antigens. Initial attachment and invasion by the pathogen is critical to the disease process. If mucosal immunity can be derived against these bacterial factors, the disease process and the carrier state can be prevented. The present invention provides these and other features.

SUMMARY OF THE INVENTION

The invention provides nucleic acids and encoded polypeptides associated with invasion of *Neisseria meningitidis*. The polypeptides are used as diagnostic reagents as immunogenic reagents; and as components of vaccines. The nucleic acids are used as diagnostic reagents, as components of vectors and vaccines, and to encode the polypeptides of the invention. The invention also provides strains of *Neisseria meningitidis* which have an invasion deficient phenotype.

In one embodiment, the invention provides isolated nucleic acids encoding the polypeptides of the invention, including ORF 1 (SEQ ID NO:2), ORF 2 (ORF2 a (SEQ ID NO:4) and ORF2b (SEQ ID NO:5), two separate embodiments depending on alternate start sites for the ORF2 polypeptide), ORF 3 (SEQ ID NO:7) and, conservatively modified variations of each of the polypeptides. Exemplar nucleic acids include Seq 1 (SEQ ID NO:1), Seq 2 (SEQ ID NO:3), and Seq 3 (SEQ ID NO:7) (see, FIGS. 5, 6, and 7 respectively). Other nucleic acids encoding the same polypeptides include those with silent codon substitutions relative to Seq 1 (SEQ ID NO:1), Seq 2 (SEQ ID NO:3) for Seq 3 (SEQ ID NO:6); as well as conservatively modified variations thereof.

Isolated nucleic acids which hybridize under stringent conditions to the exemplar nucleic acids Seq 1 (SEQ ID NO:1), Seq 2 (SEQ ID NO:3), or Seq 3 (SEQ ID NO:6) are also provided. For example, a complementary nucleic acid to a sequence provided by Seq 1 (SEQ ID NO:1), Seq 2 (SEQ ID NO:3), or Seq 3 (SEQ ID NO:6) hybridizes to Seq 1 (SEQ ID NO:1), Seq 2 (SEQ ID NO:3), or Seq 3 (SEQ ID NO:6), respectively. Nucleic acids which include substantial subsequences complementary to Seq 1 (SEQ ID NO:1), Seq 2 (SEQ ID NO:3), or Seq 3 (SEQ ID NO:6) also hybridize to Seq 1 (SEQ ID NO:1), Seq 2 (SEQ ID NO:3), or Seq 3 (SEQ ID NO:6), respectively.

Isolated nucleic acids which hybridize under stringent conditions to Seq 4 (SEQ ID NO:8) are provided. Seq 4 (SEQ ID NO:8) is a genomic sequence which encodes Seq 1 (SEQ ID NO:1), Seq 2 (SEQ ID NO:3), and Seq 3 (SEQ ID NO:6). Thus, complementary nucleic acids to sequences provided by Seq 1 (SEQ ID NO:1), Seq 2 (SEQ ID NO:3), Seq 3 (SEQ ID NO:6), or Seq 4 (SEQ ID NO:8) all hybridize to Seq 4 (SEQ ID NO:8) under stringent conditions. Similarly, nucleic acids which include substantial subsequences of Seq 1 (SEQ ID NO:1), Seq 2 (SEQ ID NO:3), Seq 3 (SEQ ID NO:6) or Seq 4 (SEQ ID NO:8) also hybridize to Seq 4 (SEQ ID NO:8). The isolated nucleic acids are optionally vector nucleic acids which comprise a transcription cassette. The transcription cassette optionally encodes a polypeptide. Typically, the portion of the transcription cassette which encodes the polypeptide hybridizes to Seq 4 (SEQ ID NO:8) under stringent conditions. Upon transduction of the transcription cassette into a cell, an mRNA which hybridizes to Seq 4 (SEQ ID NO:8) under stringent conditions is produced. The mRNA is translated in the cell into a polypeptide such as the ORF 1 (SEQ ID NO:2), ORF 2a (SEQ ID NO:4), ORF 2b (SEQ ID NO:5) or ORF 3 (SEQ ID NO:7) polypeptides.

Polypeptides encoded by nucleic acids which hybridize under stringent conditions to Seq 4 (SEQ ID NO:8), including Seq 1 (SEQ ID NO:1), Seq 2 (SEQ ID NO:3), Seq 3 (SEQ ID NO:7) are provided herein. Exemplar polypeptides include ORF 1 (SEQ ID NO:1), ORF 2a (SEQ ID NO:4), ORF 2b (SEQ ID NO:5), or ORF 3 (SEQ ID NO:6).

Full length polypeptides of the invention, or antigenic epitopes derived from the full length polypeptides of the invention are optionally present in immunogenic compositions. The antigenic epitopes are optionally incorporated into fusion proteins which optionally include antigenic epitopes from related or unrelated proteins. The antigenic epitopes are optionally expressed on the surface or antigenic viral vectors.

The immunogenic compositions optionally comprise components to enhance immunogenicity, Such as an adjuvant. The compositions optionally include pharmaceutically acceptable excipients. When administered to a mammal, the immunogenic compositions optionally provide an immune response against antigenic epitopes which are included In the immunogenic compositions. In one preferred embodiment, administration of the immunogenic composition of the invention to a mammal inhibits invasion of the cells of the mammal by *Neisseria meningitidis*.

Antibodies which specifically bind to the polypeptides of the invention are provided. In a preferred embodiment, the antibodies bind to a polypeptide such as ORF 1 (SEQ ID NO:2), ORF 2a (SEQ ID NO:4), ORF 2b (SEQ ID NO:5), or ORF 3 (SEQ ID NO:7); without binding to the *E coli* FtsZ protein, or to the *E coli* UNK protein. Typically, the antibodies specifically bind to the ORF 1 (SEQ ID NO:2), ORF 2a (SEQ ID NO:4), ORF 2b (SEQ ID NO:5), or ORF 3 (SEQ ID NO:7) proteins.

The invention provides isolated *Neisseria meningitidis* diplococcus. The diplococcus has a reduced ability to invade tissue culture epithelial cells in vitro as compared to a wild-type *Neisseria meningitidis* diplococcus and the genome of the isolated *Neisseria meningitidis* diplococcus has a modification in the region of the genome corresponding to Seq 4 (SEQ ID NO:8). In one embodiment, the isolated *Neisseria meningitidis* diplococcus comprises a transposon insertion in the region of the genome corresponding to Seq 4 (SEQ ID NO:8).

The invention provides a variety of assays for detecting *Neisseria meningitidis*, including PCR assays, northern blots, Southern bloc, western blots and ELISA assays. For example, the invention provides PCR reaction mixtures using template nucleic acids which hybridize to Seq 4 (SEQ ID NO:8) under stringent conditions. The mixture has a primer pair which hybridizes to the template nucleic acid, wherein the primers, when hybridized to the template, serve as initiation sites for primer extension by a thermostable polymerase such as taq or vent DNA polymerase. The products of PCR amplification are detected by detecting the amplified nucleic acid products (amplicons) of the PCR reaction.

In several methods relying on nucleic acid hybridization, the detection of a *Neisseria meningitidis* nucleic acid in a biological sample is performed by contacting a probe nucleic acid to the sample and detecting binding of the nucleic acid to the *Neisseria meningitidis* nucleic acid. The probe hybridizes to Seq 4 (SEQ ID NO:8), or the complement thereof. Many assay formats are appropriate, including northern and Southern blotting.

In one embodiment, the invention provides methods of inhibiting the invasion of a mammalian cell by Neisseria meningitidis by expressing an anti-sense RNA molecule in the mammalian cell. The antisense RNA molecule hybridizes to a nucleic acid which hybridizes under stringent conditions to a nucleic acid encoded by Seq 1 (SEQ ID NO:1), Seq 2 (SEQ ID NO:3), Seq 3 (SEQ ID NO:7), or Seq 4 (SEQ ID NO:8). Such anti sense molecules optionally comprise catalytic RNA ribonuclease domains, such as those derived from a ribozyme.

BRIEF DESCRIPTION OF THE DRAWING

FIGS. 4A–4E show the sequence of Seq 4 (SEQ ID NO:8), with ribosome binding sites (RBS), start sites and stop sites for ORF 1 (SEQ ID NO:7), ORF 2a (SEQ ID NO:4), ORF 2b (SEQ ID NO:5), and ORF 3 (SEQ ID NO:2).

FIGS. 5A–5B show the sequence of Seq 1 (SEQ ID NO:1) (see the nucleic acid sequence of the open reading frame ) and the corresponding amino acid sequence ORF 1 (SEQ ID NO:2).

DEFINITIONS

Figure 1:
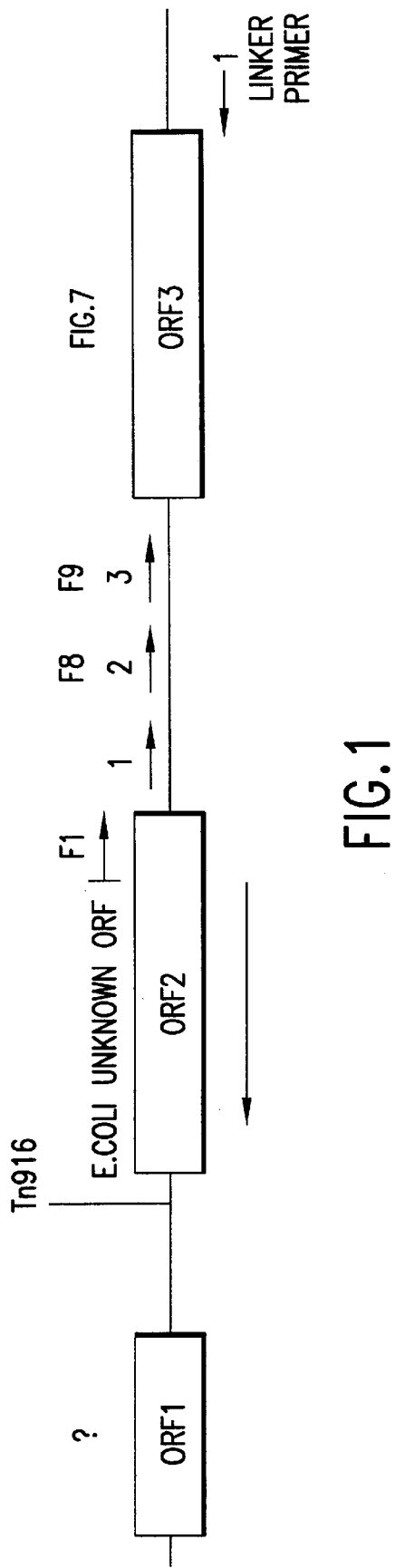
FIG. 1 is a schematic of the region from Neisseria meningitidis surrounding the Tn916 transposon from VVV6.
Figure 2:
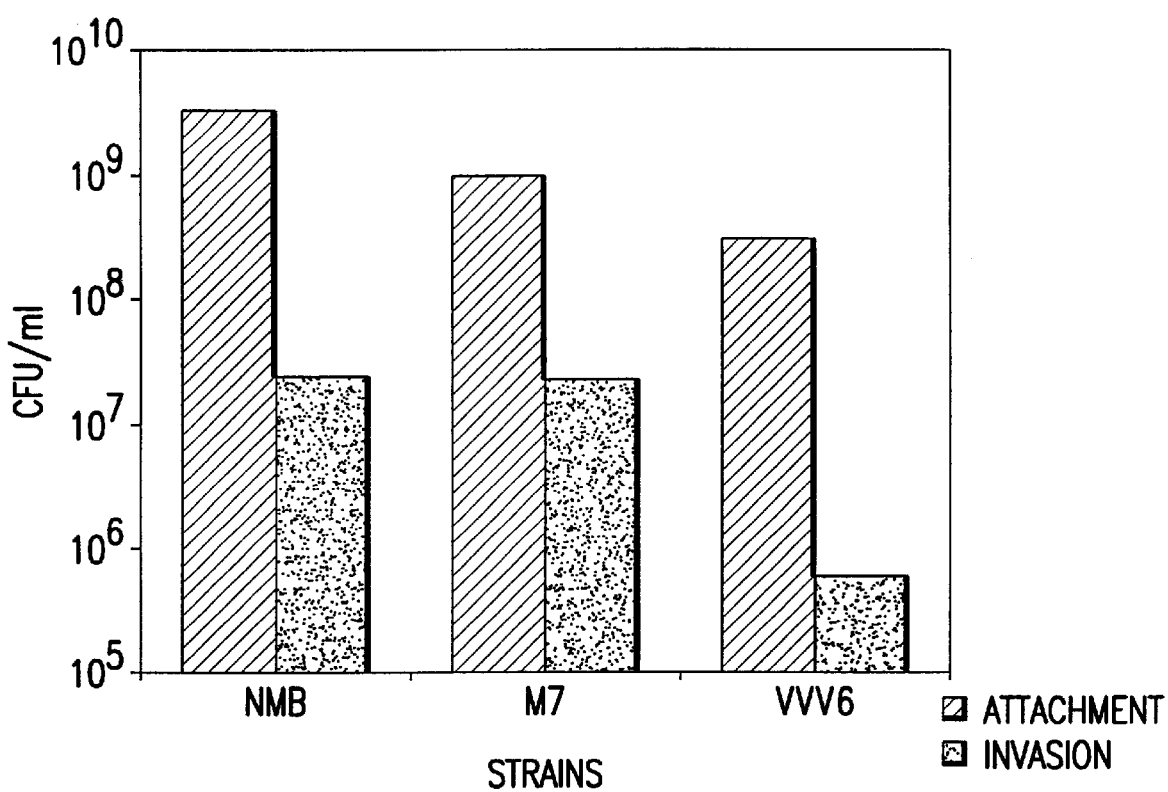
FIG. 2 is a graph of the attachment-invasion assay performed on the HEC-1-B cell line.
Figure 3:
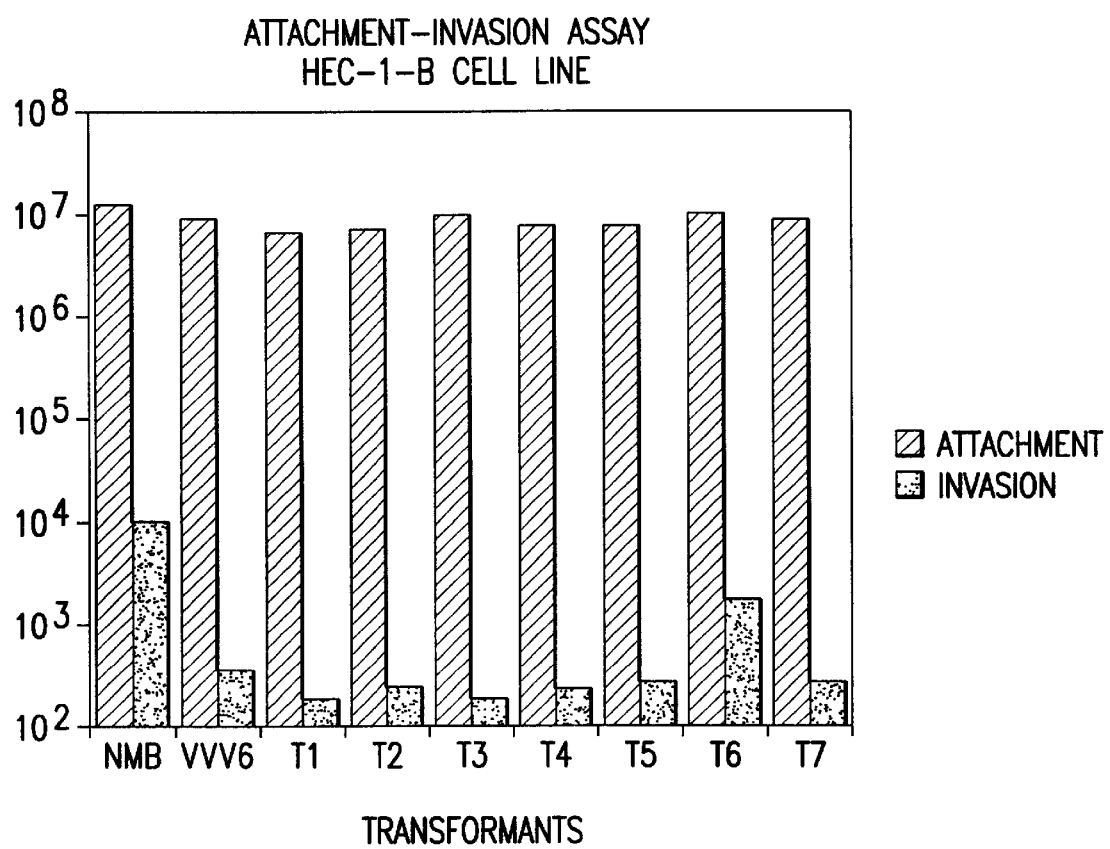
FIG. 3 is a graph of the attachment-invasion assay performed on the HEC-1-B cell line with VVV6 and related recombinant *Neisseria meningitidis*.

Unless defined otherwise, all technical and scientific terms used herein have the same meaning as commonly understood by one of ordinary skill in the art to which this invention belongs. Singleton et al. (1994) *Dictionary of Microbiology and Molecular Biology*, Second edition, John Wiley and Sons (New York); Walker (ed) (1988) The *Cambridge Dictionary of Science and Technology*, The press syndicate of the University of Cambridge, NY; and Hale and Marham (1991) The Harper Collins Dictionary of Biology, Harper, Perennial, N.Y. provide one of skill with a general dictionary of many of the terms used in this invention. Although any methods and materials similar or equivalent to those described herein can be used in the practice or testing of the present invention, certain preferred methods and materials are described. For purposes of the present invention, the following terms are defined below.

The terms "isolated" or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

The term "subsequence" in the context of a particular nucleic acid sequence refers to a region of the nucleic acid equal to or smaller than the specified nucleic acid. Thus, for example, a viral inhibitor nucleic acid subsequence is a subsequence of a vector nucleic acid, because, in addition to encoding the viral inhibitor, the vector nucleic acid optionally encodes other components such as a promoter, a packaging site, chromosome integration sequences and the like.

Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid or the legion of double-strandedness can include a subsequence of each nucleic acid. An overview to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, N.Y.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecules Biology—Hybridization with Nucleic Acid Probes*, part I, chapter 2, "Overview of principles of hybridization and the strategy of nucleic acid probe assays", Elsevier, N.Y. Generally, highly stringent wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular probe. Nucleic acids which do not hybridize to each ocher under stringent Conditions are still Substantially identical if the polypeptides which they encode are substantially identical. This occurs, e.g., when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence. A nucleic acid is "substantially identical to a reference nucleic acid when it is at least about 70% identical, preferably at least about 80% identical, and optionally about 90% identical or more. When percentage of sequence identity is used in reference to proteins or peptides it is recognized that residue positions which are not identical often differ by conservative amino acid substitutions, where amino acids residues are substituted for other amino acid residues with similar chemical properties (e.g., charge or hydrophobicity) and therefore do not change the functional properties of the molecule. Where sequence differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus for example , where an identical amino acid is given a score of 1 and a non-conservative substitution is given a score of zero, a conservative substitution is given a score between zero and 1 The scoring of conservative substitutions is calculated, e.g., according to known algorithm. See, e.g., Meyers and Miller, Computer Applic. Biol. Sci., 4: 11–17 (1988); Smith and Waterman (1981) *Adv. Appl. Math.* 2: 482; Needleman and Wunsch (1970) *J. Mol. Biol.* 48: 443; Pearson and Lipman (1988) *Proc. Nacl. Aced. Sci. USA* 85: 2444; Higgins and Sharp (1988) *Gene*, 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the colons CGU, CGC, CGA, CGG, AGA, and AGG all encode the amino acid arginine. Thus, at every position where an arginine is specified by a codon, the codon can be altered to any of the corresponding colons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each colon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions, for one another.

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenytalanine (F), Tyrosine (Y), Tryptophan (VV).

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example; pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, Third Edition, W. E. Paul, ed., Raven Press, N.Y. (1993), which is incorporated herein by reference, for a more detailed description of other antibody fragments). While various antibody fragments are defined in terms of the digestion of an intact antibody; one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc. or (b) the variable region, or a portion thereof, is altered, replaced or exchanged with a variable region having a different or altered antigen specificity.

The term "immunoassay" is an assay that utilizes an antibody to specifically bind an analyze. The immunoassay is characterized by the use of specific binding properties of a particular antibody to isolate, target, and/or quantify the analyte.

An "anti-ORF" antibody is an antibody or antibody fragment that specifically binds a polypeptide encoded by the Neisseria meningitidis ORFs, described herein.

An "expression vector" includes a recombinant expression cassette which includes a nucleic acid which encodes a polypeptide which can be transcribed and translated by a cell. A "recombinant expression cassette" is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter. In some embodiments, the expression cassette also includes, e.g., an origin of replication, and/or chromosome integration elements. A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. The promoter also includes distal enhancer or repressor elements which can be located as much as several thousand base pairs from the start site of transcription. A "constitutive" promoter is a promoter which is active under most environmental conditions and states of development or cell differentiation. An "inducible" promoter responds to an extracellular stimulus. The term "operably linked" refers to functional linkage between a nucleic acid expression control sequence (such as a promoter or array of transcription factor binding sites) and a second nucleic acid sequence, wherein the expression control sequence directs transcription of the nucleic acid corresponding to the second sequence.

The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

An "immunogenic composition" is a composition which elicits the production of an antibody which binds a component of the composition when administered to a mammal, or which elicits the production of a cell-mediated immune response against a component of the composition.

An "antigenic epitope" in the context of a polypeptide is a polypeptide subsequence which, when presented as an immunogen, or as a portion of an immunogen (e.g., with a carrier protein or adjuvant or on the surface of a vital vector), elicits an antibody which specifically binds to the full length polypeptide.

DETAILED DESCRIPTION OF THE INVENTION

Using several new tools and techniques, the identification of bacterial gene(S) which are Involved in the process of cell adhesion and invasion are described. A Tn916-mutant library of *N. meningitidis*, serogroup B, strain NMB (Kathariou, S., et al. *Mol. Microbiol.*, 4:729–735), was examined for the lost ability to attach or invade tissue culture epithelial cells (HEC1-B). Several hundred mutants were screened, and one strain, VVV6, showed a significant >10-fold decrease in its ability to associate with the HEC1-B monolayer, compared to its parent strain; NMB. Southern hybridization, polymerase chain reaction, and DNA sequence analysis data revealed the presence of a single intact, Class 1, copy of transposon Tn916. To demonstrate linkage between the transposon insertion site and mutant phenotype backtransformants were created via homologous recombination. All seven recombinants also showed an invasion-deficient phenotype as observed with VVV6: Nucleotide sequence analysis shows that the Tn916 insertion occurred between two open reading frames (ORFs). The nature or function of the products encoded by these ORFs is not known: ORF 3 (SEQ ID NO:7) shows no significant homology any known gene, while ORF 2(ORF 2a (SEQ ID NO:4); ORF 2b (SEQ ID NO:5)) shows 60% identity to an *E. coli* gene with no known function. Adjacent to ORF 2, an open reading frame encoding ORF 1 was found. ORF 1 is the *Neisseria meningitidis frz* gene homologue.

Making *Neisseria meningitidis* Nucleic Acids and Polypeptides

Several specific nucleic acids encoding Neisseria meningitidis polypeptides are described herein. These nucleic acids can be made using standard recombinant or synthetic techniques. Given the nucleic acids of the present invention, one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich. Chemical Company (Milwaukee, Wis.), Glen Research, Inc., GIBCO BRL Life Technologies, Inc. (Gaithersberg, Md.), Fluky Chemica-Biochemika Analytika (Fluky Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. The nucleic acids of the invention are present in transformed or transfected cells, in transformed or transfected cell lysates, or in a partially purified or substantially pure form.

In vitro amplification techniques suitable for amplifying sequences for use as molecular probes or generating nucleic acid fragments for, subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Bergen, Sambrook et al. (1989) *Molecular Cloning–A Laboratory Manual* (2nd Ed) Vol. 1–3; and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acid. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids are summarized in Cheng et al. (1994) *Nature* 369: 684–685 and the references therein. One of skill will appreciate that essentially any RNA can be converted into a double stranded DNA suitable for restriction digestion, PCR expansion aid sequencing using reverse transcriptase and a polymerase. See, Ausbel, Sambrook and Bergen, all supra.

Oligonucleotides for use as probes, e.g., in in vitro *Neisseria meningitidis* nucleic acid amplification methods, or for use as nucleic acid probes to detect *Neisseria meningitidis* nucleic acids are typically synthesized chemically according to the solid phase phosphoramidite triester method described by Beaucage and Caruthers (1981), *Tehrahedron Letts.*, 22(20):1859–1862, e.g., using an automated synthesizer, e.g., as described in Needham-VanDevanter et al. (1984) *Nucleic Acids Res.*, 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Innis, Ausbel, Bergen, Needham VanDevanter and Mullis (all supra).

Polypeptides of the invention are optionally synthetically prepared in a wide variety of well-known ways. Polypeptides of relatively short size are typically synthesized in solution or on a solid support in accordance with conventional techniques. See, e.g., Merrifield (1963) *J. Am. Chem. Soc.* 85:2149–2154. Various automatic synthesizers and sequencers are commercially available and can be used in accordance with known protocols. See, e.g., Stewart and Young (1984) *Solid Phase Peptide Synthesis*, 2d. ed., Pierce Chemical Co. Polypeptides are also produced by recombinant expression of a nucleic acid encoding the polypeptide followed by purification using standard techniques. Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology*. Vol. 2: *Special Methods in Peptide Synthesis, Part A.*, Merrifield, et al. *J. Am. Chem. Soc.*, 85: 2149–2156 (1963), and Stewart et al., *Solid Phase Peptide Synthesis*, 2nd ed. Pierce Chem. Co., Rockford, Ill. (1984).

Cloning and Expressing *Neisseria meningitidis* Nucleic Acids

In a preferred embodiment, the polypeptides, or subsequences thereof, are synthesized using recombinant DNA methodology. Generally, this involves creating a DNA sequence that encodes the protein, placing the DNA in an expression cassette under the control of a particular promoter, expressing the protein in a host cell, isolating the expressed protein and, if required, renaturing the protein.

Once a nucleic acid encoding a polypeptide of the invention is isolated and cloned, the nucleic acid is optionally expressed in a recombinantly engineered cells known to those of skill in the art. Examples of such include bacteria, yeast, plant, filamentous fungi, insect (especially employing baculoviral vectors) and mammalian cells. The recombinant nucleic acids are operably linked to appropriate control sequences for expression in the selected host. For *E. coli*, example control sequences include the T7, trp, or lambda promoters, a ribosome binding site and preferably a transcription termination signal. For eukaryotic cells, the control sequences typically include a promoter and preferably an enhancer derived from immunoglobulin genes, SV40, cytomegalovirus, etc., and a polyadenylation sequence, and may include splice donor and acceptor sequences.

The plasmids of the invention Can be transferred into the chosen host cell by well-known methods such as Calcium Chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant polypeptides can be purified according to standard procedures of the art, including ammonium sulfate precipitation, affinity columns, column chromatography, gel electrophoresis and the like (see, generally, R. Scopes, *Polypeptide Purification*, Springer-Verlag, N.Y. (1982), Deutscher, *Methods in Enzymology* Vol. 182*: Guide to Polypeptide Purification*, Academic Press, Inc. N.Y. (1990)). Once purified, partially or to homogeneity as desired, the polypeptides may then be used (e.g., as immunogens for antibody production).

After chemical synthesis, biological expression, or purification, the polypeptides) may possess a conformation substantially different than the native conformations of the constituent polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (See, Debinski et al. (1993). *J. Biol. Chem*., 268: 14065–14070; Kreitman and Pastan (1993) *Bioconjug. Chem*., 4: 581–585; and Buchner, et al., (1992) *Anal. Biochem*., 205:263–270). Debinski et al., for example, describe the denaturation and reduction of inclusion body polypeptides in guanidine-DTE The polypeptide is then refolded in a redox buffer containing oxidized glutathione and L-arginine.

One of skill will recognize that modifications can be made to the polypeptides without diminishing their biological activity. Some modifications may be made to facilitate the cloning, expression or incorporation of the targeting molecule into a fusion polypeptide. Such modifications are well known to those of skill in the art and include, for example, a methionine added at the amino terminus to provide an initiation site, or additional amino acids (e.g., poly His) placed on either terminus to create conveniently located restriction sites or termination colons or purification sequences.

Making Conservative Modifications of the Nucleic Acids and Polypeptides of the Invention One of skill will appreciate that many conservative variations of the nucleic acid and polypeptide sequences of the figures and sequence listings yield functionally identical products. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions." in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively Substituted variations of each explicitly listed sequence are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Innis, Ausbel, Bergen, Needham VanDevanter and Mullis (all supra).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see, Merrifield, and Stewart and Young, supra).

One of skill can select a desired nucleic acid or polypeptide of the invention based upon the sequences provided and upon knowledge in the art regarding proteins generally. Knowledge regarding the nature of proteins and nucleic acids allows one of skill to select appropriate sequences with activity similar or equivalent to the nucleic acids and polypeptides disclosed in the sequence listings herein. The definitions section herein describes exemplar conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Screening for *Neisseria meningitidis* Nucleic Acids and the Use of *Neisseria meningitidis* Nucleic Acids as Molecular Probes The nucleic acids of the invention are useful as molecular probes, in addition to their utility in encoding the polypeptides described herein. A wide variety of formats and labels are available and appropriate for nucleic acid hybridization, including those reviewed in Tijssen (1993) *Laboratory Techniques in biochemistry and molecular biology-hybridization with nucleic acid probes* parts I and II, Elsevier, N.Y. and Choo (ed) (1994) *Methods In Molecular Biology* Volume 33—*In Situ Hybridization Protocols* Humana Press Inc., New Jersey (see also, other books in the Methods in Molecular Biology series); see especially, Chapter 21 of Choo (id) "Detection of Virus Nucleic Acids by Radioactive and Nonisotopic in Situ Hybridization"

For instance, PCR, LCR, and other amplification techniques (see, supra) are routinely used to detect Neisseria meningitidis nucleic acids in biological samples. Accordingly, in one class of embodiments; the nucleic acids of the invention are used as primers of templates, or as positive controls in amplification reactions for the detection of *Neisseria meningitidis* in a biological samples such as cerebrospinal fluid. Briefly, nucleic acids with sequence identity or complementarity to Seq 4 (SEQ ID NO:8), or the complement thereof are used as templates to synthetically produce oligonucleotides of about 15–23 nucleotides with sequences similar or identical to the complement of a selected *Neisseria meningitidis* nucleic acid subsequence. The oligonucleotides are then used as primers in amplification reactions such as PCR to detect selected *Neisseria meningitidis* nucleic acids in biological samples, such as a cerebrospinal fluid extract. A nucleic acid of the invention (i.e., a cloned nucleic acid corresponding to the region to be amplified) is also optionally used as an amplification template in a separate reactions as a positive control to determine that the amplification reagents and hybridization conditions are appropriate.

Other methods for the detection of nucleic acids in biological samples using nucleic acids of the invention include Southern blots, northern blots, in situ hybridization (including Fluorescent in situ hybridization (FISH), and a variety of other techniques overviewed in Choo (supra)). A variety of automated solid-phase detection techniques are also appropriate. For instance, very large scale immobilized polymer arrays (VLSIPS™) are used for the detection of nucleic acids. See, Tijssen (supra), Fodor et al. (1991) *Science*, 251: 767–777; Sheldon et al. (1993) *Clinical Chemistry* 39(4): 718–719 and Kozal et al. (1996) *Nature Medicine* 2(7): 753–759.

Antibodies to selected *Neisseria meningitidis* ORF polypeptide(s).

Antibodies are raised to selected Neisseria meningitidis ORF polypeptides of the present invention, including individual, allelic, strain, or species variants, and fragments thereof, both in their naturally occurring (full-length) forms and in recombinant forms. Additionally, antibodies are raised to these polypeptides in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A number of immunogens are used to produce antibodies specifically reactive with *Neisseria meningitidis* ORF 1 (SEQ ID NO:2), ORF 2a (SEQ ID NO:4), ORF 2b (SEQ ID NO:5), or ORF 3 (SEQ ID NO:7) polypeptides. Recombinant or synthetic polypeptides of 10 amino acids in length, or greater, typically 20 amino acids in length, or greater, more typically 30 amino acids in length, or greater, selected from amino acid sub-sequences of ORF 1 (SEQ ID NO:2), ORF 2a (SEQ ID NO:4), ORF 2b (SEQ ID NO:5), or ORF 3 (SEQ ID NO:7) are the preferred polypeptide immunogen for the production of monoclonal or polyclonal antibodies. In one class of preferred embodiments, an immunogenic peptide conjugate is also included as an immunogen. Naturally occurring polypeptides are also used either in pure or impure form. An antigenic domain is ordinarily at least about 3 amino acids in length often at least about 5 amino acids in length, generally at least about 9 amino acids in length and often at least about 15 amino acids in length. The antigenic domain ordinarily includes the binding site for an antibody, which typically vary from 3 to about 20 amino acids in length, and which are generally about 8 to 12 amino acids in length.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen (antigen), preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired (see, e.g., Coligan (1991) *Current Protocols in Immunology* Wiley/Greene, NY; and Harlow and Lane (1989) *Antibodies: A Laboratory Manual* Cold Spring Press, NY).

Antibodies, including binding fragments and single chain recombinant versions thereof, against whole or predetermined fragments of selected *Neisseria meningitidis* ORFs are raised by immunizing animals, e.g., with conjugates of the fragments with carrier proteins as described above. Typically, the immunogen of interest is a peptide of at least about 10 amino acids, more typically the peptide is 20 amino acids in length, generally the fragment is 25 amino acids in length and often the fragment is 30 amino acids in length or greater. The peptides are optionally coupled to a carrier protein (e.g., as a fusion protein), or are recombinantly expressed in an immunization vector. Antigenic determinants on selected *Neisseria meningitidis* ORF peptides to which antibodies bind are typically 3 to 10 amino acids in length.

Monoclonal antibodies are prepared from cells secreting the desired antibody. These antibodies are screened for binding to normal or modified polypeptides or screened for agonistic or antagonistic activity, e.g., activity mediated through a selected *Neisseria meningitidis* ORF polypeptide. Specific monoclonal and polyclonal antibodies will usually bind with a $K_D$ of at least about 0.1 mM, more usually at least about 50 µM, and preferably at least about 1 µM or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology,* 14: 309–314).

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention are also used for affinity chromatography in isolating natural or recombinant *Neisseria meningitidis* ORF polypeptides. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified polypeptides are released.

The antibodies can be used to screen expression libraries for particular expression products such as normal or abnormal *Neisseria meningitidis* ORF polypeptides, or for related polypeptides related to a selected *Neisseria meningitidis* ORF polypeptide. Optionally, the antibodies in such a procedure are labeled with a moiety allowing easy detection of presence of antigen by antibody binding.

Antibodies raised against polypeptides can also be used to raise anti-idiotypic antibodies. These are useful for detecting or diagnosing various pathological conditions related to the presence of the respective antigens.

The antibodies of this invention can also be administered to an organism (e.g., a human patient) for therapeutic purposes (e.g., to block infection by *Neisseria meningitidis*, or as targeting molecules when conjugated or fused to effector molecules such as labels, cytotoxins, enzymes, growth factors, drugs, etc.). Antibodies administered to an organism other than the species in which they are raised can be immunogenic. Thus, for example, murine antibodies administered to a human can induce an immunologic response against the antibody (e.g., the human anti-mouse antibody (HAMA) response), particularly after multiple administrations. The immunogenic properties of the antibody are reduced by altering portions, or all, of the antibody into characteristically human sequences thereby producing chimeric, or human, antibodies respectively.

Humanized (chimeric) antibodies are immunoglobulin molecules comprising a human and non-human portion. The antigen combining region (or variable region) of a humanized chimeric antibody is derived from a non-human source (e.g., murine) and the constant region of the chimeric antibody (which confers biological effector function, such as cytotoxicity, to the immunoglobulin) is derived from a human source. The humanized chimeric antibody has the antigen binding specificity of the non-human antibody molecule and the effector function conferred by the human antibody molecule. A large number of methods of generating chimeric antibodies are well known to those of skill in the art (see, e.g., U.S. Pat. Nos.: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

In general, the procedures used to produce these chimeric antibodies consist of the following steps (the order of some steps interchangeable): (a) identifying and cloning the correct gene segment encoding the antigen binding portion of the antibody molecule; this gene segment (known as the VDJ, variable, diversity and joining regions for heavy chains or VJ, variable, joining regions for light chains (or simply as the V or Variable region) may be in either the cDNA or genomic form; (b) cloning the gene segments encoding the constant region or desired part thereof; (c) ligating the variable region with the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); and, (f) introducing the DNA into eukaryotic cells (transfection) most often mammalian lymphocytes.

Antibodies of several distinct antigen binding specificities have been manipulated by these protocols to produce chimeric proteins (e.g., anti-TNP: Boulianne et al. (1984) *Nature,* 312: 643; and anti-tumor antigens: Sahagan et al. (1986) *J. Immunol.,* 137: 1066). Likewise, several different effector functions have been achieved by linking new sequences to those encoding the antigen binding region. Some of these effectors include enzymes (Neuberger et al. (1984) *Nature* 312: 604), immunoglobulin constant regions from another species, and constant regions of another immunoglobulin chain (Sharon et al. (1984) *Nature* 309: 364; Tan et al., (1985) *J. Immunol.* 135: 3565–3567).

In one preferred embodiment, a recombinant DNA vector is used to transfect a cell line that produces an antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugate to a drug, toxin, or other molecule, etc.), and a "target sequence" which allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc. Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA which encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the task of cloning both heavy and light chain variable region genes from each B-cell clone expressing a useful antigen specificity. In addition to circumventing the process of cloning variable region genes, the level of expression of chimeric antibody is higher when the gene is at its natural chromosomal location, rather than at a random position in the genome. Detailed methods for preparation of chimeric (humanized) antibodies can be found in U.S. Pat. No. 5,482,856.

In another embodiment, this invention provides for fully human antibodies against selected *Neisseria meningitidis* ORF polypeptides. Human antibodies consist entirely of characteristically human immunoglobulin sequences. The human antibodies of this invention can be produced in using a wide variety of methods (see, e.g., Larrick et al., U.S. Pat. No. 5,001,065, for review).

In one preferred embodiment, the human antibodies of the present invention are produced initially in trioma cells. Genes encoding the antibodies are then cloned and expressed in other cells, such as nonhuman mammalian cells.

The general approach for producing human antibodies by trioma technology is described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmortalized human peripheral B lymphocytes. This fusion generates a xenogeneic hybrid cell containing both human and mouse chromosomes (see, Engelman, supra.). Xenogeneic cells that have lost the capacity to secrete antibodies are selected. Preferably, a xenogeneic cell is selected that is resistant to a selectable marker such as 8-azaguanine. Cells possessing resistance to 8-azaguanine are unable to propagate on hypoxanthine-aminopterin-thymidine (HAT) or azaserine-hypoxanthine (AH) media.

The capacity to secrete antibodies is conferred by a further fusion between the xenogeneic cell and B-lymphocytes immunized against a selected *Neisseria meningitidis* ORF polypeptide, or an epitope thereof. The B-lymphocytes are obtained from the spleen, blood or lymph nodes of human donor. If antibodies against a specific antigen rather than a full length polypeptide. Alternatively, B-lymphocytes are obtained from an unimmunized individual and stimulated with a polypeptide, or a epitope thereof, in vitro. In a further variation, B-lymphocytes are obtained from an infected, or otherwise immunized individual, and then hyperimmunized by exposure to a selected *Neisseria meningitidis* ORF polypeptide for about seven to fourteen days, in vitro.

The immunized B-lymphocytes prepared by one of the above procedures are fused with a xeonogenic hybrid cell by well known methods. For example, the cells are treated with 40–50% polyethylene glycol of MW 1000–4000, at about 37° C. for about 5–10 min. Cells are separated from the fusion mixture and propagated in media selective for the desired hybrids. When the xenogeneic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to a selected *Neisseria meningitidis* polypeptide or an epitope thereof. Triomas producing human antibodies having the desired specificity are subcloned, e.g., by the limiting dilution technique, and grown in vitro, in culture medium, or are injected into selected host animals and grown in vivo.

The trioma cell lines obtained are then tested for the ability to bind a polypeptide or an epitope thereof. Antibodies are separated from the resulting culture medium or body fluids by conventional antibody-fractionation procedures, such as ammonium sulfate precipitation, DEAE cellulose chromatography and affinity chromatography.

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the extensive viral screening required for human cell lines.

The genes encoding the heavy and light chains of immunoglobulins secreted by trioma cell lines are cloned according to methods, including the polymerase chain reaction, known in the art (see, e.g., Sambrook, and Berger & Kimmel, both supra). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987), *Sequences of Proteins of Immunological Interest*, U.S. Department of Health and Human Services.

In addition to the DNA segments encoding anti-ORF immunoglobulins or fragments thereof, other substantially homologous modified immunoglobulins can be readily designed and manufactured utilizing various recombinant DNA techniques known to those skilled in the art such as site-directed mutagenesis (see Gillman & Smith (1979) *Gene,* 8: 81–97; Roberts et al. (1987) *Nature,* 328: 731–734). Such modified segments will usually retain antigen binding capacity and/or effector function. Moreover, the modified segments are usually not so far changed from the original trioma genomic sequences to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations or properties.

The recombinant polynucleotide constructs will typically include an expression control sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the human immunoglobulins.

These expression vectors are typically replicable in the host organisms either as episomes or as an integral part of the host chromosomal DNA. Commonly, expression vectors will contain selection markers, e.g., ampicillin-resistance or hygromycin-resistance, to permit detection of those cells transformed with the desired DNA sequences. In general, prokaryotes or eukaryotic cells are used for cloning the DNA sequences encoding a human immunoglobulin chain.

Other approaches include in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produce human antibodies are prepared (see, e.g., 5,506, 132). Other approaches include immunization of mice transformed to express human immunoglobulin genes, and phage display screening (Vaughan et al. supra.).

Cell-Mediated Immune Responses

In addition to the production of antibodies, the present invention provides for cell-mediated immune responses against *Neisseria meningitidis.* As above, a polypeptide of the invention (e.g., ORF 1 (SEQ ID NO:2), ORF 2a (SEQ ID NO:4), ORF 2b (SEQ ID NO:5), or ORF 3 (SEQ ID NO:7), or a subsequence thereof) is administered to a mammal. The proliferation effect of these antigens is tested in a standard MLR assay. MLR assays or "mixed lymphocyte response" assays are the standard in vitro assay of antigen presenting function in cellular immunity. The assay measures the proliferation of T cells after stimulation by a selected antigen-presenting cell type. The number of T cells produced are typically characterized by measuring T cell proliferation based on incorporation of $^3$H-thymidine in culture. Similar methods are used in vivo in nude of SCID mouse models. See also, Paul (supra) at chapter 31. The most commonly measured from of cell-mediated immune response is a cytotoxic T-lymphocyte (CTL) response.

Antigenic peptides are used to elicit CTL ex vivo. The resulting CTL, can be used to treat chronic infections in patients that do not respond to other conventional forms of therapy, or will not respond to a peptide vaccine approach of therapy. Ex vivo CTL responses to a particular pathogen (infectious agent or tumor antigen) are induced by incubating in tissue culture the patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTLs, the cells are infused back into the patient, where they will destroy their specific target cell (e.g., an infected cell).

Detection of *Neisseria meningitidis*

As indicated above, *Neisseria meningitidis* infection causes serious health problems, and has the potential to reach epidemic proportions in some populations. Accordingly, new methods of detecting infection of patients by *Neisseria meningitidis* is of considerable value.

Thus, it is desirable to determine the presence or absence of *Neisseria meningitidis* in a patient, or to quantify the severity of infection, or quantify the expression of *Neisseria meningitidis* polypeptides or nucleic acids. In addition, the polypeptides of the invention are used to detect antisera against the polypeptides, e.g., in patients previously infected with *Neisseria meningitidis.*

Detection of *Neisseria meningitidis* or antisera against *Neisseria meningitidis* is accomplished by assaying the products of the *Neisseria meningitidis* nucleic acids of the invention; the nucleic acids themselves, or antibodies against polypeptides encoded by the nucleic acids. It is desirable to determine whether polypeptide expression is present, absent, or abnormal (e.g. because of an abnormal gene product or because of abnormal expression).

The selected *Neisseria meningitidis* nucleic acid or nucleic acid product (i.e., an mRNA or polypeptide) is preferably detected and/or quantified in a biological sample. Such samples include, but are not limited to, cerebrospinal fluid, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect *Neisseria meningitidis* or *Neisseria meningitidis* gene products in samples from any mammal, such as dogs, cats, sheep, cattle, rodents, primates and pigs.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

In one embodiment, this invention provides for methods of detecting and/or quantifying *Neisseria meningitidis* gene expression by assaying the underlying gene (or a fragment thereof) or by assaying the gene transcript (mRNA). The assay can be for the presence or absence of the normal gene or gene product, for the presence or absence of an abnormal gene or gene product, or quantification of the transcription levels of normal or abnormal gene products.

In a preferred embodiment, nucleic acid assays are performed with a sample of nucleic acid isolated from the organism to be tested. In the simplest embodiment, such a nucleic acid sample is the total mRNA isolated from a biological sample. The nucleic acid (e.g., either genomic DNA or mRNA) may be isolated from the sample according to any of a number of methods well known to those of skill in the art.

Methods of isolating total DNA or mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993)).

Frequently, it is desirable to amplify the nucleic acid sample prior to hybridization. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in *PCR Protocols, A Guide to Methods and Applications,* Innis et al., Academic Press, Inc. N.Y., (1990). Other suitable amplification methods include, but are not limited to those described supra.

Amplification-based assays are well known to those of skill in the art (see, e.g., Innis supra.). The *Neisseria meningitidis* nucleic acid sequences provided are sufficient to teach one of skill to routinely select primers to amplify any portion of the gene. It is expected that one of skill is thoroughly familiar with the theory and practice of nucleic acid hybridization and primer selection. Gait, ed. *Oligonucleotide Synthesis: A Practical Approach,* IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology,* volume 20; and Tijssen (1993) *Laboratory Techniques in biochemistry and molecular biology— hybridization with nucleic acid probes,* e.g., part I chapter 2 "overview of principles of hybridization and the strategy of nucleic acid probe assays", Elsevier, N.Y. provide a basic guide to nucleic acid hybridization. Innis supra provides an overview of primer selection. In addition, PCR amplification products are optionally detected on a polymer array as described in Fodor et al. (1991) *Science,* 251: 767–777; Sheldon et al. (1993) *Clinical Chemistry* 39(4): 718–719, and Kozal et al. (1996) *Nature Medicine* 2(7): 753–759.

Most typically, amplification primers are between 8 and 100 nucleotides in length, and preferably between about 10 and 30 nucleotides in length. More typically, the primers are between about 15 and 25 nucleic acids in length.

One of skill will recognize that the 3' end of an amplification primer is more important for PCR than the 5' end. Investigators have reported PCR products where only a few nucleotides at the 3' end of an amplification primer were complementary to a DNA to be amplified. In this regard, nucleotides at the 5' end of a primer can incorporate structural features unrelated to the target nucleic acid; for instance, in one preferred embodiment, a sequencing primer hybridization site (or a complement to such as primer, depending on the application) is incorporated into the amplification primer, where the sequencing primer is derived from a primer used in a standard sequencing kit, such as one using a biotinylated or dye-labeled universal M13 or SP6 primer. Alternatively, the primers optionally incorporate restriction endonuclease sites. The primers are selected so that there is no complementarity between any known sequence which is likely to occur in the sample to be amplified and any constant primer region. One of skill will appreciate that constant regions in the primer sequences are optional.

Typically, all primer sequences are selected to hybridize only to a perfectly complementary DNA, with the nearest mismatch hybridization possibility from known DNA sequences which are likely to occur in the sample to be amplified having at least about 50 to 70% hybridization mismatches, and preferably 100% mismatches for the terminal 5 nucleotides at the 3' end of the primer.

The primers are selected so that no secondary structure forms within the primer. Self-complementary primers have poor hybridization properties, because the complementary portions of the primers self hybridize (i.e., form hairpin structures). The primers are also selected so that the primers do not hybridize to each other, thereby preventing duplex formation of the primers in solution, and possible concatenation of the primers during PCR. If there is more than one constant region in the primer, the constant regions of the primer are selected so that they do not self-hybridize or form hairpin structures.

Where sets of amplification primers (i.e., the 5' and 3' primers used for exponential amplification) are of a single length, the primers are selected so that they have roughly the same, and preferably exactly the same overall base composition (i.e., the same A+T to G+C ratio of nucleic acids). Where the primers are of differing lengths, the A+T to G+C ratio is determined by selecting a thermal melting temperature for the primer-DNA hybridization, and selecting an A+T to G+C ratio and probe length for each primer which has approximately the selected thermal melting temperature.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector program from Kodak. In addition to commercially available programs for primer selection, one of skill can easily design simple programs for any of the preferred selection steps. Amplification primers can be selected to provide amplification products that span specific deletions, truncations, and insertions in an amplification target, thereby facilitating the detection of specific abnormalities such as a transposon insertion as described herein.

Where it is desired to quantify the transcription level (and thereby expression) of a normal or mutated *Neisseria meningitidis* gene is a sample, the nucleic acid sample is one in which the concentration of the mRNA transcript(s) of the gene, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of a target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

*Neisseria meningitidis* polypeptide assays.

The expression of selected *Neisseria meningitidis* polypeptides can also be detected and/or quantified by detecting or quantifying the expressed polypeptide. The polypeptides can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay(RIA), enzyme-linked immunosorbent assays (ELISAs), immunofluorescent assays, western blotting, and the like.

In a particularly preferred embodiment, the polypeptides are detected in an electrophoretic protein separation, more preferably in a two-dimensional electrophoresis, while in a most preferred embodiment, the polypeptides are detected using an immunoassay.

As used herein, an immunoassay is an assay that utilizes an antibody to specifically bind to the analyte (e.g., selected polypeptide, such as ORF 1 (SEQ ID NO:2), ORF 2a (SEQ ID NO:4), ORF 2b (SEQ ID NO:5), or ORF 3 (SEQ ID NO:7)). The immunoassay is thus characterized by detection of specific binding of a polypeptide to an anti-polypeptide antibody, as opposed to the use of other physical or chemical properties to isolate, target, and quantify the analyte.

As indicated above, the presence or absence of polypeptides in a biological sample can be determined using electrophoretic methods. Means of detecting proteins using electrophoretic techniques are well known to those of skill in the art (see generally, R. Scopes (1982) *Protein Purification,* Springer-Verlag, N.Y.; Deutscher, (1990) *Methods in Enzymology Vol.* 182: *Guide to Protein Purification.,* Academic Press, Inc., N.Y.).

In a preferred embodiment, the polypeptides are detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume* 37: *Antibodies in Cell Biology,* Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte. The capture agent is a moiety that specifically binds to the analyte. In a preferred embodiment, the capture agent is an antibody that specifically binds polypeptide(s) or polypeptide subsequences (e.g., antigenic domains which specifically bind to the antibody). In a second preferred embodiment, the capture agent is the polypeptide and the analyte is antisera comprising an antibody which specifically binds to the polypeptide.

Immunoassays often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled anti-polypeptide antibody. Alternatively, the labeling agent may be a third moiety, such as another antibody, that specifically binds to the antibody/polypeptide complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as streptococcal protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401–1406, and Akerstrom, et al. (1985) *J. Immunol.,* 135: 2589–2542).

Throughout the assays, incubation and/or washing steps are optionally performed after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Immunoassays for detecting polypeptides may be either competitive or noncompetitive. Noncompetitive immunoassays are assays in which the amount of captured analyte is directly measured. In one preferred "sandwich" assay, for example, the capture agent can be bound directly to a solid substrate where they are immobilized. These immobilized capture agent then captures analyte present in the test sample. The analyte thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

In competitive assays, the initial amount of analyte present in the sample is measured indirectly by measuring the amount of an added (exogenous) analyte displaced (or competed away) from a capture agent by the analyte present in the sample. In one competitive assay, a known amount of, in this case, analyte is added to the sample and the sample is then contacted with a capture agent. The amount of exogenous analyte bound to the capture agent is inversely proportional to the initial analyte present in the sample.

In a preferred embodiment, western blot (immunoblot) analysis is used to detect and quantify the presence of selected *Neisseria meningitidis* in the sample. The technique generally comprises separating sample proteins by gel electrophoresis on the basis of molecular weight, transferring the separated proteins to a suitable solid support (such as a nitrocellulose filter, a nylon filter, or derivatized nylon filter), and incubating the sample with the antibodies that specifically bind the selected polypeptide. The antibodies specifically bind to polypeptide on the solid support. These antibodies are optionally directly labeled or alternatively are optionally subsequently detected using labeled antibodies (e.g., labeled sheep anti-mouse antibodies) that specifically bind to the selected polypeptide.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41). Enzyme linked assays (e.g., ELISA assays) are also preferred.

The assays of this invention as scored (as positive or negative for *Neisseria meningitidis* or a selected *Neisseria meningitidis* polypeptide) according to standard methods well known to those of skill in the art. The particular method of scoring will depend on the assay format and choice of label. For example, a western blot assay can be scored by visualizing the colored product produced by the enzymatic label. A clearly visible colored band or spot at the correct molecular weight is scored as a positive result, while the absence of a clearly visible spot or band is scored as a negative. In a preferred embodiment, a positive test will show a signal intensity (e.g., polypeptide quantity) at least twice that of the background and/or control and more preferably at least 3 times or even at least 5 times greater than the background and/or negative control.

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin.

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

As mentioned above, depending upon the assay, various components, including the antigen, target antibody, or anti-antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene eterphthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes,* Ichiro Chibata, Halsted Press, New York, 1978, and Cuatrecasas (1970) *J. Biol. Chem.* 245 3059).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

Detection kits

The present invention also provides kits for the diagnosis of patients infected with *Neisseria meningitidis*. The kits preferably include one or more reagents for determining the presence or absence of a selected *Neisseria meningitidis* nucleic acid or protein, i.e., any of the nucleic acids or proteins described herein. Preferred reagents include nucleic acid probes that specifically bind to Seq 1 (SEQ ID NO:1), Seq 2 (SEQ ID NO: 3), Seq 3 (SEQ ID NO:6), or Seq 4 (SEQ ID NO:8) cDNA corresponding to Seq 1 (SEQ ID NO:1), Seq 2 (SEQ ID NO:3), Seq 3 (SEQ ID NO:6), or Seq 4 (SEQ ID NO:8), or a subsequence thereof; probes that specifically bind to an abnormal *Neisseria meningitidis* gene (e.g., one containing premature truncations, insertions, or deletions), and antibodies that specifically bind to polypeptides or subsequences thereof. The antibody or hybridization probe may be free or immobilized on a solid support such as a test tube, a microtiter plate, a dipstick or the like. The kit may also contain instructional materials teaching the use of the antibody or hybridization probe in an assay for the detection of *Neisseria meningitidis*, a container or other packaging material or the like.

The kits may include alternatively, or in combination with any of the other components described herein, an antibody which specifically binds a polypeptide of the invention. The antibody can be monoclonal or polyclonal. The antibody can be conjugated to another moiety such as a label and/or it can be immobilized on a solid support (substrate).

The kits also optionally include a second antibody for detection of polypeptide/antibody complexes or for detection of hybridized nucleic acid probes. The kits optionally include appropriate reagents for detection of labels, positive and negative controls, washing solutions, dilution buffers and the like.

Intracellular Immunization and Gene Therapy

In one preferred class of embodiments, the nucleic acids of the invention are used in cell transformation procedures for intracellular immunization and gene therapy to inhibit or prevent meningitis caused by *Neisseria meningitidis* serogroup B. Gene therapy provides methods for combating chronic infectious diseases. In vitro, ex vivo and in vivo procedures are used. The nucleic acids of the invention optionally encode antisense oligonucleotides which bind to selected *Neisseria meningitidis* nucleic acids (e.g., RNAs encoded by Seq 1 (SEQ ID NO:1), Seq 2 (SEQ ID NO:3), Seq 3 (SEQ ID NO:6), or Seq 4 (SEQ ID NO:8); see FIGS. 5, 6, 7 and 4, respectively) with high affinity. These oligonucletides are typically cloned into gene therapy vectors that are competent to transform cells (such as human or other mammalian cells) in vitro and/or in vivo.

Several approaches for introducing nucleic acids into cells in vivo, ex vivo and in vitro have been used. These include liposome based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84, 7413—7414) and replication-defective retroviral vectors harboring a therapeutic polynucleotide sequence as part of the retroviral genome (see, e.g., Miller et al. (1990) *Mol. Cell. Biol.* 10:4239 (1990); Koiberg (1992) *J. NIH Res.* 4:43, and Cornetta et al. *Hum. Gene Ther.* 2:215 (1991)).

For a review of gene therapy procedures, see, Anderson, *Science* (1992) 256:808–813; Nabel and Felgner (1993) TIBTECH 11:211–217; Mitani and Caskey (1993) TIBTECH 11:162–166; Mulligan (1993) *Science* 926–932; Dillon (1993) TIBTECH 11:167–175; Miller (1992) *Nature* 357:455–460; Van Brunt (1988) *Biotechnology* 6(10):1149–1154; Vigne (1995) *Restorative Neurology and Neuroscience* 8:35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Therapy* (1994) 1:13–26.

Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66(5)) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra). The vectors are optionally psuedotyped to extend the host range of the vector to cells which are not infected by the retrovirus corresponding to the vector. The vesicular stomatitis virus envelope glycoprotein (VSV-G) has been used to construct VSV-G-pseudotyped HIV vectors which can infect hematopoietic stem cells (Naldini et al. (1996) *Science* 272:263, and Akkina et al. (1996) *J Virol* 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.*, 4:2072–2081; Hermonat and Muzyczka (1984) *Proc. Natl. Acad. Sci. USA*, 81:6466–6470: McLaughlin et al. (1988) and Samulski et al. (1989) *J. Virol.*, 63:03822–3828. Cell lines that can be transformed by rAAV include those described in Lebkowski et al. (1988) *Mol. Cell. Biol.*, 8:3988–3996.

Ex vivo methods for inhibiting *Neisseria meningitidis* replication in a cell in an organism involve transducing the cell ex vivo with a nucleic acid of this invention which expresses an antisense oligonucleotide of the invention, and introducing the cell into the organism. The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells. Transformed cells are cultured by means well known in the art. See, also Kuchler et al. (1977) *Biochemical Methods in Cell Culture and Virology*, Kuchler, R. J., Dowden, Hutchinson and Ross, Inc., and Atlas (1993) *CRC Handbook of Microbiological Media* (Parks ed) CRC press, Boca Raton, Fla. Mammalian cell systems often will be in the form of monolayers of cells, although mammalian cell suspensions are also used. Alternatively, cells can be derived from those stored in a cell bank (e.g., a blood bank).

In one preferred use of the invention, expression of an oligonucleotide inhibits *Neisseria meningitidis* replication in any of those cells already infected with *Neisseria meningitidis*, in addition to conferring a protective effect to cells which are not infected. Thus, an organism infected with *Neisseria meningitidis* can be treated for the infection by transducing a population of its cells with a vector of the invention and introducing the transduced cells back into the organism. Thus, the present invention provides a method of protecting cells in vitro, ex vivo or in vivo, even when the cells are already infected with the virus against which protection is sought.

A ribozyme is a catalytic antisense RNA molecule that cleaves other RNA molecules having particular target nucleic acid sequences. General methods for the construction of ribozymes against selected targets, including hairpin ribozymes, hammerhead ribozymes, RNAse P ribozymes (i.e., ribozymes derived from the naturally occurring RNAse P ribozyme from prokaryotes or eukaryotes) are known in the art. Castanotto et al (1994) *Advances in Pharmacology* 25:289–317 provides and overview of ribozymes in general, including group I ribozymes, hammerhead ribozymes, hairpin ribozymes RNAse P, and axhead ribozymes.

Briefly, two types of ribozymes that are particularly useful in this invention include the hairpin ribozyme and the hammerhead ribozyme. The hammerhead ribozyme (see, Rossie et al. (1991) *Pharmac. Ther.* 50:245–254; Forster and Symons (1987) *Cell* 48:211–220; Haseloff and Gerlach (1988)

Bruening (1988) *Nature* 334:196; Haseloff and Gerlach (1988) *Nature* 334:585; and Dropulic et al and Castanotto et al., and the references cited therein, supra) and the hairpin ribozyme (see, e.g., Hampel et al. (1990) *Nucl. Acids Res.* 18:299–304; Hempel et al., (1990) European Patent Publication No. 0 360 257; U.S. Pat. No. 5,254,678; Wong-Staal et al., PCT/US94/05700; Ojwang et al. (1993) *Proc Natl Acad Sci USA* 90:6340–6344; Yamada et al. (1994) *Human Gene Therapy* 1:39–45; Leavitt et al. (1995) *Proc Natl Acad Sci USA* 92:699–703; Leavitt et al. (1994) *Human Gene Therapy* 5:1151–1120; and Yamada et al. (1994) *Virology* 205:121–126) are catalytic molecules having antisense and endoribonucleotidase activity.

The typical sequence requirement for the GUC hairpin ribozyme is a RNA sequence consisting of NNNG/CN*GUCNNNNNNNN (SEQ ID NO:9) (where N*G is the cleavage site, and where N is any of G, U, C, or A). The sequence requirement at the cleavage site for the hammerhead ribozyme is any RNA sequence consisting of NUX (where N is any of G, U, C, or A and X represents C, U or A). Accordingly, the same target within the hairpin leader sequence, GUC, is targetable by the hammerhead ribozyme. The additional nucleotides of the hammerhead ribozyme or hairpin ribozyme is determined by the common target flanking nucleotides and, e.g., the hammerhead consensus sequences.

Altman (1995) *Biotechnology* 13:327–329 and the references therein describe the use of RNAse P as a therapeutic agent directed against flu virus. Similar therapeutic approaches can be used against selected *Neisseria meningitidis* RNAs by incorporating RNAse P catalytic domains into the antisense molecules of the invention.

The anti sense molecules, including the ribozymes of this invention and DNA encoding the ribozymes, can be chemically synthesized as described supra, or prepared from a DNA molecule (that upon transcription yields an RNA molecule) operably linked to an appropriate promoter.

Reporter genes, Sites of Replication and Selectable Markers

To monitor the progress of cellular transduction, a marker or "reporter" gene is optionally encoded by the nucleic acids of the invention. The inclusion of detectable markers provides a means of monitoring the infection and stable transduction of target cells. Markers include components of the beta-galactosidase gene, the firefly luciferase gene and the green fluorescence protein (see, e.g., Chalfie et al. (1994) Science 263:802).

The vectors of the invention optionally include features which facilitate the replication in more than one cell type. For example, the replication of a plasmid as an episomal nucleic acid in mammalian cells can be controlled by the large T antigen in conjunction with an appropriate origin of replication, such as the origin of replication derived from the BK papovavirus. Many other features which permit a vector to be grown in multiple cell types (e.g., shuttle vectors which are replicated in prokaryotic and eukaryotic cells) are known.

Selectable markers which facilitate cloning of the vectors of the invention are optionally included. Sambrook and Ausbel, both supra, provide an overview of selectable markers.

The present invention provides nucleic acids for the transformation of cells in vitro and in vivo. These nucleic acids are typically packaged in vector particles. The nucleic acids are transfected into cells through the interaction of the vector particle surrounding the nucleic acid and the cellular receptor for the vector. For example, cells which are transfected by HIV based vectors in vitro include $CD4^+$cells, including T-cells such as Molt-4/8 cells, SupT1 cells, H9 cells, C8166 cells and myelomonocytic (U937) cells, as well as primary human lymphocytes, and primary human monocyte-macrophage cultures, peripheral blood dendritic cells, follicular dendritic cells, epidermal Langerhans cells, megakaryocytes, microglia, astrocytes, oligodendroglia, $CD8^+$cells, retinal cells, renal epithelial cells, cervical cells, rectal mucosa, trophoblastic cells, and cardiac myocytes (see also, Rosenburg and Fauci Rosenburg and Fauci (1993) in *Fundamental Immunology, Third Edition* Paul (ed) Raven Press, Ltd., New York). AAV based vectors transduce most mammalian cells. In one particularly preferred class of embodiments, the nucleic acids of the invention are used in cell transformation procedures for gene therapy.

In addition to viral particles, a variety of protein coatings can be used to target nucleic acids to selected cell types. Transferrin-poly-cation conjugates enter cells which comprise transferrin receptors, See, e.g., Zenke et al (1990) *Proc. Natl. Acad. Sci. USA* 87:3655–3659; Curiel (1991) *Proc. Natl. Acad Sci USA* 88:8850–8854 and Wagner et al. (1993) *Proc. Natl. Acad. Sci. USA* 89:6099–6013.

Naked plasmid DNA bound electrostatically to poly-l-lysine or poly-l-lysine-transferrin which has been linked to defective adenovirus mutants can be delivered to cells with transfection efficiencies approaching 90% (Curiel et al. (1991) *Proc Natl Acad Sci USA* 88:8850–8854; Cotten et al. (1992) *Proc Natl Acad Sci USA* 89:6094–6098; Curiel et al. (1992) *Hum Gene Ther* 3:147–154; Wagner et al. (1992) *Proc Natl Acad Sci USA* 89:6099–6103; Michael et al. (1993) *J Biol Chem* 268:6866–6869; Curiel et al. (1992) *Am J Respir Cell Mol Biol* 6:247–252, and Harris et al. (1993) *Am J Respir Cell Mol Biol* 9:441–447). The adenovirus-poly-l-lysine-DNA conjugate binds to the normal adenovirus receptor and is subsequently internalized by receptor-mediated endocytosis. The adenovirus-poly-l-lysine-DNA conjugate binds to the normal adenovirus receptor and is subsequently internalized by receptor-mediated endocytosis. Similarly, other virus-poly-l-lysine-DNA conjugates bind the normal viral receptor and are subsequently internalized by receptor-mediated endocytosis. Accordingly, a variety of viral particles can be used to target vector nucleic acids to cells.

In addition to, or in place of receptor-ligand mediated transduction, the vector nucleic acids of the invention are optionally complexed with liposomes to aid in cellular transduction. Liposome based gene delivery systems are described in Debs and Zhu (1993) WO 93/24640; Mannino and Gould-Fogerite (1988) *BioTechniques* 6(7):682–691; Rose U.S. Pat. No. 5,279,833; Brigham (1991) WO 91/06309; and Felgner et al. (1987) *Proc. Natl. Acad. Sci. USA* 84:7413–7414.

Ex Vivo Transduction of Cells

Ex vivo methods for inhibiting viral replication in a cell in an organism involve transducing the cell ex vivo with a therapeutic nucleic acid of this invention, and introducing the cell into the organism. The cells are typically isolated or cultured from a patient. Alternatively, the cells can be those stored in a cell bank (e.g., a blood bank).

In one class of embodiments, the vectors of the invention inhibit *Neisseria meningitidis* replication in cells already infected with *Neisseria meningitidis*, in addition to conferring a protective effect to cells which are not infected by *Neisseria meningitidis*. Thus, an organism infected with *Neisseria meningitidis* can be treated for the infection by transducing a population of its cells with a vector encoding an antisense molecule against a selected *Neisseria meningitidis* RNA and introducing the transduced cells back into the patient as described herein. Thus, the present invention provides compositions and methods for protecting cells in culture, ex vivo and in a patient, even when the cells are already infected with the *Neisseria meningitidis.*

The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells. Transduced cells are cultured by means well known in the art. See, also Kuchler et al. (1977) *Biochemical Methods in Cell Culture and Virology*, Kuchler, R. J., Dowden, Hutchinson and Ross, Inc. Mammalian cell systems often will be in the form of monolayers of cells, although mammalian cell suspensions are also used. Illustrative examples of mammalian cell lines include the HEC-1-B cell line, VERO and Hela cells, Chinese hamster ovary (CHO) cell lines, W138, BHK, Cos-7 or MDCK cell lines (see, e.g., Freshney, supra).

In one embodiment, $CD34^+$stem cells are optionally used in ex-vivo procedures for cell transduction and gene therapy. The advantage to using stem cells is that they can be introduced into a mammal (such as the donor of the cells) where they will engraft in the bone marrow and differentiate into many different immune cell types.

In humans, $CD34^+$cells can be obtained from a variety of sources including cord blood, bone marrow, and mobilized peripheral blood. Purification of $CD34^+$cells can be accomplished by antibody affinity procedures. An affinity column isolation procedure for isolating $CD34^+$cells is described by Ho et al. (1995) *Stem Cells* 13 (suppl. 3):100–105. See also, Brenner (1993) *Journal of Hematotherapy* 2:7–17. Yu et al. (1995) PNAS 92:699–703 describe a method of transducing $CD34^+$cells from human fetal cord blood using retroviral vectors.

Rather than using stem cells, T cells or B cells are also used in some embodiments in ex vivo procedures. Several techniques are known for isolating T and B cells. The expression of surface markers facilitates identification and purification of such cells. Methods of identification and isolation of cells include FACS, incubation in flasks with fixed antibodies which bind the particular cell type and panning with magnetic beads.

Administration of Nucleic Acids, Gene Therapy Vectors, Immunogenic Compositions and Transduced Cells Nucleic acids (typically DNA) encoding the polypeptides of the invention are administered to patients to elicit an immune response against the polypeptides which they encode. DNA administered for this purpose is referred to as a "DNA vaccine." Methods of making and administering DNA as vaccines are known, and described, e.g., in Wolff et al., *Science* 247:1465–1468 (1990). The nucleic acids of the invention, including antisense molecules, are also optionally administered to inhibit *Neisseria meningitidis* replication in cells transduced by the vectors, as described supra.

In another aspect, the present invention is directed to administration of immunogenic compositions and vaccines which contain as an active ingredient an immunogenically effective amount of an immunogenic peptide as described herein. The peptide(s) may be introduced into a mammal, including a human. The peptide is optionally linked to a carrier, or is present as a homopolymer or heteropolymer of active peptide units. Polymerization of multiple units of the polypeptides of the invention provides the advantage of increased immunological reaction and, where different peptides are used to make up the polymer, the additional ability to induce antibodies and/or CTLs that react with different antigenic determinants of the virus or tumor cells. Useful carriers are well known in the art, and include, e.g., thyroglobulin, albumins such as human serum albumin, tetanus toxoid, polyamino acids such as poly(lysine: glutamic acid), influenza, hepatitis B virus core protein, hepatitis B virus recombinant vaccine and the like. The vaccines can also contain a physiologically tolerable (acceptable) diluent or excipient such as water, phosphate buffered saline, or saline. The vaccines and immunogenic compositions of the invention further typically include an adjuvant. Adjuvants such as incomplete Freund's adjuvant, aluminum phosphate, aluminum hydroxide, or alum are materials well known in the art. CTL responses can be primed by conjugating peptides of the invention to lipids. Upon immunization with a peptide composition as described herein, the immune system of the host responds to the vaccine by producing antibodies and CTLs specific for the desired antigen, making the host resistant to later infection by *Neisseria meningitidis*, or resistant to developing chronic infection. In addition to the polypeptides herein, known *Neisseria meningitidis* immunogens are optionally present in any immunogenic or vaccine composition, thereby providing an immune response against the both peptides of the invention and known polypeptides. For therapeutic or immunization purposes, the peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (1991) *Nature* 351:456–460. A wide variety of other vectors useful for therapeutic administration or immunization with the peptides of the invention, e.g., *Salmonella typhi* vectors and the like, will be apparent to those skilled in the art from the description herein.

Accordingly, the present invention provides for administration of nucleic acids (e.g., DNA vaccines or cell transformation vectors), polypeptides, immunogenic compositions comprising a polypeptide, vaccine components, and transduced cells (e.g., those made in ex vivo gene therapy or CTL procedures). Administration is by any of the routes normally used for introducing a molecule into ultimate contact with blood or tissue cells. Administration is made in any suitable manner, preferably with pharmaceutically acceptable carriers. Suitable methods of administering nucleic acids, proteins, vaccines, cells and immunogenic compositions in the context of the present invention to a patient are available. Intra-muscular and subcutaneous administration is appropriate for, e.g., vaccines, DNA vaccines, and immunogenic compositions. Parenteral administration such as intravenous administration is a suitable method of administration for transduced cells and cell transformation vectors. Formulations of compositions to be administered can be presented in unit-dose or multi-dose sealed containers, such as ampules and vials.

Pharmaceutically acceptable excipients are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The dose administered to a patient, in the context of the present invention should be sufficient to effect a beneficial therapeutic response in the patient over time, such as a reduction in the level of *Neisseria meningitidis*, or to inhibit infection by *Neisseria meningitidis*. The dose will be determined by the efficacy of the particular vector, nucleic acid or immunogenic composition employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the nucleic acid, immunogenic composition or vector to be administered in the treatment or prophylaxis against *Neisseria meningitidis*, the physician evaluates circulating plasma levels, vector and therepeutic moeity (e.g., anti-*Neisseria* mRNA ribozyme) toxicities, progression of the disease, and the production of anti-*Neisseria meningitidis* antibodies.

For administration, vectors, nucleic acids, immunogenic compositions and transduced cells of the present invention can be administered at a rate determined by the LD-50 of the vector, immunogenic composition, or transduced cell type, and the side-effects of the vector, nucleic acid, immunogenic composition, or cell type at various concentrations, as applied to the mass and overall health of the patient. Administration can be accomplished via single or divided doses. For a typical 70 kg patient, a dose equivalent to approximately 0.1 $\mu$g to 10 mg of vector or nucleic acid are administered. A dose of about 0.1 $\mu$g to 10 mg of most immunogenic compositions will suffice to elicit a protective immune response against *Neisseria meningitidis*. In the case of immunogenic compositions, booster inoculations of the immunogenic composition are occasionally needed. Such booster inoculations are typically administered from once every 5 years up to about four times per year. The need for a booster inoculation can be determined by measuring the level of anti-*Neisseria meningitidis* titer in the serum of the inoculated individual.

Transduced cells are optionally prepared for reinfusion according to established methods. See, Abrahamsen et al.

(1991) *J. Clin. Apheresis* 6:48–53; Carter et al. (1988) *J. Clin. Apheresis* 4:113–117; Aebersold et al. (1988), *J. Immunol. Methods* 112:1–7; Muul et al. (1987) *J. Immunol. Methods* 101:171–181 and Carter et al. (1987) *Transfusion* 27:362–365. In one class of ex vivo procedures, between $1 \times 10^6$ and $1 \times 10^9$ transduced cells (e.g., stem cells, T cells or B cells transduced with vectors encoding a nucleic acid of the invention) are infused intravenously, e.g., over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion may be repeated about every 2 to 3 months for a total of 4 to 6 treatments in a one year period. After the first treatment, infusions can be performed on a outpatient basis at the discretion of the clinician.

If a patient undergoing infusion of a vector, immunogenic composition, or transduced cell develops fevers, chills, or muscle aches, he/she typically receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

The effect of the therapeutic vectors, immunogenic compositions, or transduced cells of the invention on *Neisseria meningitidis* infection and meningitis are measured by monitoring the level of *Neisseria meningitidis* in a patient, or by monitoring the anti-*Neisseria meningitidis* antibody count for the patient over time. Typically, measurements are taken before, during and after the therapeutic or prophylactic regimen.

EXAMPLES

The following examples are provided by way of illustration only and not by way of limitation. Those of skill will readily recognize a variety of noncritical parameters which can be changed or modified to yield essentially similar results.

Example 1

ORF 1 (SEQ ID NO:2 ORF 2 (ORF 2a (SEQ ID NO:4), ORF 2b (SEQ ID NO:5)) and ORF 3 (SEQ ID NO:7) and Invasion Deficient Strains of *Neisseria meningitidis*

Several hundred *N. meningitidis* serogroup B, strain NMB, Tn916 transposon mutants were screened for an increased or decreased ability to attach or invade human endometrial tissue culture (HEC-1-B) cells. Using this approach, we identified and characterized a mutant, VVV6, which showed a >10-fold decrease in its ability to invade HEC-1-B cells compared to the parent NMB (strain) and to an additional well characterized capsule deficient mutant, M7, (Stephens, D. S., et al. (1991), *Infect. Immun.*, 59:4097–4102) (FIG. 2). The results obtained from growth curves and the various controls used in the attachment-invasion assays revealed no significant difference in the growth rate between NMB and VVV6. The results of lipooligosaccharide (LOS) analysis from trains NMB, D1, M7, and VVV6 show that strain D1 cannot sialylate LOS; this deficiency resulted in the loss of the sialilyted LOS band. There are no detectable differences in the LOS profiles from NMB and VVV6. One dimensional SDS-PAGE analysis of outer membrane protein demonstrated that VVV6 had an identical profile to the parent strain. Electron microscopic analysis showed no difference in the quantity or morphology of the observable pili between NMB and VVV6.

Southern analysis on VVV6 genomic DNA digested with EcoRI, HindIII, and Sau3A1 hybridized with a transposon specific probe showed band patterns consistent with that of chromosomal DNA that contains only one copy of the transposon (Swartley, J. S., et al., (1993), *Mol. Microbiol.*, 10:299–310). NMB has no Tn916 transposon inserted in the chromosome, and as expected there is no band observed in the Southern hybridization. In addition, DNA sequence analysis showed that the transposon insertion is of the Class 1 type (Hitchcock et al. (1983)); the entire transposon is inserted and stably maintained in the host genome (Swartley, J. S., et al., (1993), *Mol. Microbiol.*, 10:299–310).

Linkage of the mutant phenotype with the location of the transposon insertion was demonstrated by homologous recombination experiments. Transformation of the parent strain with genomic DNA from mutant VVV6 yielded recombinants that showed the mutant phenotype when tested on the tissue culture monolayer (FIG. 3). Tetracycline resistant back-transformants were obtained at a frequency of $1.3\times10^5$/mgDNA. A total of seven recombinants were tested, all of which showed a decreased ability to invade HEC-1-B cells. The polymerase chain reaction and DNA sequence analysis were used to determine the location of the transposon insertion in each of the transformants. The results showed that the transposon insertions occurred in the exact same position observed in VVV6.

Nucleotide sequence analysis on a 5 kb fragment showed that the Tn916 insertion occurred between two open reading frames (Seq 3 (SEQ ID NO:6), encoding ORF 3 (SEQ ID NO:7), and Seq 2 (SEQ ID NO:3), encoding ORF-2, (ORF 2a (SEQ ID NO:4), ORF 2b (SEQ ID NO:5))). Seq 3 (SEQ ID NO:6) shows no significant homology to any gene in GenBank. Seq 2 (SEQ ID NO:3) is 60%, identical to a gene in *E. coli* with no known function. Further DNA sequence analysis revealed a third open reading frame (Seq 1 (SEQ ID NO:1), encoding ORF 1 (SEQ ID NO:1)) downstream from Seq 2 (SEQ ID NO:3). The nucleotide sequence of Seq 1 (SEQ ID NO:1) is 61% identical to the ftsZ gene from *E. coli*, a gene that has been shown to be essential for cell division and septum formation (See also, Example 2 below).

The recent development of a transposon mutagenesis system (Buddingh, G. J., et al. (1987), *Science*, 86:20–21; Clark et al. (1987)) and the use of more appropriate virulence model systems provide the opportunity to gain new insight into meningococcal disease. We have identified a transposon mutant, VVV6, that shows a decreased ability to invade HEC1-B tissue culture cells compared to the NMB parent strain and a well characterized capsule deficient mutant, M7. Since both NMB and VVV6 show identical replication rates in vitro, the lower numbers of viable counts obtained on the tissue culture assay are most likely due to a diminished ability of VVV6 to invade tissue culture cells.

The VVV6 strain produces identical lipopolysaccharide and SDS-PAGE protein profiles and has similar quantity and type of pili compared to its parental strain. These data in conjunction with the fact that capsule analysis on VVV6 did not reveal any distinguishable differences compared to the parent strain suggests that the mutation responsible for the altered phenotype in mutant VVV6 is not likely due to capsule deficiency or deficiency in any of the other major surface factors. The decreased ability of mutant VVV6 to invade HEC-1-B cells are linked to the disruption of a gene(s) encoding for a factor(s) necessary for recognition of a host cell receptor.

Bacteria and tissue culture cells.

*N. meningitidis* serogroup B strain NMB, and construction of the Tn916-derived mutant library are described elsewhere (Buddingh, G. J., et al., *Science*, 86:20–21). All *Neisseria* strains were maintained on CHOC-II agar (Carr-Scarborough, Atlanta, Ga.). The human endometrial carcinoma cell line, HEC1-B, was maintained by the Biological Products Branch, CDC, Atlanta, Ga. Nearly confluent monolayers were maintained in minimal essential medium (MEM) with 10% fetal bovine serum (Gibco).

Attachment-Invasion Assay

Parent and Tn916 mutant strains were grown from frozen stocks on CHOC-II agar plates to late log phase (18 hours) at 37° C. in 5% $Co_2$. The cells were scraped and resuspended in MEM without serum to an $OD_{600}$ of 0.5 (approximately $10^8$CFU/ml). Monolayers of Hec-1-B cells in 24 well dishes were infected using the resuspended cells. This produced a multiplicity of infection (MOI) of 10:1 (bacteria: host cell). Infection of tissue culture cells was allowed to proceed for 5 hours in 5% $CO_2$ at 37° C. After the infection was completed, each well was washed 5 times with MEM to remove most unattached bacterial cells.

To assay for attachment and invasion, 1 ml of MEM was added to each well. The monolayers were scraped, the suspension was diluted $10^{-3}$, and 100 $\mu$l of this suspension was plated onto CHOCII agar and incubated with the cells at 37° C. overnight. To assay for invasion only, 1 ml of MEM containing gentamicin (125 $\mu$g/ml) was added to each well after the initial 5 hr assay and incubated at 37° C. in 5% $CO_2$ for 90 min. Monolayers were then washed twice with MEM. One-ml of MEM was added to each well and the monolayers were scraped and diluted. Fifty-$\mu$l of the suspension were plated on CHOCII agar plates. Plates were incubated overnight at 37° C. in 5% $CO_2$.

Nasopharyngeal organ cultures.

Construction of the human nasopharyngeal organ culture model has been previously described (Stephens, D. S., et al. (1991), *Rev Infect Dis.*, 13:22–33). The model uses tissues obtained from children undergoing elective adenoidectomy, and allows quantitative and qualitative assessment of the stages of attachment and invasion of *N. meningitidis* to the mucosal surface. This model system was used as a secondary screening method to evaluate the attachment and invasion properties of the mutant(s) identified using the HEC-1B monolayers. Nasopharyngeal organ cultures were incubated with meningococci. After 12 hours of incubation the organ cultures were washed and the associated bacteria were enumerated by homogenization of each organ culture and with subsequent dilution and plating for colony counts.

Outer Membrane Protein Assay.

Meningococcal outer membrane proteins were isolated as described by Clark et al, 1987. This method utilizes differential centrifugation followed by precipitation of outer membrane proteins in 2% sarcosyl. The samples were resolved on SDS-PAGE and the proteins visualized by Coomassie blue or silver stain.

Lipooligosacharide preparation.

LOS was prepared by lysis of bacteria in distilled water followed by proteinase K digestion as described by Hitchcock et al., 1983.

Electron microscopy of pili.

Negative staining grids of meningococci were prepared by fixation in 1% glutaraldehyde (cacodylate buffer) and staining with 1% phosphotungstate, and examination by transmission electron microscopy.

Southern Analysis.

Southern analysis was performed to demonstrate that Tn916 was inserted in the genomic DNA of mutant VVV6. A digoxigenin-labeled plasmid containing transposon Tn916 was used as a probe. Genomic DNA from VVV6 and NMB was isolated and digested with the appropriate restriction enzymes and transferred onto a nylon membrane (Kathariou, S., et al. *Mol. Microbiol.*, 4:729–735). Hybridization was carried out as described in the Genius System manual (Boehringer Mannheim Biochemicals). Briefly, blotted membranes were placed in hybridization tubes containing 20 ml of prehybridization solution (5×SSC, 1% (w/v) blocking reagent, 0.1% N-laurysarcosine, 0.02% SDS) and incubated in a hybrization oven at 50° C. for at least 1 h. The prehybridization solution was replaced with 20 ml of hybridization solution (prehybridization solution containing the digoxygenin-labeled probe) and incubated over night at 52° C. The membrane was washed 2× for 5 min with a 2×SSC buffer containing 0.1% SDS, then washed 3× for 5 min with a buffer consisting of 0.5× SSC and 0.1% SDS. All washes were carried out at room temperature. Colorimetric detection of DNA bands was performed as suggested by the manufacturer.

DNA amplification by PCR.

PCR was used to amplify chromosomal DNA fragments flanking Tn916. The sequences at the ends of the transposon were previously reported (Clewell, D. B., et al. (1988), *J. Bact.*, 170:3046–3052) and were used in the design specific oligonucleotides that served as anchor primers for PCR amplification of adjacent chromosomal DNA. Amplification and isolation of the unknown genomic DNA sequences was performed as previously described (Efrain M. Ribot, et al. (1996), *Gene*. Briefly, mutant genomic DNA was isolated and digested with Sau3A1 restriction endonuclease. This restriction enzyme cuts both arms of the transposon near the transposon-chromosome junction. After digestion was completed, the samples were phenol: chloroform-extracted, ethanol-precipitated and vacuum-desiccated using standard methodologies described by Sambrook et al. The DNA pellet was then resuspended in 20 ml of TE buffer, 2 ml of Sau3A linkers (250 mM/ml) and 2 $\mu$l of 10×T4 DNA ligase buffer and T4 DNA ligase (10 units) were added. The ligation reaction was incubated at room temperature for least 3 hours at. The samples were then phenol: chloroform extracted, ethanol precipitated and resuspended in 20 ml of TE buffer.

The ligation mixture is then subjected to unidirectional PCR amplification (15 cycles:95° C.; 1 min, 52° C.; 1min, 72° C.; 1½ min in 25 ml volumes) of the target DNA using 5' biotin-labeled anchor primers specific for the known sequences of the right arm and left arm of the transposon. The resulting single-stranded PCR product contained the adjacent unknown chromosomal DNA flanked by the remaining portion of the transposon and the sequences corresponding to the ligated linker. The biotin-labeled single-stranded PCR (ssPCR) product containing the flanking chromosomal DNA was captured using streptaiving-coated beads as described by the manufacturer (Dynal AS, Oslo, Norway).

The particle-isolated ssPCR products were subjected to 25 cycles of PCR amplification (94° C.:1 min; 50° C.:30 sec; 72° C.:1½ min in 25 $\mu$l volumes). Transposon and linker specific primers were used for this purpose. The resulting PCR fragments were cloned or sequenced directly as described by Ribot et al., Manuscript submitted for publication. All the oligonucleotide primers used in this study were synthesized by the CDC Biotechnology Core Facility.

DNA sequencing.

Automated DNA sequence analysis was performed using both the Sanger dideoxy method (Amplitaq for sequencing, Perking-Elmer, Foster City, Calif.) and the dye terminator reaction method as described in the ABI instruction manual.

Example 2

The *Neisseria Meningitidis* ftsZ Homologue

The nucleotide sequence of a 1.2 kb DNA fragment of *Neisseria meningitidis* DNA that contains an open reading frame (Seq 1 (SEQ ID NO:1), encoding ORF 1 (SEQ ID NO:2)) that is highly homologous to the corresponding ORF from the *Escherichia coli* ftsZ gene is described in this example. The *E. coli* ftsZ gene codes for a GTP-binding protein essential for septum formation and cell division. The 1.2 kb *N. meningitidis* ORF 1 is 61% identical, at the nucleotide sequence level, to the ftsZ gene of *E. coli* and 50% identical at the amino acid level. The predicted polypeptide contains a glycine-rich stretch of seven amino acids that is identical to the highly conserved GTP-binding domain found in all the ftsZ genes identified thus far. Based on these data, Seq 1 (SEQ ID NO:1) codes for the *N. meningitidis* cell division protein FtsZ.

DNA amplification by PCR.

*Neisseria meningitidis* mutant and wild-type strains were grown on CHOCII agar (Carr-Scarborough, Atlanta, Ga.) plates at 37° C. in 5% $CO_2$ over night. Genomic DNA was isolated using the Isoquick nucleic acid extraction kit (ORCA Research Inc., Bothell, Wash.) under the conditions described by the manufacturer. The procedure used for the amplification of chromosomal DNA fragments was based on a method developed for the rapid amplification of transposon ends (RATE). A modified version of RATE was used to chromosome walk up- land downstream from the transposon insertion site in mutant VVV6. Briefly, genomic DNA was isolated from the bacterial strain and 5 μg digested with the desired restriction endonuclease. The restriction enzyme HindIII was used. After digestion was completed, the sample was phenol: chloroform treated and vacuum using standard methods (Sambrook et al., 1989). The pellet containing the total genomic digest is resuspended in 15 μl of double distilled sterile $H_2O$ and 2 ml of the appropriate linkers (250 mM/ml), 10 units of DNA ligase, and 2.5 μl of 10×T4 DNA ligase buffer added and the sample volume adjusted to 25 ml with double-distilled sterile water. The ligation reaction was then allowed to proceed for at least three hours at room temperature. Construction of the HIEC linker was done by adding equimolar amounts of each oligonucleotide, HEIC1 (ATCTTGAGGTCGACGGGATATCG) (SEQ ID NO:10) and HEIC2 (AATTCGATATCCCGTCGACCTCA) (SEQ ID NO:11), incubating at 90° C. for 5 min and allowing the samples to cool slowly to room temperature. Excess linkers are removed by passing the samples through Microcon 100 filters as described by the manufacturer (Amicon Inc., Beverly, Mass.).

Unidirectional PCR amplification (15 cycles: 95° C.; 1 min, 52° C.;1 min, 72° C.;1½ min in 25 ml volumes) of the target sequence was performed using a 5' biotin=labeled primer/reaction (B800F1 CACATAAGGCGTGGTGGAAG (SEQ ID NO:12) )) specific for the known genomic sequence obtained from previous sequencing reactions. This unidirectional amplification reaction yields single-stranded DNA molecules containing the chromosomal target sequence, the adjacent unknown chromosomal DNA, and the linker. Streptavidin coated beads (Dynal AS, Oslo, Norway) were used to capture the PCR-amplified biotin-labeled single-stranded products following the manufacturers recommendations. Aliqots of the purified single-stranded PCR products were then subjected to 30 cycles of PCR amplification (94° C.:1 min; 42° C.:30 sec; 72° C.:1½ min in 25 ml volumes), using a nested primer specific for the for the known sequence (800F8 CTCCCAAACCGGA-CAAACCG (SEQ ID NO:13)) and a primer corresponding to the ligated linker (HIEC2). A 5 ml aliquot of each of the resulting double-stranded PCR products was loaded onto a 0.8% agarose gel to determine product size and purity (data not shown). Selected products were then subjected to automated DNA sequence analysis using primers specific to both the known genomic (800F9 GTCAAGTACGGACTGAT-TGTCG (SEQ ID NO:14)) sequence and the HEIC2 linker primer.

DNA sequencing.

Automated DNA sequence analysis of PCR amplified fragments was performed using the dye terminator reaction method as described in the ABI-373 instruction manual (Perking-Elmer, Foster City, Calif.). Computer assisted analysis was performed using the Wisconsin Sequence Analysis Package (GCG) (Madison, Wis.) and DNASIS, (National Bioscience, Inc, Plymouth, Minn.).

The Tn916 transposon mutant of *N. meningitidis*, serogroup B, strain NMB, demonstrated a significant decrease in its ability to invade human epithelial tissue culture cells compared to control strains. Sequencing analysis on VVV6 genomic DNA indicated that the transposon insertion occurred between two possible open reading frames (Seq 3 (SEQ ID NO:6) and Seq 2 (SEQ ID NO:3)) (FIG. 1). Further DNA sequence analysis on the region downstream from Seq 2 (SEQ ID NO:3) revealed a another ORF (Seq 1 (SEQ ID NO:1)). Nucleotide sequence comparison of this ORF (Seq 1 (SEQ ID NO:1)) using the FASTA algorithm of the GCG Wisconsin package shows that the nucleotide sequence of Seq 1 (SEQ ID NO:1) is over 61% identical to the *E. coli* essential cell division gene ftsZ. All ftsZ genes identified to date show a high degree of homology. We have also identified both a possible ribosome binding site and start codon for this ORF (Seq 1 (SEQ ID NO:1)) and there are two possible stop codons at nucleotide positions 1100 and 1148. Primer extension and S1 nuclease protection studies are used to determine the precise location of promoter regions and termination sequences of Seq 1 (SEQ ID NO:1), Seq 2 (SEQ ID NO:3) and Seq 3 (SEQ ID NO:6).

The amino acid sequence of the ORF 1 polypeptide (SEQ ID NO:1) is 50% identical to the FtsZ protein from *E. coli* and *B. subtilis*. Furthermore, the amino acid sequence of the *N. meningitidis* FtsZ protein contains the highly conserved GTP-binding domain present in all the FtsZ proteins identified thus far (de Boer, et al. (1992) *Nature* 359:254–56; Mukherjee, et al. (1993) *Proc. Natl. Acad. Sci. USA*. 90:1053–57; Beall, et al. (1988) *J. Bacteriol*. 170:4855–4864).

A highly conserved glycine-rich stretch of amino acids (GGGTGTG (SEQ ID NO:15)) has been found in all the FtsZ proteins identified so far (Corton, et al. (1987) *J. Bacteriol*. 169:1–7; de Boer, et al. (1992) *Nature* 359:254–56). As can be observed from amino acid residues at approximately 109 to 115 of ORF 1 (SEQ ID NO:1), the amino acid sequence of the polypeptide encoded by ORF 1 (SEQ ID NO:1) also contains this highly conserved domain. This provides additional evidence that the gene product encoded by the Neisseria ORF is the homolog of the FtsZ protein from *E. coli*. In vitro assays indicate that this glycine-rich sequence contains a domain with GTP/GDP-binding activity (Corton, et al. (1987) *J. Bacteriol*. 169:1–7; de Boer, et al. (1992) *Nature* 359:254–56; Mukherjee, et al.

(1993) *Proc. Natl. Acad. Sci. USA.* 90:1053–57). *Escherichia coli* cells have been characterized that carry mutations within this amino acid stretch that result in a cell division deficient phenotype. The inability of such mutants to divide has been linked to reduced GTPase activity (Cook, et al. (1994) *Mol. Microbiol.* 14:485–495; Ricard, et al. (1973) *J. Bacteriol.* 116:314–322). It has been demonstrated that the *E. coli* functional unit of FtsZ consists of multiple copies of FtsZ assembled together in a multimeric complex. It appears that the GTPase activity is required for the assembly of such a complex. If a mutated FtsZ has a decreased ability to bind GTP, complex formation will not occur as it would under normal conditions, thus diminishing the cell's ability to divide. This stretch of amino acids is not only conserved among the eubacteria (Lutkenhaus, et al. (1980) *J. Bacteriol.* 142:615–620; Miyakawa, et al. (1972) *J. Bacteriol* 112:959–958), but is also remarkably similar to the a-, b-, and g-tubulins from eukaryotic cells (Gill, et al. (1986) *Mol. Gen. Genet.* 205:134–145). FtsZ may be the predecessor of the more evolutionarily recent tubulin (Bermudez, et al. (1994) *Microbiol. Rev.* 58:387–400). This hypothesis is supported by the recent discovery of an ftsZ homolog gene from the archaebacterium *Halobacterium salinarum*. Amino acid sequence aligment of the *H. salinarum* FtsZ showed remarkable similarity to the FtsZ proteins from eubacteria and tubulins from eucaryotic cells.

In *E. coli*, ftsZ is preceded by the ftsA gene and followed by the envA gene. The nucleotide sequence of a 225 bp long segment of DNA upstream of ORF 1 (SEQ ID NO:7) from *N. meningitidis*, NMB, was obtained, but failed to reveal any significant homology to the ftsA gene from *E. coli*. The DNA sequence downstream of the *Neisseria* ftsZ also revealed no homology to the *E. coli* envA gene. This is not surprising since the DNA regions flanking the ftsZ gene from organisms such as *Bacillus subtilis* (Beall, et al. (1988) *J. Bacteriol.* 170:4855–4864), *Streptomyces coleicolor* (McCormick, et al. (1994) *Mol. Microbiol.* 14:243–254), and *H. salinarum* (Margolin, et al. (1996) *J. Bacteriol.* 178:1320–1327) do not show the same genetic map observed in *E. coli.*

While a hypothetical ribosome binding site (RBS) and start codon (ATG) were found, no obvious consensus promoter sequence was identified in association with the ftsZ-homolog gene. This ORF may be controlled by a promoter located elsewhere in the DNA region upstream; in *E. coli*, the promoter controlling expression of ftsZ is found upstream within the ftsA gene. Primer extension analysis ultimately defines the start site of transcription. In addition, there is no obvious termination sequence at the end of the ORF of the ftsZ-homolog, suggesting that the gene is expressed as part of a polycistronic message in *Neisseria meningitidis*. Interestingly, computer analysis revealed a strong termination loop at the end of Seq 2 (SEQ ID NO:3); this may indicate the end of transcription of the polygenic mRNA. Again, this genetic arrangement bears a strong resemblance to the ftsZ gene region from *E. coli.*, which consists of an operon-like structure containing the ftsQ, ftsA, ftsZ, and envA genes.

Discussion of the Accompanying Sequence Listing

SEQ ID NO:8 provides the sequence of Seq 4. This sequence encompasses Seq 1, Seq 2, and Seq 3, which are additionally provided at SEQ ID NO:1, SEQ ID NO:3, and SEQ ID NO:6, respectively. The information for the nucleic acid sequences are presented as DNA sequence information. One of skill will readily understand that portions of the sequences also describe RNAs encoded by the sequence (e.g, by substitution of T residues with corresponding U residues), and a variety of conservatively modified variations, including silent substitutions of the sequences. While only a single strand of sequence information is shown, one of skill will immediately appreciate that the complete corresponding complementary sequence is fully described by comparison to the given sequences.

SEQ ID NO:2, SEQ ID NO:4, SEQ ID NO:5, and SEQ ID NO:7 provide the amino acid sequences of ORF 1, ORF 2a, ORF 2b, and ORF 3, respectively. A variety of conservatively modified variations of the amino acid sequences provided will be apparent to one of skill, and are described herein. One of skill will also recognize that a variety of nucleic acid sequences encode each of the polypeptides due to the codon degeneracy present in the genetic code. Each of the nucleic acids which encodes the given polypeptide is described by comparison to the amino acid sequence and translation via the genetic code.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. An isolated nucleic acid encoding a polypeptide selected from the group of polypeptides consisting of SEQ ID NO:2, SEQ ID NO:4, SEQ ID NO:5 and SEQ ID NO:7.

2. The nucleic acid of claim 1, wherein the nucleic acid is selected from the group consisting of SEQ ID NO:1, SEQ ID NO:3 and SEQ ID NO:6.

3. An isolated nucleic acid which hybridizes under high stringency conditions to a nucleic acid selected from the group consisting of SEQ ID NO:1, SEQ ID NO:3, and SEQ ID NO:6 wherein the high stringency wash conditions are selected to be about 5° C. lower than the thermal melting point ($T_m$) for the specific sequence at a defined ionic strength and pH.

4. The isolated nucleic acid of claim 3 wherein the nucleic acid is at least 20 nucleotides in length.

5. An isolated nucleic acid which hybridizes under high stringency conditions to SEQ ID NO:8 wherein the stringency wash conditions are selected to be about 5° C. lower than the thermal melting point ($T_m$) for the specific sequence at a defined ionic strength and pH.

6. A recombinant expression vector comprising the nucleic acid of claim 5 operably linked to a promoter.

7. The nucleic acid of claim 6, wherein the nucleic acid, when transduced into a cell, is expressed under suitable conditions to produce a polypeptide selected from the group of polypeptides consisting of SEQ ID NO:2, SEQ ID NO:4, SEQ ID NO:5, and SEQ ID NO:7.

* * * * *

SEQUENCE LISTING

```
<160> NUMBER OF SEQ ID NOS: 15

<210> SEQ ID NO 1
<211> LENGTH: 1185
<212> TYPE: DNA
<213> ORGANISM: Artificial Sequence
<220> FEATURE:
<223> OTHER INFORMATION: Description of Artificial Sequence; Note =
      synthetic construct
<221> NAME/KEY: CDS
<222> LOCATION: (17)...(1102)
<221> NAME/KEY: misc_feature
<222> LOCATION: (1)...(1185)
<223> OTHER INFORMATION: Note:/Seq 1 = position 223 through position
      1407 of Seq 4
<221> NAME/KEY: misc_feature
<222> LOCATION: (17)...(1102)
<223> OTHER INFORMATION: product = ORF 1
      Note:/  = ORF 1 CDS = position 238 through
``` position 1324 of Seq 4

<400> SEQUENCE: 1

```
gagcaggagt ttttga atg gaa ttt gtt tac gac gtg gca gaa tcg gca gtc          52
               Met Glu Phe Val Tyr Asp Val Ala Glu Ser Ala Val
                 1               5                  10 agc cct gcg gtg att aaa gta atc ggc ttg ggc ggc ggc ggt tgc aat           100
Ser Pro Ala Val Ile Lys Val Ile Gly Leu Gly Gly Gly Gly Cys Asn
        15                  20                  25 gca tcc aat aac atg gtt gcc aac aat gtg cgc ggt gtg gag ttt atc          148
Ala Ser Asn Asn Met Val Ala Asn Asn Val Arg Gly Val Glu Phe Ile
 30                  35                  40 agt gcc aat acg gat gcg cag tct ctg gca aaa aac cat gcg gcg aag          196
Ser Ala Asn Thr Asp Ala Gln Ser Leu Ala Lys Asn His Ala Ala Lys
 45                  50                  55                  60 aga atc cag ttg ggt acg aat ctg aca cgc ggt ttg ggc gcg ggc gcg          244
Arg Ile Gln Leu Gly Thr Asn Leu Thr Arg Gly Leu Gly Ala Gly Ala
             65                  70                  75 aat ccc gat atc ggc cgt gcg gca gcc cag gaa gac cgg gaa gcc att          292
Asn Pro Asp Ile Gly Arg Ala Ala Ala Gln Glu Asp Arg Glu Ala Ile
         80                  85                  90 gaa gaa gcc att cgc ggt gcg aat atg ctg ttt atc acg acc ggt atg          340
Glu Glu Ala Ile Arg Gly Ala Asn Met Leu Phe Ile Thr Thr Gly Met
             95                 100                 105 ggc ggc ggt acc ggt acc ggt tcc gcg ccg gtt gtt gct gag att gcc          388
Gly Gly Gly Thr Gly Thr Gly Ser Ala Pro Val Val Ala Glu Ile Ala
    110                 115                 120 aag tct ttg ggc att ctg acc gtt gcc gtg gtt acc cga ccg ttc gca          436
Lys Ser Leu Gly Ile Leu Thr Val Ala Val Val Thr Arg Pro Phe Ala
125                 130                 135                 140 tat gaa ggt aag cgc gtc cat gtc gca cag gca ggg ttg gaa cag ttg          484
Tyr Glu Gly Lys Arg Val His Val Ala Gln Ala Gly Leu Glu Gln Leu
                145                 150                 155 aaa gaa cac gtc gat tcg ctg att atc atc ccg aac gac aaa ctg atg          532
Lys Glu His Val Asp Ser Leu Ile Ile Ile Pro Asn Asp Lys Leu Met
            160                 165                 170 act gca ttg ggt gaa gac gta acg atg cgc gaa gcc ttc cgt gcc gcc          580
Thr Ala Leu Gly Glu Asp Val Thr Met Arg Glu Ala Phe Arg Ala Ala
        175                 180                 185 gac aat gta ttg cgc gat gcg gtc gca ggc att tcc gaa gtg gta act          628
Asp Asn Val Leu Arg Asp Ala Val Ala Gly Ile Ser Glu Val Val Thr
    190                 195                 200 tgc ccg agc gaa atc atc aac ctc gac ttt gcc gac gtg aaa acc gtg          676
Cys Pro Ser Glu Ile Ile Asn Leu Asp Phe Ala Asp Val Lys Thr Val
205                 210                 215                 220 atg agc aac cgc ggt atc gct atg atg ggt tcg ggt tat gcc caa ggt          724
Met Ser Asn Arg Gly Ile Ala Met Met Gly Ser Gly Tyr Ala Gln Gly
                225                 230                 235 atc gac cgt gcg cgt atg gcg acc gac cag gcc att tcc agt ccg ctg          772
Ile Asp Arg Ala Arg Met Ala Thr Asp Gln Ala Ile Ser Ser Pro Leu
            240                 245                 250 ctg gac gat gta acc ttg gac gga gcg cgc ggt gtg ctg gtc aat att          820
Leu Asp Asp Val Thr Leu Asp Gly Ala Arg Gly Val Leu Val Asn Ile
        255                 260                 265 acg act gct ccg ggt tgc ttg aaa atg tcc gag ttg tcc gaa gtc atg          868
Thr Thr Ala Pro Gly Cys Leu Lys Met Ser Glu Leu Ser Glu Val Met
    270                 275                 280 aaa atc gtc aac caa agc gcg cat ccc gat ttg gaa tgc aaa ttc ggt          916
Lys Ile Val Asn Gln Ser Ala His Pro Asp Leu Glu Cys Lys Phe Gly
285                 290                 295                 300
```

```
gct gct gaa gac gag acc atg agc gaa gat gcc atc cgg att acc att    964
Ala Ala Glu Asp Glu Thr Met Ser Glu Asp Ala Ile Arg Ile Thr Ile
            305                 310                 315 atc gct acc ggt ctg aaa gaa aaa ggc gcg gtc gat ttt gtt ccg gca   1012
Ile Ala Thr Gly Leu Lys Glu Lys Gly Ala Val Asp Phe Val Pro Ala
        320                 325                 330 agg gag gta gaa gcg gtt gcc ccg tcc aaa cag gag caa agc cac aat   1060
Arg Glu Val Glu Ala Val Ala Pro Ser Lys Gln Glu Gln Ser His Asn
        335                 340                 345 gtc gaa ggt aga tcc gca cca atc gcg gta tcc gca cga tga           1102
Val Glu Gly Arg Ser Ala Pro Ile Ala Val Ser Ala Arg  *
350                 355                 360 accttaccgc tgcggatttc gacaatcagt ccgtacttga cgacttgaaa tccctgcgat  1162
tttgcgtcgt caacacaatt cag                                          1185

<210> SEQ ID NO 2
<211> LENGTH: 361
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 2

Met Glu Phe Val Tyr Asp Val Ala Glu Ser Ala Val Ser Pro Ala Val
 1               5                  10                  15

Ile Lys Val Ile Gly Leu Gly Gly Gly Cys Asn Ala Ser Asn Asn
            20                  25                  30

Met Val Ala Asn Asn Val Arg Gly Val Glu Phe Ile Ser Ala Asn Thr
        35                  40                  45

Asp Ala Gln Ser Leu Ala Lys Asn His Ala Ala Lys Arg Ile Gln Leu
    50                  55                  60

Gly Thr Asn Leu Thr Arg Gly Leu Gly Ala Gly Ala Asn Pro Asp Ile
65                  70                  75                  80

Gly Arg Ala Ala Ala Gln Glu Asp Arg Glu Ala Ile Glu Glu Ala Ile
                85                  90                  95

Arg Gly Ala Asn Met Leu Phe Ile Thr Thr Gly Met Gly Gly Gly Thr
            100                 105                 110

Gly Thr Gly Ser Ala Pro Val Val Ala Glu Ile Ala Lys Ser Leu Gly
        115                 120                 125

Ile Leu Thr Val Ala Val Val Thr Arg Pro Phe Ala Tyr Glu Gly Lys
    130                 135                 140

Arg Val His Val Ala Gln Ala Gly Leu Glu Gln Leu Lys Glu His Val
145                 150                 155                 160

Asp Ser Leu Ile Ile Ile Pro Asn Asp Lys Leu Met Thr Ala Leu Gly
                165                 170                 175

Glu Asp Val Thr Met Arg Glu Ala Phe Arg Ala Ala Asp Asn Val Leu
            180                 185                 190

Arg Asp Ala Val Ala Gly Ile Ser Glu Val Val Thr Cys Pro Ser Glu
        195                 200                 205

Ile Ile Asn Leu Asp Phe Ala Asp Val Lys Thr Val Met Ser Asn Arg
    210                 215                 220

Gly Ile Ala Met Met Gly Ser Gly Tyr Ala Gln Gly Ile Asp Arg Ala
225                 230                 235                 240

Arg Met Ala Thr Asp Gln Ala Ile Ser Ser Pro Leu Leu Asp Asp Val
                245                 250                 255
```

-continued

```
Thr Leu Asp Gly Ala Arg Gly Val Leu Val Asn Ile Thr Thr Ala Pro
            260                 265                 270
Gly Cys Leu Lys Met Ser Glu Leu Ser Glu Val Met Lys Ile Val Asn
        275                 280                 285
Gln Ser Ala His Pro Asp Leu Glu Cys Lys Phe Gly Ala Ala Glu Asp
    290                 295                 300
Glu Thr Met Ser Glu Asp Ala Ile Arg Ile Thr Ile Ala Thr Gly
305                 310                 315                 320
Leu Lys Glu Lys Gly Ala Val Asp Phe Val Pro Ala Arg Glu Val Glu
                325                 330                 335
Ala Val Ala Pro Ser Lys Gln Glu Gln Ser His Asn Val Glu Gly Arg
            340                 345                 350
Ser Ala Pro Ile Ala Val Ser Ala Arg
            355                 360

<210> SEQ ID NO 3
<211> LENGTH: 960
<212> TYPE: DNA
<213> ORGANISM: Artificial Sequence
<220> FEATURE:
<223> OTHER INFORMATION: Description of Artificial Sequence; Note =
      synthetic construct
<221> NAME/KEY: misc_feature
<222> LOCATION: (1)...(960)
<223> OTHER INFORMATION: Note:/ Seq 2 = positions 1921 through 2880
      of Seq 4
<221> NAME/KEY: misc_feature
<222> LOCATION: (39)...(941)
<223> OTHER INFORMATION: /product = ORF 2a
      Note:/ ORF 2 protein variant using alternate start
      site at position 39 of Seq 2 (position 1959
      through position 2861 of Seq 4)
<221> NAME/KEY: misc_feature
<222> LOCATION: (51)...(941)
<223> OTHER INFORMATION: / product = ORF 2b
      Note:/ ORF 2 protein variant using alternate start
      site at position 51 of Seq 2 (position 1971
      through position 2861 of Seq 4)

<400> SEQUENCE: 3 tttttttaaag tcagggaaat gctgtcaacg cactgcct atg ggt ttg aaa atg tcg     56
                                          Met Gly Leu Lys Met Ser
                                            1               5 att gct gcc ggt atc ggt ttg ttt ttg gca ctg att tcc ctg aaa ggc       104
Ile Ala Ala Gly Ile Gly Leu Phe Leu Ala Leu Ile Ser Leu Lys Gly
            10                  15                  20 gca ggc cat tat cgt tgc caa tcc ggc aac ctt ggt cgg ttt ggg cga       152
Ala Gly His Tyr Arg Cys Gln Ser Gly Asn Leu Gly Arg Phe Gly Arg
        25                  30                  35 tat tca tca gcc gtc cgc gtt gtt ggc act gtt cgg ttt tgc tat ggt       200
Tyr Ser Ser Ala Val Arg Val Val Gly Thr Val Arg Phe Cys Tyr Gly
    40                  45                  50 ggt cgt att ggg aca ttt ccg cgt tca agg cgc aac atc atc acc atc       248
Gly Arg Ile Gly Thr Phe Pro Arg Ser Arg Arg Asn Ile Ile Thr Ile
55                  60                  65                  70 ttg acc att acc gtc att gcc agc ctg atg ggt ttg aat gaa ttt cac       296
Leu Thr Ile Thr Val Ile Ala Ser Leu Met Gly Leu Asn Glu Phe His
                75                  80                  85 ggc atc atc ggc gaa gta ccg agc att gcg ccg act ttt atg cag atg       344
Gly Ile Ile Gly Glu Val Pro Ser Ile Ala Pro Thr Phe Met Gln Met
            90                  95                  100 gat ttt gaa ggc ctg ttt acc gtc agc tgg tca gtg att ttc gtc ttc       392
Asp Phe Glu Gly Leu Phe Thr Val Ser Trp Ser Val Ile Phe Val Phe
```

```
ttc ttg gtc gat cta ttt gac agt acc gga acg ctg gtc ggc ata tcc    440
Phe Leu Val Asp Leu Phe Asp Ser Thr Gly Thr Leu Val Gly Ile Ser
    120             125                 130 cac cgt gcc ggg ctg ctg gtg gac ggt aag ctg ccc cgc ctg aaa cgc    488
His Arg Ala Gly Leu Leu Val Asp Gly Lys Leu Pro Arg Leu Lys Arg
135             140                 145                 150 gca ctg ctt gca gac tct acc gcc att atg gca ggt gcg gct ttg ggt    536
Ala Leu Leu Ala Asp Ser Thr Ala Ile Met Ala Gly Ala Ala Leu Gly
                155                 160                 165 act tct tcc acc acg cct tat gtg gaa agc gcg gcg ggc gta tcg gca    584
Thr Ser Ser Thr Thr Pro Tyr Val Glu Ser Ala Ala Gly Val Ser Ala
        170                 175                 180 ggc gga cgg acc ggc ctg acg gcg gtt acc gtc ggc gta ttg atg ctc    632
Gly Gly Arg Thr Gly Leu Thr Ala Val Thr Val Gly Val Leu Met Leu
            185                 190                 195 gcc tgc ctg atg ttt tca cct ttg gcg aaa agt gtt ccc gct ttt ggc    680
Ala Cys Leu Met Phe Ser Pro Leu Ala Lys Ser Val Pro Ala Phe Gly
200                 205                 210 acc gcg ccc gcc ctg ctt tat gtc ggc acg cag atg ctc cgc agt gcg    728
Thr Ala Pro Ala Leu Leu Tyr Val Gly Thr Gln Met Leu Arg Ser Ala
215                 220                 225                 230 agg gat att gat tgg gac gat atg acg gaa gcc gca ccc gca ttc ctg    776
Arg Asp Ile Asp Trp Asp Asp Met Thr Glu Ala Ala Pro Ala Phe Leu
                235                 240                 245 acc att gtc ttc atg ccg ttt acc tat tcg att gca gac ggc atc gcc    824
Thr Ile Val Phe Met Pro Phe Thr Tyr Ser Ile Ala Asp Gly Ile Ala
            250                 255                 260 ttc ggc ttc atc agc tat gcc gtg gtt aaa ctt tta tgc cgc cgc acc    872
Phe Gly Phe Ile Ser Tyr Ala Val Val Lys Leu Leu Cys Arg Arg Thr
        265                 270                 275 aaa gac gtt ccg cct atg gaa tgg gtt gtt gcc gta ttg tgg gca ctg    920
Lys Asp Val Pro Pro Met Glu Trp Val Val Ala Val Leu Trp Ala Leu
    280                 285                 290 aaa ttc tgg tat ttg ggc tga ttgattcgat attaaaaat                   960
Lys Phe Trp Tyr Leu Gly  *
295             300

<210> SEQ ID NO 4
<211> LENGTH: 300
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 4

Met Gly Leu Lys Met Ser Ile Ala Ala Gly Ile Gly Leu Phe Leu Ala
  1               5                  10                  15

Leu Ile Ser Leu Lys Gly Ala Gly His Tyr Arg Cys Gln Ser Gly Asn
                 20                  25                  30

Leu Gly Arg Phe Gly Arg Tyr Ser Ala Val Arg Val Val Gly Thr
                 35                  40                  45

Val Arg Phe Cys Tyr Gly Gly Arg Ile Gly Thr Phe Pro Arg Ser Arg
     50                  55                  60

Arg Asn Ile Ile Thr Ile Leu Thr Ile Thr Val Ile Ala Ser Leu Met
 65                  70                  75                  80

Gly Leu Asn Glu Phe His Gly Ile Ile Gly Glu Val Pro Ser Ile Ala
                 85                  90                  95
```

```
Pro Thr Phe Met Gln Met Asp Phe Glu Gly Leu Phe Thr Val Ser Trp
            100                 105                 110
Ser Val Ile Phe Val Phe Phe Leu Val Asp Leu Phe Asp Ser Thr Gly
            115                 120                 125
Thr Leu Val Gly Ile Ser His Arg Ala Gly Leu Leu Val Asp Gly Lys
    130                 135                 140
Leu Pro Arg Leu Lys Arg Ala Leu Leu Ala Asp Ser Thr Ala Ile Met
145                 150                 155                 160
Ala Gly Ala Ala Leu Gly Thr Ser Ser Thr Thr Pro Tyr Val Glu Ser
                165                 170                 175
Ala Ala Gly Val Ser Ala Gly Gly Arg Thr Gly Leu Thr Ala Val Thr
            180                 185                 190
Val Gly Val Leu Met Leu Ala Cys Leu Met Phe Ser Pro Leu Ala Lys
            195                 200                 205
Ser Val Pro Ala Phe Gly Thr Ala Pro Ala Leu Leu Tyr Val Gly Thr
    210                 215                 220
Gln Met Leu Arg Ser Ala Arg Asp Ile Asp Trp Asp Met Thr Glu
225                 230                 235                 240
Ala Ala Pro Ala Phe Leu Thr Ile Val Phe Met Pro Phe Thr Tyr Ser
                245                 250                 255
Ile Ala Asp Gly Ile Ala Phe Gly Phe Ile Ser Tyr Ala Val Val Lys
            260                 265                 270
Leu Leu Cys Arg Arg Thr Lys Asp Val Pro Pro Met Glu Trp Val Val
    275                 280                 285
Ala Val Leu Trp Ala Leu Lys Phe Trp Tyr Leu Gly
            290                 295                 300

<210> SEQ ID NO 5
<211> LENGTH: 296
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 5

Met Ser Ile Ala Ala Gly Ile Gly Leu Phe Leu Ala Leu Ile Ser Leu
1               5                   10                  15
Lys Gly Ala Gly His Tyr Arg Cys Gln Ser Gly Asn Leu Gly Arg Phe
            20                  25                  30
Gly Arg Tyr Ser Ser Ala Val Arg Val Gly Thr Val Arg Phe Cys
        35                  40                  45
Tyr Gly Gly Arg Ile Gly Thr Phe Pro Arg Ser Arg Asn Ile Ile
    50                  55                  60
Thr Ile Leu Thr Ile Thr Val Ile Ala Ser Leu Met Gly Leu Asn Glu
65                  70                  75                  80
Phe His Gly Ile Ile Gly Glu Val Pro Ser Ile Ala Pro Thr Phe Met
                85                  90                  95
Gln Met Asp Phe Glu Gly Leu Phe Thr Val Ser Trp Ser Val Ile Phe
            100                 105                 110
Val Phe Phe Leu Val Asp Leu Phe Asp Ser Thr Gly Thr Leu Val Gly
            115                 120                 125
Ile Ser His Arg Ala Gly Leu Leu Val Asp Gly Lys Leu Pro Arg Leu
    130                 135                 140
Lys Arg Ala Leu Leu Ala Asp Ser Thr Ala Ile Met Ala Gly Ala Ala
145                 150                 155                 160
```

-continued

```
Leu Gly Thr Ser Ser Thr Thr Pro Tyr Val Glu Ser Ala Ala Gly Val
            165                 170                 175

Ser Ala Gly Gly Arg Thr Gly Leu Thr Ala Val Thr Val Gly Val Leu
        180                 185                 190

Met Leu Ala Cys Leu Met Phe Ser Pro Leu Ala Lys Ser Val Pro Ala
    195                 200                 205

Phe Gly Thr Ala Pro Ala Leu Leu Tyr Val Gly Thr Gln Met Leu Arg
210                 215                 220

Ser Ala Arg Asp Ile Asp Trp Asp Asp Met Thr Glu Ala Ala Pro Ala
225                 230                 235                 240

Phe Leu Thr Ile Val Phe Met Pro Phe Thr Tyr Ser Ile Ala Asp Gly
            245                 250                 255

Ile Ala Phe Gly Phe Ile Ser Tyr Ala Val Val Lys Leu Leu Cys Arg
            260                 265                 270

Arg Thr Lys Asp Val Pro Pro Met Glu Trp Val Val Ala Val Leu Trp
        275                 280                 285

Ala Leu Lys Phe Trp Tyr Leu Gly
    290                 295

<210> SEQ ID NO 6
<211> LENGTH: 457
<212> TYPE: DNA
<213> ORGANISM: Artificial Sequence
<220> FEATURE:
<221> NAME/KEY: CDS
<222> LOCATION: (17)...(457)
<221> NAME/KEY: misc_feature
<222> LOCATION: (1)...(457)
<223> OTHER INFORMATION: Note:/ n = a,t,c, or g
<221> NAME/KEY: misc_feature
<222> LOCATION: (1)...(457)
<223> OTHER INFORMATION: Note:/ Seq 3 = position 3381 through position
      3837 of Seq 4
<221> NAME/KEY: misc_feature
<222> LOCATION: (17)...(457)
<223> OTHER INFORMATION: / product = ORF 3
      Note:/ ORF 3 CDS = position 3397 through position
      3837 of Seq 4

<400> SEQUENCE: 6
taatgattgg attggg atg ccc gac gcg tcg gat ggc tgt gtt ttg ccg tcc     52
              Met Pro Asp Ala Ser Asp Gly Cys Val Leu Pro Ser
                1               5                   10 gaa tgt gat gga agc ctg tcc ata ctg aaa aaa agt cta tan agg aga      100
Glu Cys Asp Gly Ser Leu Ser Ile Leu Lys Lys Ser Leu Xaa Arg Arg
        15                  20                  25 aat atg atg agt caa cac tct gcc gga gca cgt ttc cgc caa gcc gtg     148
Asn Met Met Ser Gln His Ser Ala Gly Ala Arg Phe Arg Gln Ala Val
 30                  35                  40 aaa gaa tcg aat ccg ctt gcc gtc gcc ggt tgc gtc aat gct tat ttt     196
Lys Glu Ser Asn Pro Leu Ala Val Ala Gly Cys Val Asn Ala Tyr Phe
 45                  50                  55                  60 gca cga ttg gcc acc caa agc ggt ttc aaa gcc atc tat ctg tct ggc     244
Ala Arg Leu Ala Thr Gln Ser Gly Phe Lys Ala Ile Tyr Leu Ser Gly
             65                  70                  75 ggc ggc gtg gca gcc tgt tct tgc ggt atc cct gat ttg ggc att acc     292
Gly Gly Val Ala Ala Cys Ser Cys Gly Ile Pro Asp Leu Gly Ile Thr
         80                  85                  90 aca atg gaa gat gtg ctg atc gac gca cga cgc att acg gac aac gtg     340
Thr Met Glu Asp Val Leu Ile Asp Ala Arg Arg Ile Thr Asp Asn Val
     95                 100                 105
```

```
gat ncg cct ctg ctg gtg gac atc gat gtg ggt tgg ggc ggt gca ttc    388
Asp Xaa Pro Leu Leu Val Asp Ile Asp Val Gly Trp Gly Gly Ala Phe
    110             115                 120 aat att gcc cgt acc att cgc aac ttt gaa cgc gcc ggt gtt gca gcg    436
Asn Ile Ala Arg Thr Ile Arg Asn Phe Glu Arg Ala Gly Val Ala Ala
125             130                 135                 140 gtt cac atc gaa gat cag gta                                        457
Val His Ile Glu Asp Gln Val
                145

<210> SEQ ID NO 7
<211> LENGTH: 147
<212> TYPE: PRT
<213> ORGANISM: Artificial Sequence
<220> FEATURE:
<223> OTHER INFORMATION: Description of Artificial Sequence; Note =
      synthetic construct
<221> NAME/KEY: VARIANT
<222> LOCATION: (1)...(147)
<223> OTHER INFORMATION: Note: Xaa = any amino acid

<400> SEQUENCE: 7

Met Pro Asp Ala Ser Asp Gly Cys Val Leu Pro Ser Glu Cys Asp Gly
 1               5                  10                  15

Ser Leu Ser Ile Leu Lys Lys Ser Leu Xaa Arg Arg Asn Met Met Ser
            20                  25                  30

Gln His Ser Ala Gly Ala Arg Phe Arg Gln Ala Val Lys Glu Ser Asn
        35                  40                  45

Pro Leu Ala Val Ala Gly Cys Val Asn Ala Tyr Phe Ala Arg Leu Ala
    50                  55                  60

Thr Gln Ser Gly Phe Lys Ala Ile Tyr Leu Ser Gly Gly Gly Val Ala
65                  70                  75                  80

Ala Cys Ser Cys Gly Ile Pro Asp Leu Gly Ile Thr Thr Met Glu Asp
                85                  90                  95

Val Leu Ile Asp Ala Arg Arg Ile Thr Asp Asn Val Asp Xaa Pro Leu
            100                 105                 110

Leu Val Asp Ile Asp Val Gly Trp Gly Gly Ala Phe Asn Ile Ala Arg
        115                 120                 125

Thr Ile Arg Asn Phe Glu Arg Ala Gly Val Ala Ala Val His Ile Glu
    130                 135                 140

Asp Gln Val
145

<210> SEQ ID NO 8
<211> LENGTH: 5416
<212> TYPE: DNA
<213> ORGANISM: Artificial Sequence
<220> FEATURE:
<223> OTHER INFORMATION: Description of Artificial Sequence; Note =
      synthetic construct
<221> NAME/KEY: misc_feature
<222> LOCATION: (1)...(5416)
<223> OTHER INFORMATION: Note:/ n = a, t, c or g
<221> NAME/KEY: misc_feature
<222> LOCATION: (1)...(5416)
<223> OTHER INFORMATION: Note:/ Seq 4 contains Seq 1 (positions 223-
      1407), Seq 2 (positions 1921-2880), and Seq 3 (positions
      3381-3837)

<400> SEQUENCE: 8
tgcaggcatg caagctggaa ggaaacttgc cgcagccagg aaaacggtgc agtgcaagag     60
agggaagggg gcggcggttt gttggcaaga ttgaaacggt ggattgaaaa cagcttctga    120
```

-continued

| | | | |
|---|---|---|---|
| acaggtggat tgccgtttga caggtgagaa gtattttgcc agcagcaaga tacttcttat | 180 |
| ataatgaata ataatttatt taaaccgtcc tctgaatggg gcgagcagga gttttttgaat | 240 |
| ggaatttgtt tacgacgtgg cagaatcggc agtcagccct gcggtgatta aagtaatcgg | 300 |
| cttgggcggc ggcggttgca atgcatccaa taacatggtt gccaacaatg tgcgcggtgt | 360 |
| ggagtttatc agtgccaata cggatgcgca gtctctggca aaaaaccatg cggcgaagag | 420 |
| aatccagttg ggtacgaatc tgacacgcgg tttgggcgcg ggcgcgaatc ccgatatcgg | 480 |
| ccgtgcggca gcccaggaag accgggaagc cattgaagaa gccattcgcg gtgcgaatat | 540 |
| gctgtttatc acgaccggta tgggcggcgg taccggtacc ggttccgcgc cggttgttgc | 600 |
| tgagattgcc aagtctttgg gcattctgac cgttgccgtg gttacccgac cgttcgcata | 660 |
| tgaaggtaag cgcgtccatg tcgcacaggc agggttggaa cagttgaaag aacacgtcga | 720 |
| ttcgctgatt atcatcccga acgacaaact gatgactgca ttgggtgaag acgtaacgat | 780 |
| gcgcgaagcc ttccgtgccg ccgacaatgt attgcgcgat gcggtcgcag gcatttccga | 840 |
| agtggtaact tgcccgagcg aaatcatcaa cctcgacttt gccgacgtga aaaccgtgat | 900 |
| gagcaaccgc ggtatcgcta tgatgggttc gggttatgcc caaggtatcg accgtgcgcg | 960 |
| tatggcgacc gaccaggcca tttccagtcc gctgctggac gatgtaacct tggacggagc | 1020 |
| gcgcggtgtg ctggtcaata ttacgactgc tccggttgc ttgaaaatgt ccgagttgtc | 1080 |
| cgaagtcatg aaaatcgtca accaaagcgc gcatcccgat ttggaatgca aattcggtgc | 1140 |
| tgctgaagac gagaccatga gcgaagatgc catccggatt accattatcg ctaccggtct | 1200 |
| gaaagaaaaa ggcgcggtcg attttgttcc ggcaagggag gtagaagcgg ttgccccgtc | 1260 |
| caaacaggag caaagccaca atgtcgaagg tagatccgca ccaatcgcgg tatccgcacg | 1320 |
| atgaacctta ccgctgcgga tttcgacaat cagtccgtac ttgacgactt gaaatccctg | 1380 |
| cgattttgcg tcgtcaacac aattcagaca aataatgtgc tgtttgcccg taaacctgct | 1440 |
| gcctcccgaa tcggtttgtc cggtttggga ggtatgtttt tcaagatgtt gcaatttcgt | 1500 |
| acggtttgcg gtcggcggat tcagattttt ccacttgata cagactttca gatatggaca | 1560 |
| cttcaaaaca aacactgttg gacgggattt ttaagctgaa ggcaaacggt acgacggtgc | 1620 |
| gtaccgagtt gatggcgggt ttgacaactt ttttgacgat gtgctacatc gttaatcgtc | 1680 |
| aaccctctga ttttgggcga gaccggcatg gatatggggg cggtattcgt cgctacctgt | 1740 |
| atcgcgtctg ccaatcggct gttttgttat gggttttgtc ggcaactatc cgattgcact | 1800 |
| cgcaccgggg atggggctga atgcctattt caccttgcc gtcgttaagg gtatgggctg | 1860 |
| ccttggcagg ttgcgttggg tgcggtgttc atctccggtc tgattttcat cctgttcagc | 1920 |
| ttttttaaag tcagggaaat gctgtcaacg cactgcctat gggtttgaaa atgtcgattg | 1980 |
| ctgccggtat cggttttgttt ttggcactga tttccctgaa aggcgcaggc cattatcgtt | 2040 |
| gccaatccgg caaccttggt cggtttgggc gatattcatc agccgtccgc gttgttggca | 2100 |
| ctgttcggtt ttgctatggt ggtcgtattg ggacatttcc gcgttcaagg cgcaacatca | 2160 |
| tcaccatctt gaccattacc gtcattgcca gcctgatggg tttgaatgaa tttcacggca | 2220 |
| tcatcggcga agtaccgagc attgcgccga cttttatgca gatggatttt gaaggcctgt | 2280 |
| ttaccgtcag ctggtcagtg attttcgtct tcttcttggt cgatctattt gacagtaccg | 2340 |
| gaacgctggt cggcatatcc caccgtgccg ggctgctggt ggacggtaag ctgccccgcc | 2400 |
| tgaaacgcgc actgcttgca gactctaccg ccattatggc aggtgcggct ttgggtactt | 2460 |
| cttccaccac gccttatgtg gaaagcgcgg cgggcgtatc ggcaggcgga cggaccggcc | 2520 |

```
tgacggcggt taccgtcggc gtattgatgc tcgcctgcct gatgttttca cctttggcga   2580
aaagtgttcc cgcttttggc accgcgcccg ccctgcttta tgtcggcacg cagatgctcc   2640
gcagtgcgag ggatattgat tgggacgata tgacggaagc cgcacccgca ttcctgacca   2700
ttgtcttcat gccgtttacc tattcgattg cagacggcat cgccttcggc ttcatcagct   2760
atgccgtggt taaactttta tgccgccgca ccaaagacgt tccgcctatg gaatgggttg   2820
ttgccgtatt gtgggcactg aaattctggt atttgggctg attgattcga tattaaaaat   2880
gccgtctgaa aggttttcag acggcatttt gtttgccgat atattaattt ttattaaatt   2940
atataaaaat caaatacata ataaaataca tcggattgct taaaaataat acattgtttt   3000
ttatgtataa aatattttat aagttttcag gatttggatt attgaaaatt tttcttgatt   3060
tcctgacaat tttattgaaa caataattc aaaattaatc tagtttaatc atagaattaa   3120
aataaaatat taaaattatg taatgagtct ccttaaaaat gtttgacatt ttcagtcttg   3180
tgttttagat tatcgaaaaa taaaactaca taacactaca aaggaatatt actatgaaac   3240
caattcagat gttttcccct tttctgaata atccccttgt ttttcttcttg tctgcggttt   3300 tgccgcataa ttccgaacgg tctgctgttt ttctttgatt cgttttaaat atcaataaga   3360
taatttttcc catatatttt taatgattgg attgggatgc ccgacgcgtc ggatggctgt   3420
gttttgccgt ccgaatgtga tggaagcctg tccatactga aaaaagtct ataaggaga   3480 aatatgatga gtcaacactc tgccggagca cgtttccgcc aagccgtgaa agaatcgaat   3540
ccgcttgccg tcgccggttg cgtcaatgct tattttgcac gattggccac ccaaagcggt   3600
ttcaaagcca tctatctgtc tggcggcggc gtggcagcct gttcttgcgg tatccctgat   3660
ttgggcatta ccacaatgga agatgtgctg atcgacgcac gacgcattac ggacaacgtg   3720
gatncgcctc tgctggtgga catcgatgtg ggttggggcg gtgcattcaa tattgcccgt   3780
accattcgca actttgaacg cgccggtgtt gcagcggttc acatcgaaga tcaggtagcg   3840
caaaaacgct gcggtcaccg tccgaacaaa gccattgtta tctnaagatg naatggtcga   3900
ccgtatcaaa gctgccgtag atgcgcgcgt tgntgngaac ttcgtgatta tggcgcgtac   3960
cgatgcgctg gcggtagaag gtttggatgc cgctatcgaa cgcgcccaag cttgtgtcga   4020
aagccggtgc ggacatgatt tccctgaagg ccatgaccga tttgaacatg taccgccaat   4080
ttgcagatgc ggtgaaagtg cgtgttggcg aacattaccg agtttggttc cactccgctt   4140
tatacccaaa gcgagctggc tgaaaacggc gtgtcgctgg tgctgtatcc gctgtcatcg   4200
ttccgtgcag caagcaaagc cgctctgaat gtttacgaag cgattatgcg cgatggcact   4260
caggcggcgg tggtggacag tatgcaaacc cgtgccgagc tgtacgagca tctgaactat   4320
catgccttcg agcaaaaact ggataaattg tttcaaaaat gatttaccgc tttcagacgg   4380
tctttcaaca aatccgcatc ggtcgtctga aacccgaaa cccataaaaa cacaaaggag   4440
aaataccatg actgaaacta ctcaaacccc gaccttcaaa cctaagaaat ccgttgcgct   4500
ttcaggcgtt gcgccggta ataccgcttt tgtgtaccgtt ggccgcaccc ggcaacgatt   4560
tggagctatc gcggttacga catcttggat ttgggcacaa aaatgcgttt gaagaagtag   4620
cccacctgct gattcacggt catctgccca acaaattcga cgtggaagct tataaaagga   4680
agctcaaatc catgcgcggc ctgcctatcc gtgtattaaa gttttgggaa agcctgcctg   4740
cacataccca tccggatgga cggtaatggc gtaccggcgg tatccatgct gggctgcgtt   4800
catcccgaac gtgaaagcca tcccggaaag tgaagcgcgc gacatcgccg acaaactgat   4860
```

```
tgcagcctcg gagcctcctg ctgtactngg tatcaatatc gcacaacggc aaacgcattg    4920
agttgaagcg acgagagaca tcggcggtca tttcctgcaa ctgttncacg gcaacgccca    4980
agcgatcaca catcaaagcc atgcacgttt cactgattct gtatgcgaac acgagttcaa    5040
cgttctacct ttaccgtttg ccgttcttct ggtcggttct agccctgtaa aaagagaagg    5100
ttgttagctg gcgaaggttt gcagccgtta cagtttcccg cgttatagcg gccaagaaac    5160
gagtttggcg cacggtgaga attacctgtt gcaacgcccc agcctttacc atatgtgggc    5220
ctactggctt nggctagtgc taagaaacgc ggctatgcta gcgcctacat gccgagtgac    5280
gagcgtnacg ccatcgcaaa acttatacgc atttcgggaa gccaancgct ggcggcacaa    5340
agcctggata gttgtgcggc taacgnggcc attacgacct catgtatagt cctctgacat    5400
ggcgctantt gcgccc                                                    5416
```

<210> SEQ ID NO 9
<211> LENGTH: 16
<212> TYPE: RNA
<213> ORGANISM: Artificial Sequence
<220> FEATURE:
<223> OTHER INFORMATION: Description of Artificial Sequence; Note = synthetic construct
<221> NAME/KEY: misc_feature
<222> LOCATION: (1)...(16)
<223> OTHER INFORMATION: Note:/ n = g, a, c or t(u)
<221> NAME/KEY: misc_feature
<222> LOCATION: (1)...(16)
<223> OTHER INFORMATION: Note:/ = consensus target sequence for hairpin ribozyme

<400> SEQUENCE: 9
nnnsngucnn nnnnnn                                                    16

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence; Note = synthetic construct
<221> NAME/KEY: misc_feature
<222> LOCATION: (1)...(23)
<223> OTHER INFORMATION: Note:/ = oligonucleotide HEIC1

<400> SEQUENCE: 10
agcttgaggt cgacgggata tcg                                            23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence; Note = synthetic construct
<221> NAME/KEY: misc_feature
<222> LOCATION: (1)...(23)
<223> OTHER INFORMATION: Note:/ = oligonucleotide HEIC2

<400> SEQUENCE: 11
aattcgatat cccgtcgacc tca                                            23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence; Note =

```
        synthetic construct
<221> NAME/KEY: misc_feature
<222> LOCATION: (1)...(20)
<223> OTHER INFORMATION: Note:/ = primer B800F1

<400> SEQUENCE: 12
cacataaggc gtggtggaag                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence; Note =
        synthetic construct
<221> NAME/KEY: misc_feature
<222> LOCATION: (1)...(20)
<223> OTHER INFORMATION: Note:/ = target sequence for primer 800F8

<400> SEQUENCE: 13
ctcccaaacc ggacaaaccg                                              20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence; Note =
        synthetic construct
<221> NAME/KEY: misc_feature
<222> LOCATION: (1)...(22)
<223> OTHER INFORMATION: Note:/ = target sequence for primer 800F9

<400> SEQUENCE: 14
gtcaagtacg gactgattgt cg                                           22

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence; Note =
        synthetic construct

<400> SEQUENCE: 15

Gly Gly Gly Thr Gly Thr Gly
 1               5
```